(12) United States Patent
Bell et al.

(10) Patent No.: US 7,964,722 B2
(45) Date of Patent: Jun. 21, 2011

(54) LIGHT-DRIVEN ROTARY MOLECULAR MOTORS

(75) Inventors: Thomas W. Bell, Reno, NV (US);
Joseph I. Cline, Reno, NV (US);
Christine R. Cremo, Reno, NV (US);
Stephen L. Gillett, Reno, NV (US);
John H. Frederick, Reno, NV (US)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 261 days.

(21) Appl. No.: 10/874,356

(22) Filed: Jun. 24, 2004

(65) Prior Publication Data

US 2011/0077394 A1 Mar. 31, 2011

(51) Int. Cl.
*C07D 487/00* (2006.01)
*C07D 491/00* (2006.01)
*C07D 513/00* (2006.01)

(52) U.S. Cl. ......................... 540/476; 540/477; 540/479

(58) Field of Classification Search .................. None
See application file for complete search history.

(56) References Cited

FOREIGN PATENT DOCUMENTS
DE 1184762 * 1/1965

OTHER PUBLICATIONS

Boyd et al. Journal of the Chemical Society, Perkin Transactions I: Organic and Bio-organic Chemistry, 1977, 1308-1313.*
Moore et al. European Journal of Organic Chemistry, 2001, 2671-87.*
Solar et al Journal of the American Chemical Society, 1960, 82, 4285-86.*
Kice et al. Journal of the American Chemical Society, 1958, 80, 348-52.*
Kaldis et al. Tetrahedron Letters, 2002, 43, pp. 4049-4053, available online Apr. 19, 2002.*
Bergmann, E. Chemical Reviews, 1968, 68, pp. 41-84.*
V. Balzani et al., "Molecular Machines," Acc. Chem. Res. 31:405-414 (1998).
M. J. Bearpark et al., "Can Fulvene $S_1$ Decay Be Controlled? A CASSCF Study with MMVB Dynamics," J. Am. Chem. Soc. 118:5254-5260 (1996).
A. W. Bosman et al., "About Dendrimers: Structure, Physical Properties, and Applications," Chem. Rev. 99:1665-1688 (1999).
D. Brovelli et al., "Self-Assembled Monolayers of Alkylammonium Ions on Mica: Direct Determination of the Orientation of the Alkyl Chains," J. Colloid Interface Sci. 216:418-423 (1999).
C. A. Goss et al., "Application of (3-Mercaptopropyl)trimethoxysilane as a Molecular Adhesive in the Fabrication of Vapor-Deposited Gold Electrodes on Glass Substrates," Anal. Chem. 63(1):85-88 (1991).

T. Ha et al., "Single Molecule Dynamics Studied by Polarization Modulation," Phys. Rev. Lett. 77(19):3979-3982 (1996).
T. Ha et al., "Polarization Spectroscopy of Single Fluorescent Molecules," J. Phys. Chem. B 103:6839-6850 (1999).
G. Hähner et al., "Orientation and electronic structure of methylene blue on mica: A near edge X-ray absorption one structure spectroscopy study," J. Chem. Phys. 104(19):7749-7757 (1996).
D. B. Haniford et al., "Facile transition of poly[d(TG)•d(CA)] into a left-handed helix in physiological conditions," Nature 302:632-634 (1983).
D. C. Hanley et al., "Quantitative Dosing of Surfaces with Fluorescent Molecules: Characterization of Fractional Monolayer Coverage by Counting Single Molecules," Anal. Chem. 73:5030-5037 (2001).
N. Harada et al., "Chemistry of Unique Chiral Olefins—A Light-Powered Chiral Molecular Motor with Monodirectional Rotation," Nippon Kagaku Kaishi 9:591-603 (2000).
C. J. Hawker, "Dendritic and Hyperbranched Macromolecules—Precisely Controlled Macromolecular Architectures," Adv. Polym. Sci. (Macromolecular Architectures) 147:113-160 (1999).
B. W. Howk et al., "Synthesis of Acetylenic Acetals, Ketals and Orthoesters," J. Am. Chem. Soc. 80:4607-4609 (1958).
A. L. Huston et al., "Photochemical bleaching of adsorbed rhodamine 6G as a probe of binding geometries on a fused silica surface," Chem. Phys. 149.401-407 (1991).
Y. Ishii, et al., "Imaging and Nano-Manipulation of Single Actomyosin Motors at Work," Clin. Exp. Pharmacol. Physiol. 27:229-237 (2000).
H. Izumi et al., "Synthesis and Cyclization Reaction of *cis,cis*-1,3,5-Triformyl-1,3,5-trimethylcyclohexane," J. Org. Chem. 62:1173-1175 (1997). H. Izumi et al., "Intermolecular Interaction of Adjacent Hydroxymethyl, Formyl, and Carboxyl Groups: Proximity Effect in the Swern Oxidation of *cis,cis*-1,3,5-Tris(hydroxymethyl)-1,3,5-trimethylcyclohexane," J. Org. Chem. 64:4502-4505 (1999).
K. S. Jeong et al., "Molecular Recognition. Asymmetric Complexation of Diketopiperazines," J. Am. Chem. Soc. 112:6144-6145 (1990).

(Continued)

*Primary Examiner* — Noble Jarrell
(74) *Attorney, Agent, or Firm* — J.A. Lindeman & Co., PLLC

(57) ABSTRACT

Compounds of Formula (1) are disclosed.

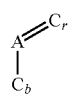

(1)

$C_b$ is a carbocyclic or heterocyclic group having an atom within the cyclic structure selected from C, N, Si, and $C_r$, and singly bound to A. A is CR, COR, CSR, $CNR_2$, CCN, $CCONR_2$, $CNO_2$, CNNAr, $CX^1$, or N. $C_r$ is a chromophore having a substantially planar cyclic structure. The compounds function as nanometer-scale rotary molecular motors powered and controlled by light energy. The design of the molecular motor devices is flexible so that the rotary direction, drive light wavelength, and other physical characteristics can be varied. The compounds can be chemically functionalized to allow it to be integrated into or attached to a variety of structures. The device can be used in applications where mechanical power, positional control, and information encoding are to be generated at the size scale of individual molecules.

9 Claims, 31 Drawing Sheets

OTHER PUBLICATIONS

K. S. Jeong et al., "Convergent Functional Groups. 10. Molecular Recognition of Neutral Substrates," J. Am. Chem. Soc. 113:201-209 (1991).

W. Kantlehner et al., "Ein neues ergiebiges Verfahren zur Herstellung von Trialkyl-orthobenzoaten und Trialkyl-orthophenylpropynoaten," Synthesis 380-381 (1981).

T. R. Kelly et al., "A Molecular Brake," J. Am. Chem. Soc. 116:3657-3658 (1994).

T. R. Kelly et al., "In Search of Molecular Ratchets," Angew. Chem. Int. Ed. Engl. 36(17):1866-1868 (1997).

T. R. Kelly et al., "Unidirectional rotary motion in a molecular system," Nature 401:150-152 (1999).

T. R. Kelly et al., "A Rationally Designed Prototype of a Molecular Motor," J. Am. Chem. Soc. 122:6935-6949 (2000).

D. S. Kemp et al., "Synthesis and Conformational Analysis of cis,cis-1,3,5-Trimethylcyclohexane-1,3,5-tricarboxylic Acid," J. Org. Chem. 46:5140-5143 (1981).

R. Knorr et al., "$^1$H-Kernresonanzverschiebungen in der Gerüstebene anisotroper CO-, CN- und CC-Doppelbindungen," Chem. Ber. 112:3490-3514 (1979).

N. Koumura et al., "Lightdriven monodirectional molecule rotor," Nature 401:152-155 (1999).

R. Kuhn et al., "Über Hochacide Kohlenwasserstoffe," Liebigs Ann. Chem. 654:64-81 (1962).

R. C. Larock et al., "Synthesis of 9-Alkylidene-9H-fluorenes by a Novel, Palladium-Catalyzed Cascade Reaction of Aryl Haiides and 1-Aryl-1-alkynes," J. Org. Chem. 66:7372-7379 (2001).

J.-M. Lehn, "Perspectives in supramolecular chemistry: From molecular recognition towards self-organization," Pure & Appl. Chem. 66(10/11):1961-1966 (1994).

L. F. Levy et al., "CXXIII. 4-Aminophthalide and Some Derivatives," J. Chem. Soc. 867-871 (1931).

M. Li et al., "Surface-Directed Adsorption in the Expitaxy Growth of Streptocyanine Dye Crystals," J. Phys. Chem. B 103:11161-11168 (1999).

M. Lieberherr et al., "Optical-Environment-Dependent Effects on the Fluorescence of Submonomolecular Dye Layers on Interfaces," Surf. Sci. 189:954-959 (1987).

T. Lindel et al., "Synthesis of the Marine Natural Product Oroidin and Its Z-Isomer," J. Org. Chem. 65:2806-2809 (2000).

J. Martin et al., "Factors Influencing the Basicities of Triarylcarbinols. The Synthesis of Sesquixanthydrol," J. Am. Chem. Soc. 86:2252-2256 (1964).

T. Masquelin et al., "A New Spproach to the Synthesis of N-Protected 2- and 5-Substituted 3-Halopyrroles," Synthesis 276-284 (1995).

O. A. Matthews et al., "Dendrimers—Branching Out From Curiosities Into New Technologies," Prog. Polym. Sci. 23:1-56 (1998).

M. J. McLean et al., "Consecutive A•T pairs can adopt a left-handed DNA structure," Proc. Natl. Acad. Sci. USA 83:5884-5888 (1986).

G. Mehta et al., "Synthesis and X-ray crystal structure of 1,3,5-tris(fluoren-9-ylidenemethyl)benzene: towards a $C_{48}$-fragment of [60]-fullerene," J. Chem. Soc. Perkin Trans. 1:1787-1788 (1995).

M. Minabe et al., "Bildung von 1,4-Bis(2,2'-biphenylylen)-1,3-butadien," Bull. Chem. Soc. Jpn. 46:1573-1575 (1973).

M. Minabe et al., "A Facile Synthesis of 4H-Cyclopenta[def]phenanthrene," Bull. Chem. Soc. Jpn. 61:995-996 (1988).

W. Moerner et al., "Illuminating Single Molecules in Condensed Matter," Science 283:1670-1676 (1999).

C. Montemagno et al., "Constructing nanomechanical devices powered by biomolecular motors," Nanotechnology 10:225-231 (1999).

B. Morgan et al., "Enzymatic Kinetic Resolution of Piperidine Atropisomers: Synthesis of a Key Intermediate of the Farnesyl Protein Transferase Inhibitor, SCH66336," J. Org. Chem. 65(18):5451-5459 (2000).

R. S. Murphy et al., "Photophysical characterization of fluorenone derivatives," J. Photochem. Photobiol. A: Chemistry 110:123-129 (1997).

S. Nagase et al., "Endohedral Metallofullerenes: New Spherical Cage Molecules with Interesting Properties," Bull. Chem. Soc. Jpn. 69:2131-2142 (1996).

S. A. Nepogodiev et al., "Cyclodextrin-Based Catenanes and Rotaxanes," Chem. Rev. 98:1959-1976 (1998).

M. Neuenschwander et al., "Synthese von Benzofulvenen und Dibenzofulvenen über 1-Chloroalkyl-acetate," Helv. Chim. Acta 60:1073-1086 (1977).

S. Nie et al., "Probing Individual Molecules with Confocal Fluorescence Microscopy," Science 266:1018-1021 (1994).

Y. Okamoto et al., "XI*. Controlled Chiral Recognition of Cellulose Triphenylcarbamate Derivatives Supported on Silica Gel," J. Chromatogr. 363:173-186 (1986).

Y. Okamoto et al., "Polysaccharide Derivatives for Chromatographic Separation of Enantiomers," Angew. Chem. Int. Ed. 37:1020-1043 (1998).

T. Olsson et al., "Rotational Barriers and Electronic Structures of Some 6,6-Dihetero-substituted Fulvenes," Acta Chem. Scand. B 36:23-30 (1982).

B. S. Ong et al., "Synthesis, molecular and electron transport properties of 2-alkyltrinitrofluoren-9-ones," Can. J. Chem. 63:147-152 (1985).

K. Pal et al., "A General Stereocontrolled Synthesis of cis-2,3 Disubstituted Pyrrolidines and Piperidines," Tetrahedron Lett. 34(39):6205-6208 (1993).

G. C. Paul et al., "Unexpected Coupling Reaction of 9-Lithiobromomethylene-9H-fluorene with 6.6-Dicyclopropylfulvene," Synthesis 524-526 (1997).

C. S. Peskin et al., "Coordinated Hydrolysis Explains the Mechanical Behavior of Kinesin," Biophys. J. 68:202s-211s (1995).

D. L. Pilloud et al., "Self-Assembled Monolayers of Synthetic Hemoproteins on Silanized Quartz," J. Phys. Chem. B 102:1926-1937 (1998).

L. A. Pinck et al., "Derivatives of Fluorene," J. Am. Chem. Soc. 69:723 (1947).

V. J. Rao, "Photochemical cis-trans isomerization from the Singlet Excited State," in Organic Molecular Photochemistry (V. Ramamurthy et al., Eds.), Marcel Dekker, New York, pp. 169-207 (1999).

F. M. Raymo et al., "Interlocked Macromolecules," Chem. Rev. 99:1643-1663 (1999).

J. Rebek, Jr et al., "Convergent Functional Groups. 3. A Molecular Cleft Recognizes Substrates of Complementary Size, Shape, and Functionality," J. Am. Chem. Soc. 109:2426-2431 (1987).

S. Rice et al., "A structural change in the kinesin motor protein that drives motility," Nature 402:778-784 (1999).

J. Saltiel et al., "Cis-Trans Isomerization of Alkenes," in CRC Handbook of Organic Photochemistry and Photobiology (W. M. Horspool et al., Eds.), CRC Press, Boca Raton, pp. 3-15 (1995).

H. Sano et al., "Dipole Radiation Pattern From Surface Adsorbed Dye Molecules: Effects of Surface Roughness," Surf. Sci. 223:621-631 (1989).

J.-P. Sauvage, ed., Molecular Motors and Machines, vol. 99 of Structure and Bonding (Springer, Berlin, 2001).

M. A. Schmid et al., "Unbridged cyclopentadienyl-fluorenyl complexes of zirconium as catalysts for homogeneous olefin polymerization," J. Organomet. Chem. 501:101-106 (1995).

A. M. Schoevaars et al., "Towards a Switchable Molecular Rotor. Unexpected Dynamic Behavior of Functionalized Overcrowded Ethylenes," Book of Abstracts, 212th ACS National Meeting ORGN-134 (1996).

Z. A. Shabarova et al., "DNA-like duplexes with repetitions: efficient template-guided polycondensation of decadeoxyribonucleotide imidazolide," FEBS Lett. 154(2):288-292 (1983).

V. Sharma et al., "Synthesis and Structure of 2,2'-Dihydroxybenzophenones and 1,8-Dihydroxyfluorenones," J. Org. Chem. 59:7785-7792 (1994).

H. Shinohara, "Endohedral metallofullerenes," Rep. Prog. Phys. 63:843-892 (2000).

C. K. Singleton et al., "S1 Nuclease Recognizes DNA Conformational Junctions between Left-handed Helical (dT-dG)$_n$•(dC-dA)$_n$, and Contiguous Right-handed Sequences," J. Biol. Chem. 259(3):1963-1967 (1984).

D. K. Smith et al., "Supramolecular Dendrimer Chemistry: Molecular Recognition within the Dendritic Environment," in Supramolecular Science: Where It Is and Where It Is Going, NATO ASI Ser., Ser. C 527 pp. 261-272 (1999).

J. G. Smith et al., "2-(Dimethoxymethyl)benzyl Alcohol: A Convenient Isobenzofuran Precursor," J. Org. Chem. 48:5361-5362 (1983).

R. K. Soong et al., "Powering an Inorganic Nanodevice with a Biomolecular Motor," Science 290:1555-1558 (2000).

B. Space et al., "Feasibility of using photophoresis to create a concentration gradient of solvated molecules," J. Chem. Phys. 105(21):9515-9524 (1996).

R. Stracke et al., "Physical and technical parameters determining the functioning of a kinesin-based cell-free motor system," Nanotechnology 11:52-56 (2000).

T. Strother et al., "Covalent attachment of oligodeoxyribonucleotides to amine-modified Si (001) surfaces," Nucleic Acids Research 28(18):3535-3541 (2000).

P. Tamarat et al., "Ten Years of Single-Molecule Spectroscopy," J. Phys. Chem. A 104(1):1-16 (2000).

Q. Tian et al., "Synthesis of 9-Alkylidene-9$H$-fluorenes by a Novel Palladium-Catalyzed Rearrangement," Org. Lett. 2(21):3329-3332 (2000).

K. Tomooka et al., "[1,2]-Wittig Rearrangement of Acetal Systems: A Highly Stereocontrolled Conversion of $O$-Glycosides to $C$-Glycosides," J. Am. Chem. Soc. 118:3317-3318 (1996).

K. Tomooka et al., "Stereoselective Synthesis of Highly Functionalized $C$-Glycosides based on Acetal [1,2] and [1,4] Wittig Rearrangements," Angew. Chem. Int. Ed. 39(24):4500-4502 (2000).

K. Tomooka et al., "Stereoselective Total Synthesis of Zaragozic Acid A based on an Acetal [1,2] Wittig Rearrangement," Angew. Chem. Int. Ed. 39(24):4502-4505 (2000).

J. K. Trautman et al., "Time-resolved spectroscopy of single molecules using near-field and far-field optics," Chem. Phys. 205:221-229 (1996).

A. Tsuge et al., "A Facile Synthesis of 1,8- and 1,7-Bis(chloromethyl)fluorenes," Synthesis 205-206 (1993).

J. Vacek et al., "A molecular 'Tinkertoy' construction kit: Computer simulation of molecular propellers," New J. Chem. 21:1259-1268 (1997).

J. Vacek et al., "Simulation of Chiral Molecular Mobiles," Book of Abstracts, 219th ACS National Meeting PHYS-130 (2000).

J. Vacek et al., "Molecular dynamics of a grid-mounted molecular dipolar rotor in a rotating electric field," Proc. Natl. Acad. Sci. U.S.A. 98(10):5481-5486 (2001).

T. Vallant et al., "Formation of Self-Assembled Octadecylsiloxane Monolayers on Mica and Silicon Surfaces Studied by Atomic Force Microscopy and Infrared Spectroscopy," J. Phys. Chem. B 102:7190-7197 (1998).

R. A. van Delden et al., "Unidirectional rotary motion in a liquid crystalline environment: Color tuning by a molecular motor," Proc. Nat. Acad. Sci. 99(8):4945-4949 (2002).

I. Von et al., "Some 9-Acylfluorenes and Derived Vinylamines," J. Org. Chem. 9:155-169 (1944).

D.H. Waldeck, "Photoisomerization Dynamics of Stilbenes," Chem. Rev. 91:415-436 (1991).

M. Yoshida et al., "Synthesis of 4$H$-cyclopenta[$def$]phenanthrene from Fluorene Skeleton," Bull. Chem. Soc. Jpn. 56:2179-2180 (1983).

P. M. Ajayan et al., "Carbon nanotubes: From macromolecules to nanotechnology," Proc. Natl. Acad. Sci. U.S.A. 96(25):14199-14200 (1999).

H. G. Alt et al., "Syndiospezifische Polymerisation von Propylen: 2- und 2,7-substituierte Metallocenkomplex des Typs ($C^{13}H_{8-n}$ $R_nCR'_2C_5H_4$)$MCl_2$($n$=1,2; R=Alkoxy, Alkyl; Aryl, Hal; R'=Me; Ph; M=Zr, Hf)," J. Organomet. Chem. 522:39-54 (1996).

I. Antipin et al., "Cryptate Acidity Scales. IV. Spectrophotometric and Conductometric Study of [2.1.1]cryptates of Lithium Salts of CH Acids," J. Org. Chem., USSR 25(1):1-9 (1989).

T. Arai et al., "Novel insights into photoisomerization of olefins," Pure & Appl. Chem. 60:989-998 (1988).

T. Arai et al., "Photochemical One-Way Adiabatic Isomerization of Aromatic Olefins," Chem. Rev. 93:23-39 (1993).

T. Arai, Organic Molecular Photochemistry (V. Ramamurthy et al., Eds.), Marcel Dekker, New York, pp. 131-167 (1999).

P. R. Ashton et al., "A Photochemically Driven Molecular-Level Abacus," Chem. Eur. J. 6(19):3558-3574 (2000).

G. D. Bachand et al., "Constructing Organic/Inorganic NEMS Devices Powered by Biomolecular Motors," Biomed. Microdevices 2:179-184 (2000).

V. Balzani et al., "Artificial Molecular Machines," Angew. Chem. Int. Ed. 39:3348-3391 (2000).

T. W. Bell et al., "Bond Angle Versus Torsional Deformation in an Overcrowded Alkene: 9-(2,2,2-Triphenylethylidene)fluorene," Chem. Eur. J. 8(21):5001-5006 (2002).

E. D. Bergmann et al., "No. 231.—Fulvènes et éthylènes thermochromes. 2e partie. Moments dipolaires," Bull. Soc. Chim. Fr. 1084-1091 (1950).

English-language abstract of E. D. Bergmann et al., "No. 231.—Fulvènes et éthylènes thermochromes. 2e partie. Moments dipolaires," Bull. Soc. Chim. Fr. 1084-1091 (1950).

E. D. Bergmann et al., "No. 234.—Fulvènes et éthylènes thermochromes. 5e Partie. Un cas d'isomérie cis-trans dans la série du dibenzofulvène," Bull. Soc. Chim. Fr. 1103-1104 (1950).

English-language abstract of E. D. Bergmann at al., "No. 234.—Fulvènes et éthylènes thermochromes. 5e Partie. Un cas d'isomérie cis-trans dans la série du dibenzofulvène," Bull. Soc. Chim. Fr. 1103-1104 (1950).

R. C. Bernotas et al., "A New Family of Five-Carbon Iminoalditols Which Are Potent Glycosidase Inhibitors," Tetrahedron Lett. 31(24):3393-3396 (1990).

D. S. Bethune et al., "Atoms in carbon cages: the structure and properties of endohedral fullerenes," Nature 366:123-128 (1993).

R. Boyce et al., "1,1-Diphenylalkenes. Part V. C-1 vs. C-3 Alkylation of Allylic Carbanions; Applicability of the Principle of Least Motion," J. Chem. Soc., Perkin Trans. I 531-534 (1975).

A. M. Brouwer et al., "Photoinduction of Fast, Reversible Translational Motion in a Hydrogen-Bonded Molecular Shuttle," Science 291:2124-2128 (2001).

P. Casara et al., "Stereospecific Synthesis of (2$R$,5$R$)-Hept-6-yne-2,5-diamine: A Potent and Selective Enzyme-activated Irreversible Inhibitor of Ornithine Decarboxylase (ODC)," J. Chem. Soc. Perkin Trans. 1 1985:2201-2207 (1985).

M. P. Cava et al., "Thionation Reactions of Lawesson's Reagents," Tetrahedron 41(22):5061-5087 (1985).

R. Cherkasov et al., "Organothiophosphorus Reagents in Organic Synthesis," Tetrahedron 41(13):2567-2624 (1985).

W. Chew et al., "Synthesis of Substituted Fluorenones and Substituted 3',3'-Dichlorospiro[fluorene-9,2'-thiiranes] and Their Reactivities," J. Org. Chem. 58:4398-4404 (1993).

B. C. Chu et al., "Derivatization of unprotected polynucleotides," Nucleic Acids Res. 11(18):6513-6529 (1983).

B. A. Connolly et al., "Chemical synthesis of oligonucleotides containing a free sulphydryl group and subsequent attachment of thiol specific probes," Nucleic Acids Res. 13(12):4485-4502 (1985).

L. Contreras et al., "Reactions of phthalans with dienophiles. I. Synthesis of naphthalenes from phthalans and activated acetylenes," Can. J. Chem. 58:2573-2579 (1980).

R. Cooke, "The structure of a molecular motor," Curr. Biol. 3(9):590-592 (1993).

R. Cooke, "The actomyosin engine," FASEB J. 9:636-642 (1995).

N. J. Córdova et al., "Dynamics of single-motor molecules: The thermal ratchet model," Proc. Natl. Acad. Sci. U. S. A. 89:339-343 (1992).

C. R. Cremo et al., "Interaction of Myosin Subfragment l with Fluorescent Ribose-Modified Nucleotides. A Comparison of Vanadate Trapping and $SH_1$-$SH_2$ Cross-Linking," Biochemistry 29:3309-3319 (1990).

C. R. Cremo et al., "Two Heads are Required for Phosphorylation-Dependent Regulation of Smooth Muscle Myosin," J. Biol. Chem. 270(5):2171-2175 (1995).

A. P. Davis, "Tilting at Windmills? The Second Law survives," Angew. Chem. Int. Ed. 37(7):909-910 (1998).

J. R. Dennis et al., "Molecular shuttles: directed motion of microtubules along nanoscale kinesin tracks," Nanotechnology 10:232-236 (1999).

M. J. S. Dewar et al., "Ground States of σ-Bonded Molecules. XV. Barriers to Rotation about Carbon-Carbon Bonds," J. Am. Chem. Soc. 94:2699-2704 (1972).

R. Dickson et al., "Simultaneous Imaging of Individual Molecules Aligned Both Parallel and Perpendicular to the Optic Axis," Phys. Rev. Lett. 81(24):5322-5325 (1998).

C. Donati et al., "Potential GABAB Receptor Antagonists. III Folded Baclofen Analogues Based on Phthalide," Aust. J. Chem. 42:787-795 (1989).

A. P. Downing et al., "The Study of the Aromaticity and the Rotational isomerism of 6-Di-methylaminofulvenes by Nuclear Magnetic Resonance Spectroscopy," J. Chem. Soc. B 111-119 (1969).

K. E. Drexler, Engines of Creation (Anchor Press, New York, NY, 1986).

K. E. Drexler, Nanosystems: Molecular Machinery, Manufacturing, and Computation (John Wiley and Sons, New York, NY, 1992).

J. Dreyer et al., "Excited states and photochemical reactivity of fulvene. A theoretical study," J. Chem. Phys. 101:10655-10665 (1994).

M. Fischer et al., "Dendrimers: From Design to Application—A Progress Report," Angew. Chem., Int. Ed. 38:884-905 (1999).

M. Fyfe et al., "X-ray Crystallographic Studies on the Noncovalent Syntheses of Supermolecules," J. Struct. Chem. 10(3):243-259 (1999).

P. A. Gale, "Supramolecular chemistry: from complexes to complexity," Philos. Trans. R. Soc. Lond. A 358:431-453 (2000).

P. Gärtner et al., "[1,2]-Wittig rearrangement of acetals. Part 1: Investigation about structural requirements", Tetrahedron: Asymmetry 10:4811-4830 (1999).

P. Gärtner et al., "[1,2]-Wittig rearrangement of acetals. Part 2: The influence of reaction conditions," Tetrahedron: Asymmetry 11:1003-1013 (2000).

E. Ghera et al., "Reactions of Active Methylene Compounds in Pyridine Solution. II. Aldol-type Reactions of Indene and Fluorene," J. Am. Chem. Soc. 82:4945-4952 (1960).

H. W. Gibson et al., "New Triarylmethyl Derivatives: 'Blocking Groups' for Rotaxanes and Polyrotaxanes," J. Org. Chem. 58:3748-3756 (1993).

M. Gómez-López et al., "The art and science of self-assembling molecular machines," Nanotechnology 7:183-192 (1996).

M. Gomez-Lopez et al., "Molecular and Supramolecular Nanomachines," in Handbook of Nanostructured Materials and Nanotechnology, vol. 5, edited by H. S. Nalwa (Academic Press, 2000), pp. 225-275.

X. S. Xie et al., "Optical Studies of Single Molecules at Room Temperature," Annu. Rev. Phys. Chem. 49:441-480 (1998).

T. Yanagida et al., "Single-motor mechanics and models of the myosin motor," Phil. Trans. R. Soc. Lond. B 355:441-447 (2000).

E. Yashima et al., "Polysaccharide-Based Chiral LC Columns," Synlett 344-360 (1998).

T. Yatsuhashi et al., "Photophysical Properties of Intramolecular Charge-Transfer Excited Singlet State of Aminofluorenone Derivatives," J. Phys. Chem. A 102:3018-3024 (1998).

F. M. Ausubel et al., eds., "Short Protocols in Molecular Biology: A Compendium of Methods From Current Protocols in Molecular Biology" (John Wiley and Sons, New York, NY, 4th ed. 1999).

A. L. Balch, "Structural Inorganic Chemistry of Fullerenes and Fullerene-like Compounds," in Fullerenes: Chemistry, Physics, and Technology, edited by K. M. Kadish and R. S. Ruoff (John Wiley and Sons, Inc., New York, NY, 2000), pp. 177-223.

P. Bernath, "Spectra of Atoms and Molecules" (Oxford University Press, New York, NY, 1995).

P. J. F. Harris, "Carbon Nanotubes and Related Structures: New Materials for the Twenty-first Century" (Cambridge Univ. Press, Cambridge, UK, 1999).

H.-H. Perkampus el al., eds., "UV Atlas of Organic Compounds, vol. V" (Plenum Press, New York, 1971).

F. Vögtle, ed., "Dendrimers II: Architecture, Nanostructure and Supramolecular Chemistry" (Topics of Current Chemistry, vol. 210) (Springer, Berlin, Germany, 2000).

P. Zanello, "Electrochemical and Structural Aspects of Metallofullerenes," in Chem. Beginning Third Millennium, Proc. Ger.-Ital. Meet., edited by L. Fabbrizzi and A. Poggi (Springer-Verlag, Berlin, Germany, 2000), pp. 247-278.

* cited by examiner

Figure 1: Structure of Motor I

Figure 2: Scheme 1

Figure 3: Scheme 2

Figure 4: Scheme 3

Figure 5: Scheme 4

Figure 6: Scheme 5

Scheme 6

Figure 7: Scheme 6

Figure 8: Scheme 7

Figure 9: Retrosynthetic analysis of a molecular motor 1 in Example 2.

Figure 10: Retrosynthetic analysis of base unit 4 in Example 2.

Figure 11: Syntheisis of Intermediate 6 in Example 2.

Figure 12: Synthesis of 16, an immediate precursor to intermediate 4 in Example 2.

Figure 13: Synthesis of model compounds with various rotor substituents in Example 2.

Figure 14: Motor II

Figure 15: Scheme 8

Figure 16: Scheme 9

Figure 17: Scheme 10

Figure 18: Scheme 11

UV absorption spectra of both stereoisomers of 2-*tert*-butyl-9-(2,2,2)-triphenylethylidenefluorene (CH$_3$CN, 9.2 μM): (*E*)-4, dashed line; (Z)-4, solid line.

Photoisomerization data at 266 nm showing mole fractions of (Z)-4 (• symbols) and (E)-4 (▲ symbols) as a function of the average number of photons absorbed. The upper panel shows data for a [E] = 1. The lower panel shows data for a [Z] = 1. Solid curves show a fit to the kinetic model with photoisomerization rates $k_{ZE}$ = 0.074 and $k_{EZ}$ = 0.10 in Eqs. 1 and 2.

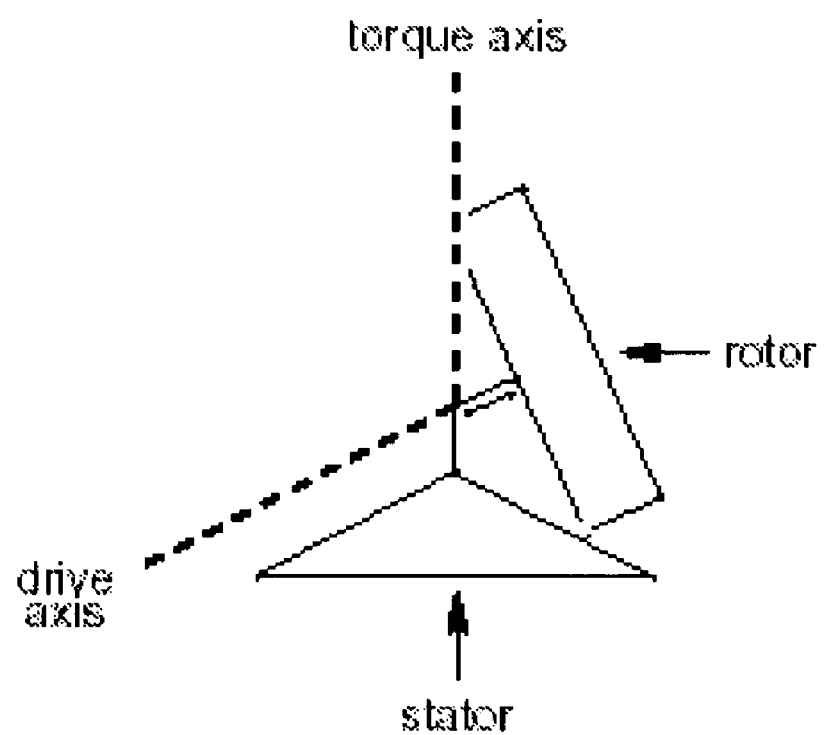
Figure 29: Components of Molecular Motor Design

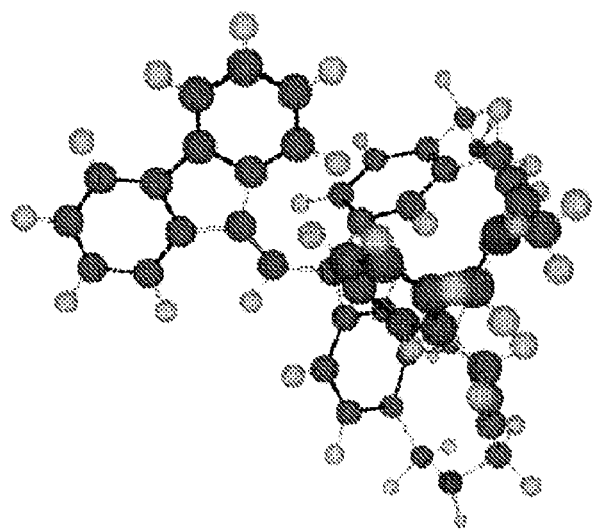
Figure 30(c): Side View
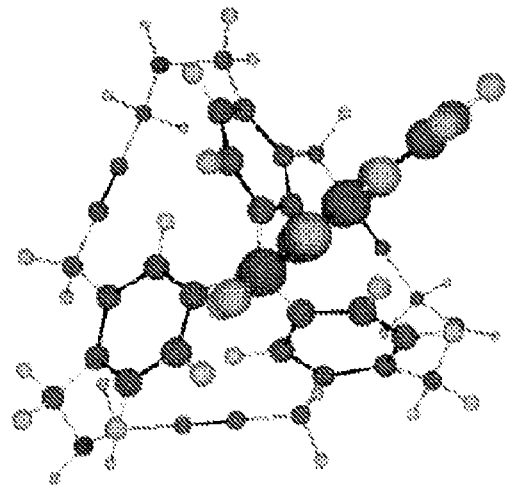
Figure 30(b): Top View
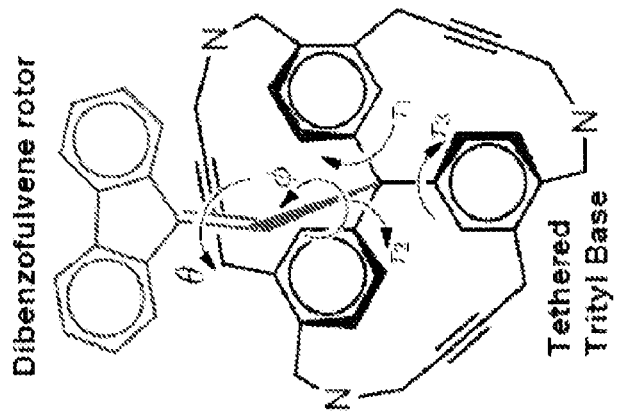
Figure 30(a): Motor I

LIGHT-DRIVEN ROTARY MOLECULAR MOTORS

GOVERNMENT LICENSE RIGHTS

This invention was made with United States Government support under a grant from the National Science Foundation, Grant No. CHE0210549. The United States Government has certain rights in the invention.

CROSS-REFERENCE TO RELATED APPLICATIONS

This application claims priority under 35 U.S.C. §119(e) to U.S. Provisional Application Ser. No. 60/407,520, filed Aug. 31, 2002, which is incorporated herein by reference.

FIELD OF INVENTION

This invention relates to the areas of synthetic chemistry photochemistry, advanced materials, and nanometer-scale devices. Specifically it relates to the construction of controllable molecule-sized synthetic rotary motors.

BACKGROUND

Technology at the molecular scale is built on two complementary strategies for manipulating matter and energy. Static nonstructures, exemplified by carbon nanotubes,[1-3] metallofullerenes,[4-8] dendrimers,[9-14] and supramolecular assemblies,[15-19] are designed molecular systems that exhibit specific useful properties, including electrical or thermal conductivity, tensile strength, and photochromism. Dynamic nanomachines,[20-25] on the other hand, are molecular systems designed to perform some type of work when powered by an energy source, such as an added chemical reagent, electron transfer induced by an electrical potential, or absorption of light. Both types of molecular-scale devices are needed for the development of a comprehensive nanotechnology.[21] The construction of dynamic molecular machines is the next challenge for chemists, physicists, and materials scientists.[26]

One approach to developing nanoscale systems that perform work reproducibly has been to study and exploit natural biological machines, such as the proteins myosin[27-31] and kinesin.[27,32-35] Biomolecular motors are now emerging as candidates for power sources integrated into artificial nanomechanical structures. As an example, Montemagno and coworkers,[36-39] have demonstrated this approach using an F1-ATPase rotary motor driving a >>1000 nm long nickel rod "propeller" powered by ATP chemical fuel.

Harnessing biomolecular motors offers the advantages of proven operation and a phenomenal energy efficiency that has been optimized in naturally occurring biological systems.[39] However, these motors have a number of characteristics that limit their utility for powering artificial nanostructures in many applications. Among these are a lack of precise temporal control for energizing/deenergizing the motor, a complex and degradable fuel source, and relatively low speed operation (~8 Hz for the rotary ATPase motor). Most restrictive is the narrow range of environmental conditions (e.g. solvent, pH, temperature) which biomolecular motors can tolerate. Biomolecular motors have dimensions of several tens of nm, making them awkward to incorporate into structures where the motor footprint or actuator travel is desired on the scale of individual small molecules (~1 nm).

Synthetic biomimetic molecular motors potentially other a much smaller size, robustness, and the possibility of tailoring the design features for targeted performance criteria. There has not yet been a demonstration of a practical synthetic nanoscale motor that can deliver power to a nanoscale mechanical load, but a number of approaches are being explored. The construction of interlocking molecular systems ("molecular shuttles") in which a cyclic molecule can be induced to move along a chain of atoms in response to physical or chemical stimuli others the possibility of controllable linear motion.[22,23,25,34,40-44] Several groups recently have reported the successful design of molecules that exhibit unidirectional rotary motion, essentially prototypes of molecular motors that are biomimetic analogs of rotary biological motors in, for example, flagelia. Kelly and co-workers[45-48] have developed a system comprised of a helicene\ratchet" attached to a triptycene\rotor" whose rotary motion in one direction is driven by a sequence of chemical reactions. The research groups of Feringa and Harada[49-52] have introduced a system in which unidirectional rotary motion is achieved by a four-step process involving two thermal chemical reactions and two photochemical reactions. Michl has conceptualized a large-scale molecular "propeller" that should exhibit unidirectional motion under bombardment from a beam of He atoms according to computer simulations.[53,54] The structures envisioned by these groups demonstrate the feasibility of achieving unidirectional rotational motion despite concerns that such motion may violate the second law of thermodynamics.[55] In fact, the success of these systems is based on creating a non-equilibrium system whose relaxation to equilibrium is responsible for the observed dynamics.

Both of the existing synthetic motor prototypes depend in part or in whole on thermal chemical reactions to achieve rotary motion.[48,50] These designs typically have low repetition rates (on the order of seconds), require thermal cycling, and potentially poor temporal and positional control. A more desirable motor prototype would have high repetition rates (> kHz), and would be ideally controllable with a long operational lifetime. Many of these design goals can be attained using either an electron-transfer event or the absorption of light as a power source.[25]

SUMMARY OF THE INVENTION

The invention relates to compounds of Formula (1):

(1)

where $C_b$ is a carbocyclic or heterocyclic group having an atom within the cyclic structure selected from C, N, Si, and Sn and singly bound to A; A is CR, COR, CSR, CNR$_2$, CCN, CCONR$_2$, CNO$_2$, CNNAr (wherein Ar is aryl or heteroaryl), CX' (wherein X' is a halide), or N; and $C_r$ is a chromophore which has a substantially planar cyclic structure. The compounds of the invention function as nanometer-scale rotary molecular motor that are powered and controlled by light energy. The motors are unique in that their operation relies on light energy alone. The design of the molecular motor devices is flexible so that the rotary direction, drive light wavelength, and other physical characteristics can be varied. The compounds can be chemically functionalized to allow it to be integrated into or attached to a variety of structures. The device can be used in applications where mechanical power, positional control, and information encoding are to be generated at the size scale of individual molecules.

BRIEF DESCRIPTION OF DRAWINGS

FIG. 29 depicts the components of molecular motor design.

FIG. 30(a) depicts a representation of the structure of a Motor I.

FIG. 30(b) depicts a top view of the ball-and-stick model of the structure of a Motor I.

FIG. 30(c) depicts a side view of the ball-and-stick model of the structure of a Motor I.

DETAILED DESCRIPTION OF THE INVENTION

Figure 1:
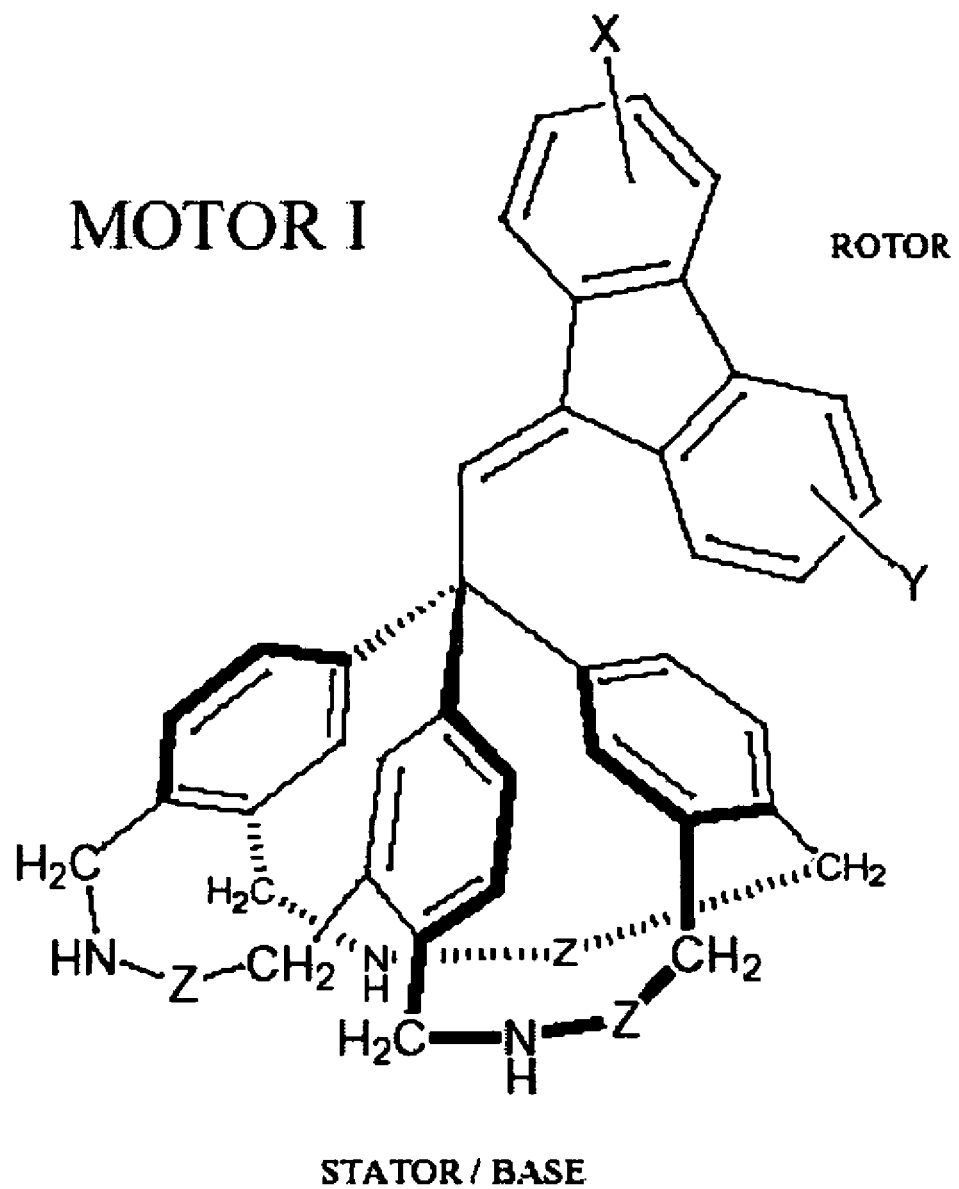
FIG. 1 depicts the structure of an exemplary Motor I.

The invention relates to compounds that function as a molecular motor which can be driven by light to produce directional (clockwise or counterclockwise) motion. The compounds of the invention have the general Formula (1).

$C_b$ is a carbocyclic or heterocyclic group having an atom within the cyclic structure selected from C, N, Si, and Sn and singly bound to A. The group A is CR, COR, CSR, $CNR_2$, CCN, $CCONR_2$, $CNO_2$, CNNAr (wherein Ar is aryl or heteroaryl), CX' (wherein X' is a halide), or N. $C_r$ is a photoactive rotor which has a substantially planar cyclic structure.

More particularly, the invention relates to a compound of formula (2):

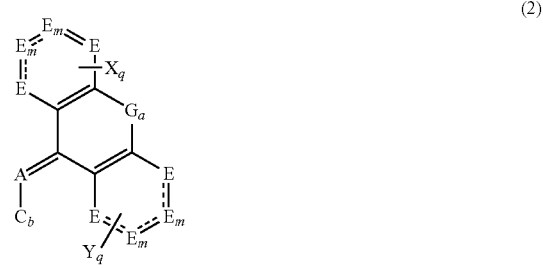

In formula (2), the $C_b$ and A are as defined above. The group G in the central cyclic structure is CR, $CR_2$, C=$CR_2$, C=O, C=S, C=NR, N, NR, O or S with n being 0, 1, or 2. In the two outer cyclic structures E is CH, $CH_2$, N, NH, O, or S and m is 0, 1, 2 or 3. The outer rings may, independently from each other, be substituted with groups X and Y where N is $R^1$, $SiR^1_3$, —$NR^1$, $NR^1_2$, =O, $OR^1$, =S, or $SR^1$; Y is $R^1$, $SiR^1_3$, =$NR^1$, $NR^1_2$, =O, $OR^1$, =S, or $SR^1$; and q is 0, 1, 2, 3, or 4. The groups R and $R^1$ are defined as follows:

R is H;
    substituted or unsubstituted, branched or straight chain $C_1$-$C_{18}$ alkyl;
    substituted or unsubstituted, branched or straight chain $C_2$-$C_{18}$ alkenyl;
    substituted or unsubstituted, branched or straight chain $C_2$-$C_{18}$ alkynyl;
    —($OCH_2CH_2$)$_{1-15}$OH; —($OC_3H_6$)$_{1-15}$OH;

substituted or unsubsituted, saturated or unsaturated, carbocycles or heterocycles; or substituted or unsubsituted aryl or heteroaryl; and $R^1$ is H;

substituted or unsubstituted, branched or straight chain $C_1$-$C_{18}$ alkyl;

substituted or unsubstituted, branched or straight chain $C_2$-$C_{18}$ alkenyl;

substituted or unsubstituted, branched or straight chain $C_2$-$C_{18}$ alkynyl;

—$(OCH_2CH_2)_{1-15}OH$; —$(OC_3H_6)_{1-15}OH$;

substituted or unsubsituted, saturated or unsaturated, fused or unfused carbocycles or heterocycles; or substituted or unsubstituted, fused or unfused aryl or heteroaryl;

wherein when $R^1$ is a cyclic structure the heteroatoms Si, N, O, or S within the definitions of X and Y may form part of the cyclic structure.

Preferred embodiments of each portion of the compounds of the invention are discussed below. Two examples of compounds of the invention are molecular motors I and II, discussed in more detail below.

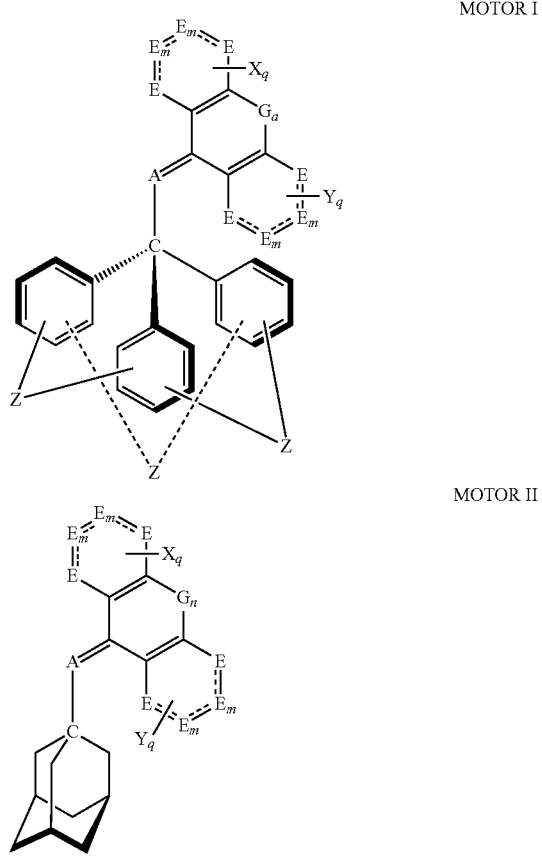

MOTOR I

MOTOR II

Compounds of the invention and their components of molecular motor design may be depicted schematically as shown in FIG. 29. The compounds contain a stator or base, $C_b$, and a photoactive rotor. The stator is similar to a gear in that it contains two or three ridges, or teeth. The rotor contains a planar portion and is canted at an angle as to insert part of this planar portion into one of the spaces between the stator ridges. This interlocking of rotor and stator restricts rotation of the rotor with respect to the stator about the "torque axis."

The rotor portion of compounds of the invention are photoactive moieties, preferably a chromophore, that absorbs light energy and converts it into motion. The photoactive rotor activates the "drive" double bond with A, which may be a part of the photoactive rotor or preferred chromophore. The drive double bond with A and the photoactive rotor twists out of plane in the excited state produced when the rotor absorbs one or more photons (usually one photon). Twisting of the rotor about this "drive axis", is resisted by contact between the rotor and the ridges of the stator, but this resistance is overcome by the force of the light-driven twisting motion of the rotor. Contact with the stator will cause the rotor to move in the opposite direction, producing a net rotation around the torque axis. Twisting of the double bond of the rotor by ca. 90°, allows the motion about the torque angle to carry the rotor over the ridge, whereupon it relaxes back to the planar state in the next or a subsequent space. In preferred compounds the photoactive rotor is selected such that absorption of one photon causes the rotor to move at least one space, causing a 180° rotation about the torque axis when the stator has two ridges or 120° rotation about the torque axis when the stator has three ridges.

In preferred compounds of the invention the atom in the stator $C_b$ bound to A is chiral such that the ridges of the stator are not symmetrical and provide a different degree of resistance to the motion of the rotor, depending on whether this motion is clockwise or counterclockwise. This imparts a preferred sense of rotation about the torque axis; otherwise the light-activated motion of the motor would be non-directional and far less useful. A further and advantageous consequence of the dissymmetry of the stator is that the motor molecule is chiral, hence it can be synthesized in two mirror-image forms. One "enantiomers" will rotate in a clockwise sense and the other in a counterclockwise direction.

This fundamental actuation process and the light driven motor operation of compounds of the invention can be illustrated using a preferred Motor I as an example. A representation of the structure of a preferred Motor I is shown in FIG. 30(a). The structure has two components linked by a C—C single bond: (1) a dibenzofulvene "rotor" and (2) a trityl (triphenylmethane) "stator" base. In its minimum energy conformation, the base has a chiral, three-bladed propeller shape (C3 symmetry) due to the attachments among its phenyl rings. In the unenergized motor, rotation by Φ about the C—C bond is hindered by the gearing of the rotor into one of the three, equivalent gaps between the phenyl ring "propeller-blades", as depicted in the top (FIG. 30(b)) and side (FIG. 30(c)) views of the ball-and-stick models of the structure.

Figure 31:
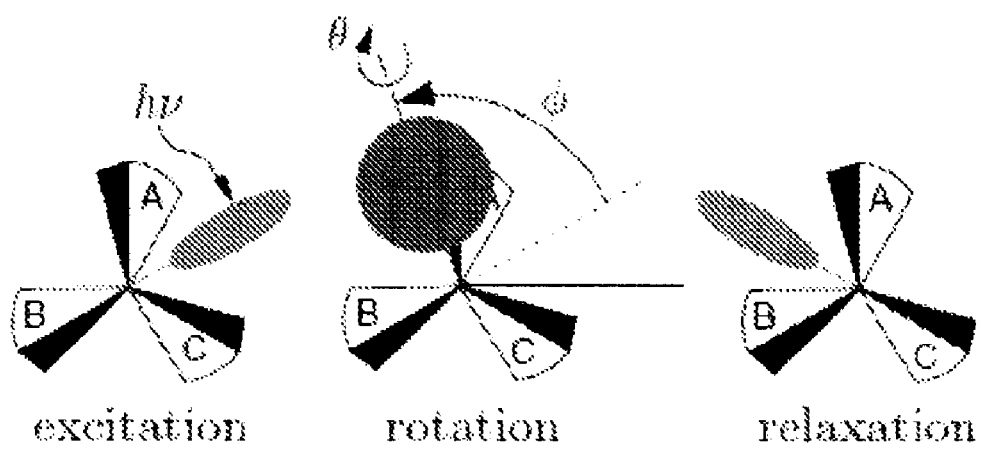
FIG. 31 depicts a cartoon showing one cycle of motor operation as viewed from above the base.

The cartoon in FIG. 31 shows one cycle of motor operation as viewed from above the base. Photoexcitation of the rotor chromophore induces cis-trans isomerization about the exo-double bond of the rotor. The gearing of the rotor into the base couples θ-rotation about the double bond to Φ-rotation about the C—C linkage of the rotor to the base. The direction of the photoisomerization dynamics is biased by the C3 chiral environment of the base. Preferably there is only one sense of rotation about the double bond, generating unidirectional migration of the rotor about Φ. Dissipation of the photon energy into the rotor load, and to vibrational relaxation (thermal loss), causes the rotor to relax into a neighboring gap in the trityl base. Each photon absorption would than induce a θ=180° of the rotor accompanied by a Φ=120° turn relative to the base. Three photoexcitation events result in a return to the original configuration.

As discussed below, both the rotor and the stator can be made with one or more substituent groups, such as, for example, alkyl chains bearing polar or reactive functional groups. This allows the motor to be attached to other molecules or surfaces and enables the chemist to tune physical properties, such as solubility. Moreover, the structures of the stator and rotor can be varied in order to tune the twisting force, efficiency and wavelength of light absorption.

The compounds of the invention being molecular motors are, then, operational analogs of biological rotary motors, but with a number of improved and advantageous performance characteristics: (1) temporal control of actuation by pulsed laser light (including potential cooperative functioning of multiple motors by synchronous excitation), (2) positional control of the motor using polarized light, (3) rotary frequencies potentially up to 100 MHz using intense laser light sources, (4) the ability to synthetically tailor the motor structure to emphasize specific performance characteristics, and (5) chemical functionalization of the motor for selective incorporation into specific sites of a nanostructure. The compounds of the invention are robust over a wide range of thermal and chemical environments, including vacuum.

Compounds of the Invention

Compounds of the invention include of Formula (1):

The group $C_b$ defines the stator or base of the molecular motor. $C_b$ is a carbocyclic or heterocyclic group having an atom within the cyclic structure selected from C, N, Si, and Sn and singly bound to A.

The group A is CR, COR, CSR, $CNR_2$, CCN, $CCONR_2$, $CNO_2$, CNNAr (wherein Ar is aryl or heteroaryl), CX' (wherein X' is a halide), or N.

$C_r$ defines the photoactive rotor and has a substantially planar cyclic structure.

Preferred compounds of the invention are those of formula (2).

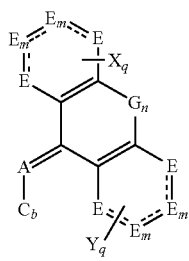

(2)

In the compounds of formula (2) the drive axis is defined by the "drive" double bond between A and the rotor ring structure shown by the three ring structure in formula (2). The torque axis is defined by the single bond between A and the stator, $C_b$. In formula (2) A is is CR, COR, CSR, $CNR_2$, CCN, $CCONR_2$, $CNO_2$, CNNAr (wherein Ar is aryl or heteroaryl), CX' (wherein X' is a halide), or N. Preferably A is CR or N, more preferably CR. In some particularly preferred embodiments A is CH.

The group $C_b$ is a carbocyclic or heterocyclic group having an atom within the cyclic structure selected from C, N, Si, and Sn and singly bound to A. In a preferred embodiment $C_b$ is a tri-cyclic carbocycle or heterocycle where the bridgehead atom is a chiral bridgehead carbon atom bound to A. Exemplary bi-cyclic carbocycles or heterocycles for $C_b$ include but are not limited to bicycloheptene, bicyclooetane, bicyclononane, and bicycloundecane. Exemplary tri-cyclic carbocycles or heterocycles for $C_b$ include but are not limited to triphenylmethane derivatives; adamantane derivatives; tricyclo[2.2.1$^1$]heptane,; tricyclo[5.4.0.0$^{2,9}$]undecene; tricyclo[5.2.2.0$^{4,9}$]dodecane; tricyclo[4.4.1.1$^{1,5}$]dodecane, tricyclo[5.5.1.0$^{5,9}$]tridecane; 9,10-dihydro-9,10-(2'-butylene)anthracene, and tricycle[5.3.1.1$^1$]dodecane. Other possible stators are those shown in structures 1-8 shown below.

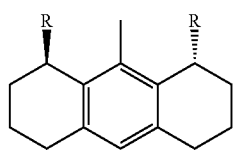

1

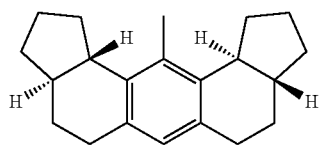

2

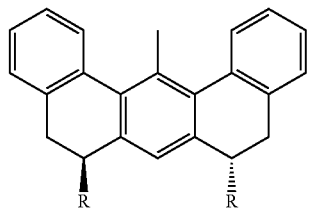

3

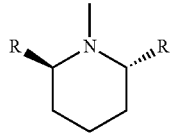

4

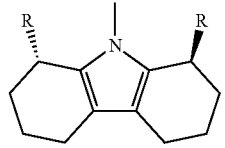

5

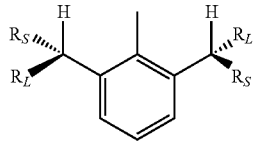

6

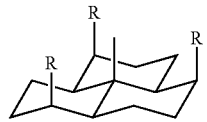

7

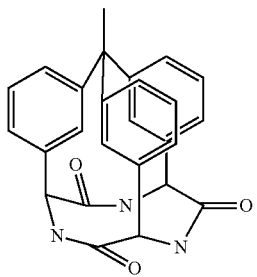

8

Some representative substitution patterns (R) are shown for exemplary stators 1-8 above. Other subsitition patterns, as known in the art, are also possible, for example on other ring atoms such as carbon in each structure or nitrogen in stator 8. Possible substituents include those discussed for the group R below.

The rotor portion of a compound of formula (2) is defined by the moiety:

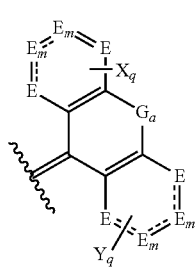

(1a)

In this structure G is CR, CR$_2$, C=CR$_2$, C=O, C=S, C=NR, N, NR, O, or S and n is 0, 1, or 2. When n is 0, the central ring is a cyclopentadienyl ring, when n is 1, the central ring is a six-membered ring, and when n is 2, a seven-membered ring. G, then in a six-membered ring may be CR, CR$_2$, C=CR$_2$, C=O, C=S, C=NR, N, NR, O, or S. In a seven-membered ring, G may be, independently, any of CR, CR$_2$, C=CR$_2$, C=O, C=S, C=NR, N, NR, O, or S. Preferably G is C, CR$_2$, N, or NR and n is 0 or 1. Preferred ring structures of the central ring include cyclopentadienyl, cyclohexyldiene, cyclohexyldienyl, cycloheptadienyl, pyranyl, and dihydropyridyl.

In some embodiments the central ring may be substituted at G, e.g. where G is CR, CR$_2$, C=CR$_2$, C=NR, or NR. The group R is defined as H; substituted or unsubstituted, branched or straight chain C$_1$-C$_{18}$ alkyl; substituted or unsubstituted, branched or straight chain C$_2$-C$_{18}$ alkenyl; substituted or unsubstituted, branched or straight chain C$_2$-C$_{18}$ alkynyl; —(OCH$_2$CH$_2$)$_{1-15}$OH; —(OC$_3$H$_6$)$_{1-15}$OH; substituted or unsubstituted, saturated or unsaturated, carbocycles or heterocycles; or substituted or unsubstituted aryl or heteroaryl. Preferably R is H; substituted or unsubstituted, branched or straight chain C$_1$-C$_9$ alkyl; substituted or unsubstituted, branched or straight chain C$_2$-C$_9$ alkenyl; substituted or unsubstituted, branched or straight chain C$_2$-C$_9$ alkynyl; —(OCH$_2$CH$_2$)$_{1-7}$OH; —(OC$_3$H$_6$)$_{1-7}$OH; substituted or unsubstituted, saturated or unsaturated, carbocycles or heterocycles; or substituted or unsubstituted aryl or heteroaryl.

More preferably R is R is H; substituted or unsubstituted, branched or straight chain C$_1$-C$_5$ alkyl; substituted or unsubstituted, branched or straight chain C$_2$-C$_5$ alkenyl; substituted or unsubstituted, branched or straight chain C$_2$-C$_5$ alkynyl; substituted or unsubsituted, saturated or unsaturated, carbocycle or heterocycle selected from cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and the like including their corresponding iso-forms; or a substituted or unsubstituted fused or unfuesed aryl or heteroaryl selected from phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenathtryl, and the like including their corresponding iso-forms. In some particularly preferred embodiments R is H, methyl, ethyl, propyl, isopropyl, butyl, isobutyl, tert-butyl, cyclopentyl, cyclohexyl, phenyl, pyridinyl, or pyrrolidinyl.

The R groups just discussed, and the groups R$^1$ and Z discussed below, contemplate that the alkyl, alkenyl, alkynyl, carbocycles, and heterocycles may themselves be unsubstituted or substituted. Unsubstituted means the particular moiety carries hydrogen atoms on its constituent atoms, e.g. CH$_3$ for unsubstituted methyl. Substituted means that the group can carry typical functional groups know in organic chemistry. Such functional groups include, but are not limited to, halides, hydroxyl, thiols, amine groups, carboxylic acid groups, ketones, aldehydes, nitriles, nitro, azo, nitroso, ethers, thioethers, amides, etc. The alkyl, alkene, and alkyne groups, as indicated, may be straight chains or branched structures. For unsaturated moieties, e.g. alkenes, alkynes, unsaturated carbocycles, or unsaturated heterocycles, the degree of unsaturation may vary from one unsaturation to the maximum possible within the particular moiety. Unsaturated groups may also have a mixture of double and triple bonds.

In the moiety (Ia), E is CH, CH$_2$, N, NH, O, or S. Preferably E is CH, CH$_2$, N, or NH. The integer m, defining the number of groups E is 0, 1, 2, or 3; preferably 1 or 2; and most preferably 1. In a preferred embodiment, the rings defined by E and the double bond of the central ring may be the same or different ring structures selected from, for example, cyclopentene, cyclopenatdiene, cyclohexene, cyclohexadiene, cycloheptene, cycloheptadiene, phenyl, pyrrole, imidazole, pyrazole, pyridine, pyrazine, pyridazine, furan, pyran, thiazole, and the like.

The rings defined by the groups E and the double bond of the central ring may be unsubstituted or substituted by the groups X or Y. Just as the rings themselves may the same or different, the substitution of the rings may be the same or different. In formula (2) X is R$^1$, SiR$^1_3$, =NR$^1$, NR$^1_2$, =O, OR$^1$, =S, or SR$^1$; Y is R$^1$, SiR$^1_3$, =NR$^1$, NR$^1_2$, =O, OR$^1$, =S, or SR$^1$; and q is 0, 1, 2, 3, or 4. In preferred embodiments X is R$^1$, =NR$^1$, NR$^1_2$, =O, OR$^1$, =S, or SR$^1$; Y is R$^1$,=NR$^1$, NR$^1_2$, =O, OR$^1$, =S, or SR$^1$; and q is 0, 1, 2, 3, or 4. More preferably, X is R$^1$, NR$^1_2$, or OR$^1$, or SR$^1$; Y is R$^1$, NR$^1_2$, or OR$^1$; and q is 0, 1, or 2. In further preferred embodiments X is R$^1$, NR$^1_2$, or OR$^1$; Y is R$^1$, NR$^1_2$, or OR$^1$; q is 0, 1, or 2.

As can be seen from their formulae, the groups E may be substituted or unsubstituted the group R$^1$. In formula (2) R$^1$ is H; substituted or unsubstituted, branched or straight chain C$_1$-C$_{12}$ alkyl; substituted or unsubstituted, branched or straight chain C$_2$-C$_{12}$ alkenyl; substituted or unsubstituted, branched or straight chain C$_2$-C$_{12}$ alkynyl; —(OCH$_2$CH$_2$)$_{1-15}$ OH; —(OC$_3$H$_6$)$_{1-15}$OH; substituted or unsubstituted, saturated or unsaturated, fused or unfused carbocycles or eterocycles; or substituted or unsubstituted, fused or unfused aryl or heteroaryl. In all embodiments of $R^1$ when $R^1$ is a cyclic structure the heteroatoms Si, N, O, or S within the definitions of X and Y may form part of the cyclic structure. Preferably $R^1$ is H; substituted or unsubstituted, branched or straight chain $C_1$-$C_9$ alkyl; substituted or unsubstituted, branched or straight chain $C_2$-$C_9$ alkenyl; substituted or unsubstituted, branched or straight chain $C_2C_9$ alkynyl; —$(OCH_2CH_2)_{1-7}$OH; —$(OC_3H_6)_{1-7}$OH; substituted or unsubsituted, saturated or unsaturated, fused or unfused carbocycles or heterocycles; or substituted or unsubstituted, fused or unfused aryl or heteroaryl. More preferably $R^1$ is H; substituted or unsubstituted, branched or straight chain $C_1$-$C_4$ alkyl; substituted or unsubstituted, branched or straight chain $C_2$-$C_4$ alkenyl; substituted or unsubstituted, branched or straight chain $C_2$-$C_4$ alkynyl; substituted or unsubsituted, saturated or unsaturated, fused or unfused carbocycles or heterocycles selected from cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and the like including their corresponding iso-forms; or a substituted or unsubstituted fused or unfuesed aryl or heteroaryl selected from phenyl, benzyl, naphthyl, furyl, benzofuranyl, pyranyl, pyrazinyl, thienyl, pyrrolyl, imidazolyl, pyridyl. Pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenathtryl, and the like including their corresponding iso-forms. In some particularly preferred embodiments, $R^1$ is H, methyl, ethyl, propyl, isopropyl, butyl, isobutyl, tert-butyl, cyclopentyl, cyclohexyl, phenyl, or pyridinyl, pyrrolidinyl or a cyclic structure such as, e.g. benzofuran, benzothiophene, indole, indazole, indolizine, quinoline, phthalazine, napththyridine, quinoxaline, quinazoline, and cinnoline.

Figure 14:
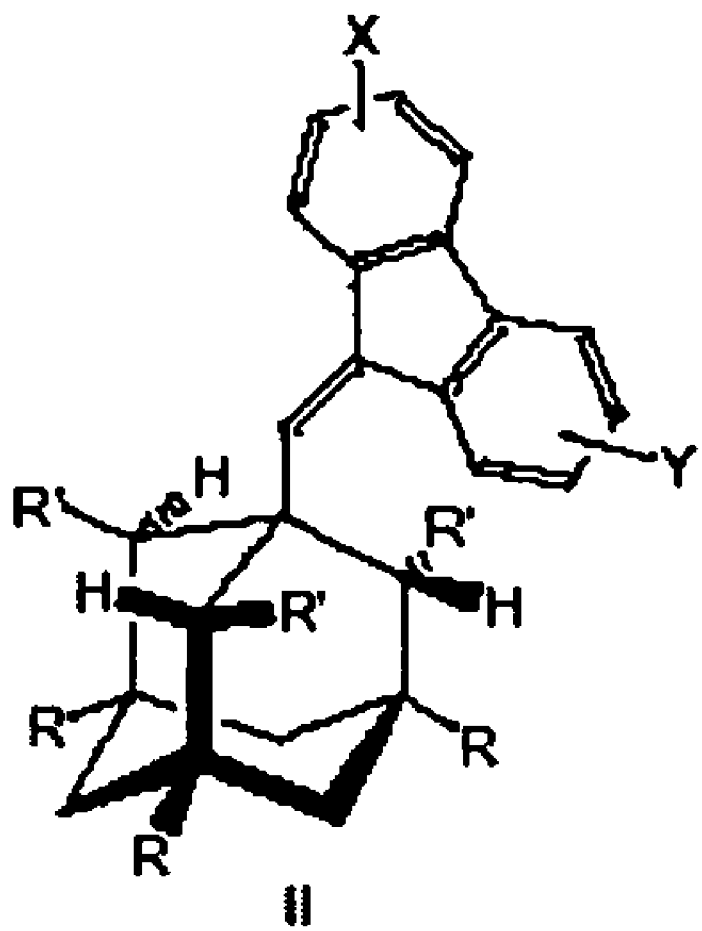
FIG. 14 depicts the structure of an exemplary Motor II.
Figure 15:
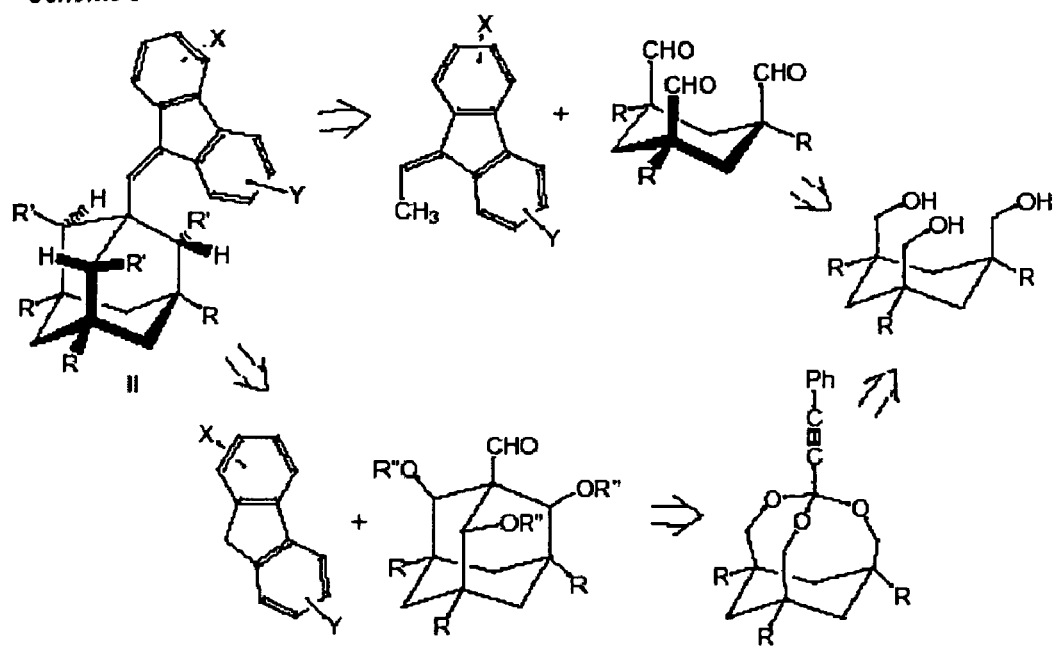
FIG. 15 depicts Scheme 8, a retrosynthetic scheme for an exemplary Motor II.

Preferred compounds of formula (2) have the moiety of formula (Ia) selected from 4H-cyclopenta-[def]phenanthrene, 7H-dibenzo[c,g]fluorene, 13H-dibenzo[a,i]fluorene, 13H-dibenzo[a,g]fluorene, 11H-benzo[a]fluorene, 7H-benzo[c]fluorene, derivatives of hexafulvenes and heptafulvenes. Such chromophores contain a photoactive, drive double which includes group A, or are attached to and activate the double bond in formula (2). The photoactive bond in the chromophore may be a C=C, C=N or N=N bond. The active, drive double bond shown in FIGS. 1 and 14 are trisubstituted. Additional, tetrasubstitution of a photoactive double bond in the chromophore could be used to further tune the mechanical, optical, and photochemical properties of a molecular motor according to the invention.

As discussed above, preferred compounds of the invention have the general formulas Motor I and Motor II. The various groups within these structures are the same as those discussed above, including the preferred embodiments.

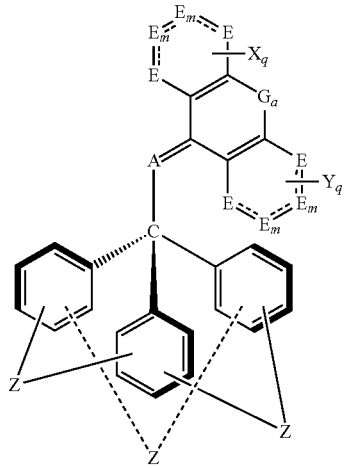

MOTOR I

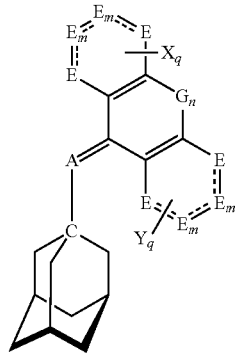

MOTOR II

In compounds having the structural formula of Motor I, the group Z is a divalent group linking the phenyl rings of the stator. The group Z may be substituted or unsubstituted, branched or straight chain $C_3$-$C_9$ alkylene; substituted or unsubstituted, branched or straight chain $C_3$-$C_9$ alkenylene; substituted or unsubstituted, branched or straight chain $C_3$-$C_9$ alkynylene; —$(OCH_2CH_2)_{1-3}O$—; —$(OC_3H_6)_{1-3}O$—; substituted or unsubsituted, saturated or unsaturated, divalent carbocycles or heterocycles; or substituted or unsubstituted arylene or heteroarylene. Preferred groups Z include but are not limited to —$(CH_2)_{4-6}$—, —$CH_2NCH_2C\equiv CCH_2$—, or —$CH_2C\equiv CC\equiv CCH_2$—. The phenyl groups forming the stator in Motor I may be independently substituted with groups X and Y, discussed above. In a preferred embodiment, the atom of the stator bound to A is a carbon.

For compounds of the invention having the structural formula of Motor II, the atom of the stator $C_b$ bound to A is also preferably a carobon. The adamantyl structure may also be substituted with groups X and Y, discussed above.

Molecular Motors

The compounds of the invention with their molecular motor functionality can be used, for example, to drive nanoscale gears, to power nanoscale machines, to propel swimming molecules or devices, to agitate or stir molecules in surface diffusion chemistry, to wind or unwind DNA or other molecules, to make light-triggered capsules capable of releasing drugs, toxins or molecular probes, and to encode information in the orientation of a rotor or patterns of ensembles of rotors adsorbed to a surface.

Optical Control Biomolecule Structure and Activity

The function of DNA is defined by its structure. For example, most genes in the genome are "packaged" into a structure that is not copied by the cell machinery to produce proteins. One feature of these inactive structures is supercoiling. Activation of gene expression requires that the DNA be in an accessible structural form. Other reactions such as degradation in the cell are also controlled by the structure of DNA/RNA. Incorporating of the light-activated motor into duplex DNA (or RNA) allows for optical control of DNA structure, thereby permitting optical control of gene expression in vitro and in vivo. As an example, counter-rotating molecular motors with different absorption wavelengths integrated into a single DNA plasmid could be used to controllably twist and untwist the supercoiling of the plasmid. Use of two motors of apposite chirality, and therefore opposite rotation, could be used in concert to twist or untwist DNA. The same approach can be used for optical control the structure of a protein. As an example, proteins with incorporated motors could be directed to certain areas of the body and activated/deactivated by irradiation with light of a safe wavelength that does not destroy native macromolecules.

The compounds of the invention may also be used to generate and control the motion of or transport two molecules relative to one another. This is particularly useful with two biomolecules or biomolecule/organic molecule combinations. On molecule may be attached (via chemical bonding, e.g. covalent or ionic bonds; by associative bonding, e.g, dipole interactions, hydrogen bonding, or Van der Waals inreactions; or by physical interaction) to the rotor or stator of the molecule. The rotation of the molecular motor can then bring the molecules together or move them apart.

Compounds of the invention may also be used to change catalytic activity of a enzyme. A compound of the invention is attached to an enzyme. Changing conformation of the motor by light activation changes steric access, electrostatic surface potentials, and/or orientational access of a substrate to the enzyme active site thereby changing the catalytic activity of the enzyme. Advantageously, using a compound, or motor, with unidirectional motion is not required and motors with only two positions operate to control the enzyme's catalytic activity.

Light Controlled Pharmaceuticals and Catalytic Structures

The "optical control" properties of the compounds of the invention can used in molecule-frame positioning applications. The molecular motor's rotor can be used as a switchable gateway allowing molecules to diffuse into or out of a nanoscale structure. As an example, the gateway could trap toxins or release drugs sequestered within a motor-functionalized cyclodextrin molecule—a cyclodextrin having a compound of the invention attached. Such light-switchable drugs could be activated in vivo at a targeted location by irradiation with activating light of the proper wavelength. The cyclodextrins could be pre-loaded with a pharmaceutical in a solution with a high drug concentration and under light irradiation. The cyclodextrin molecules, containing an encapsulated drug, are then isolated. The pharmaceutical could be released later, perhaps in vivo, with the light controlling the release directed by a fiber optic onto a targeted organ. An application could be to release a toxin (e.g. a chemotherapy drug) with high local concentration.

Microfluidics

The interaction of molecular rotors and propellers with fluids has been considered in the literature.[53,108,109] Vacek and Miller[53] theoretically modeled driving the motion of a molecular propeller consisting of a phenanthroline type ligand by means of the directed flow of a rare gas, such as helium. Under most of the modeling conditions, propeller rotation was achieved. "Molecular submarines" based on driving fluid flow by means of such propellers has also been envisioned, and photophoresis involving optical generation of a concentration gradient has also been examined theoretically.[108] In this case, the propeller was composed of two naphthalene rings and the fluid was supercritical $CO_2$. It was concluded that it would be feasible to generate molecular torque by means of illumination with rotating polarized light, and that interaction with the fluid would produce forward thrust, resulting in photophoresis.

Various groups and side chains cart be attached to the stator and rotor of compounds of the invention in order to create nanoscale swimmer and stir-bar activity. For example, attaching a bulky carboxylic acid, such as the steroid cholic acid, to the dibenzofulvene rotor via the X and Y groups shown in FIG. 5: Scheme 4. The solvent drag would cause the rotor to act as a "stator" and the $C_3$ symmetric base as a propeller. Under continuous light activation the constant rotation of the propeller could create sufficient thrust (either forward or backward depending upon the enantiomer) to propel this molecule through the fluid. Additional substituents could be added to the propeller (base) to increase thrust swimming efficiency.

By irradiating a sample solution with laser light so that there is a gradient of optical energy density, the swimming molecules will tend to move away from high energy density regions and become stalled in dark regions. This creates a light induced concentration gradient. The magnitude of the gradient can be controlled using light intensity, rotor absorbance characteristics, and solvent viscosity.

Compounds of the invention may also be used to change the surface tension of a liquid flowing over a surface or stir the fluid at the surface. The molecules may be attached (by adsorption, chemical bonding, associative bonding, or physical interaction) to the surface. Activating the molecular motor then creates motion below the fluid surface and decreases surface tension. That motion also stirs the fluid at the surface to which the compound is attached.

The synchronized, collective actuation of monolayers of surface-adsorbed motors to act as molecular-scale stirrers or agitators to alter surface diffusion rates. The stir bars could be used in microfluidics to control or disrupt laminar flow. An array of many adsorbed motors around relatively large, circular gears to be synchronously energized by laser excitation could be used to amplify the mechanical energy of the motors. Multiple motors arrayed along channels could create microfluidic translational motion.

Energized Surfaces and Patterned Surface Structures

Positional control of the rotor chromophore using polarized light can be used to create sub-monolayers of motors positioned in selected patterns, or excited synchronously. The ability to orient the rotor of one or more motors along a selected direction of the surface allows very high density information encoding. If an ensemble of motor molecules is adsorbed to a surface, the anisotropic interaction of the rotor chromophore with polarized exciting light allows selective excitation of motion of rotors oriented in specific directions. Therefore a polarized laser can encode information in the spatial pattern of rotor orientations. The information could be read out later using know techniques, for example, using polarized fluorescence or absorption.

Creating Holes in Membranes

Attaching compounds of the invention to or embedding them in a membrane creates a point of insertion or the ability to make a hole in the membrane at the location of the compound. For example, light activated motion of a rotor embedded in a lipid bilayer will increase the disorder of the membrane. A compound, or motor, of the invention with unidirectional motion is not required. Motors with only two positions may be used. Changes in membrane disorder will alter access of various molecules through the membrane. In the cellular environment, compounds of the invention may be used to disrupt the cellular membrane uses to allow access of pharmaceuticals through membrane. For example, application to skin cells allows controlled access of drug to the underlying fat and muscle layers. The compounds of the invention can be targeted to selective membrane layers by use of antibody coupling.

Preparation of Compounds

The compounds of the invention may be prepared according to a general synthetic procedure. As described in the examples below the rotor and stator portions may be separately prepared. The rotor and stator are then coupled together (e.g. by nucleophilic or eletrophilic substitution at the bridgehead carbon) to form the compound. Alternatively, precursors of the rotor and/or base may be coupled followed by completion of the rotor and/or base. In general a synthetic scheme can be prepared for a given compound by simple retrosynthetic analysis. Use of retrosynthetic analysis also demonstrates other variations which may be introduced into the compounds.

The compounds of the invention may be synthesized using methods well known in synthetic organic chemistry. During the synthesis of the compounds, the functional groups may be protected by known blocking groups to prevent unwanted cross reaction. See, for example, March, "ADVANCED ORGANIC CHEMISTRY, Reactions, Mechanisms, and Structure" 4$^{th}$ Ed., John Wiley & Sons, New York, 1992. Starting materials used in any of these methods are commercially available from chemical vendors such as Aldrich, Sigma, Fluka, and the like, or may be readily synthesized by known procedures. Reactions are carried out in standard laboratory glassware and reaction vessels under reaction conditions of standard temperature and pressure, except where otherwise indicated. The reaction products are isolated and purified by conventional methods, typically by solvent extraction into a compatible solvent. The products may be further purified by column chromatography or other appropriate methods.

EXAMPLES

The invention encompasses many possible molecular structures. Two preferred examples are given here for structures of Motor I and Motor II. Both examples utilize rotors based on the dibenzofulvene (9-fluorenylidene) chromophore.

Example 1

Synthesis of a Preferred Motor I

The stator in a preferred Motor I (see FIG. 1) consists of a triphenylmethane (trityl) group in which the three phenyl rings are linked together by three identical bridges ($CH_2NHZCH_2$). These bridges are attached to the phenyl rings in such a manner as to cause each ring to tilt. The resulting stator assembly adopts the shape of a three-bladed propeller. One end of the rotor is inserted into one of the grooves, or clefts, formed by two adjacent tilted phenyl blades.

The rotor and stator components of Motor I may bear additional substituents or be fused to additional rings so as to produce a stable molecular structure. Some modifications may be useful for the purpose of tuning the physical and chemical properties of the motor. For example, groups X and Y on the rotor may be polar (electron donating or withdrawing) substituents capable of altering the light absorption wavelength, excited state lifetime and twisting efficiency of the chromophore. Fused aromatic rings may be used to similar effect. Fused rings of any type and substituents of various sizes may be used to modify the effective size of the rotor and the energy required for changing its position in the three clefts of the stator.

The tilt of the three phenyl rings, and the depth of the clefts between them, is controlled by the length of the bridge, which is determined by the identity of group Z. Z consists of a chain of 1-6 atoms, preferably 2-3 carbons. The $CH_2$ and NH groups of the bridge may also be replaced by other atoms or groups (e.g. O, S, NR, or $SiR_2$) and the bridge may contain multiply bonded functional groups (e.g. alkene or alkyne). R is defined as an alkyl group or functionalized alkyl chain.

Some substitutions may be useful for the purpose of attaching the motor to other molecules or surfaces in order to harness its motion. In water, the three NH groups of the bridges are protonated and the resulting $NH_2^+$ groups form a tricationic tripod capable of electrostatically attaching the stator to anionic surfaces, such as mica or glass. The H atom of each NH group may be replaced by a functionalized alkyl chain or a silyl group for the purpose of binding the stator to other molecules or surfaces by covalent, electrostatic, hydrogen bonding or dispersion forces. The X and Y groups of the rotor may be alkyl chains bearing functional groups for covalent attachment of the rotor to other molecules and surfaces or for inserting the motor (via both rotor and stator) into biomolecules (e.g. DNA or proteins) or into synthetic polymers.

The synthetic plan for both examples includes several desirable features: (1) a small number of steps; (2) ability to tune the light absorption and emission characteristics of the rotor by varying chromophore structure and substitution; (3) ability to tune the ground state rotational barrier by varying substituents on the base or rotor, as well as the linkage (Z) in the base; and (4) ability to attach tethers to the base and rotor (two each), including differentiation of the base and rotor tethers.

Figure 2:
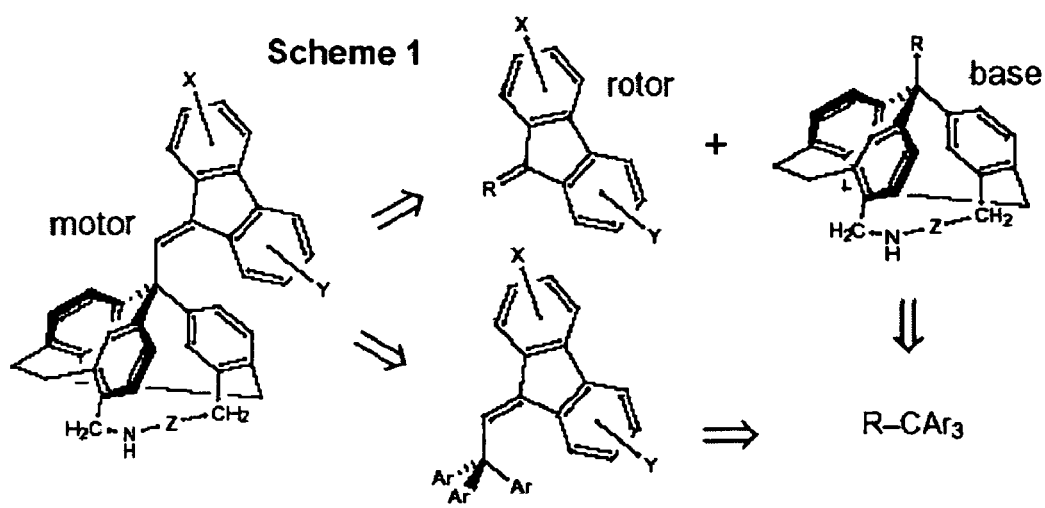
FIG. 2 depicts Scheme 1, a retrosynthetic scheme for an exemplary Motor I.

The simple retrosynthetic analysis for Motor I presented in FIG. 2: Scheme 1 shows two general methods for motor assembly involving different sequences of forming the C3-symmetric base and coupling the rotor to the base or to the triarylmethane precursor to the base. The upper approach in FIG. 2: Scheme 1 involving coupling of the rotor to the preformed base is more convergent and avoids potential side reactions of the rotor or rotor substituents during linkage of the three aryl groups to form the base. On the other hand, coupling of the rotor to the base will produce significant steric strain and higher yields are expected for coupling the rotor to a flexible triarylmethane, as shown in the lower part of FIG. 2: Scheme 1. Accordingly, the synthetic methods allow for both variations.

Figure 3:
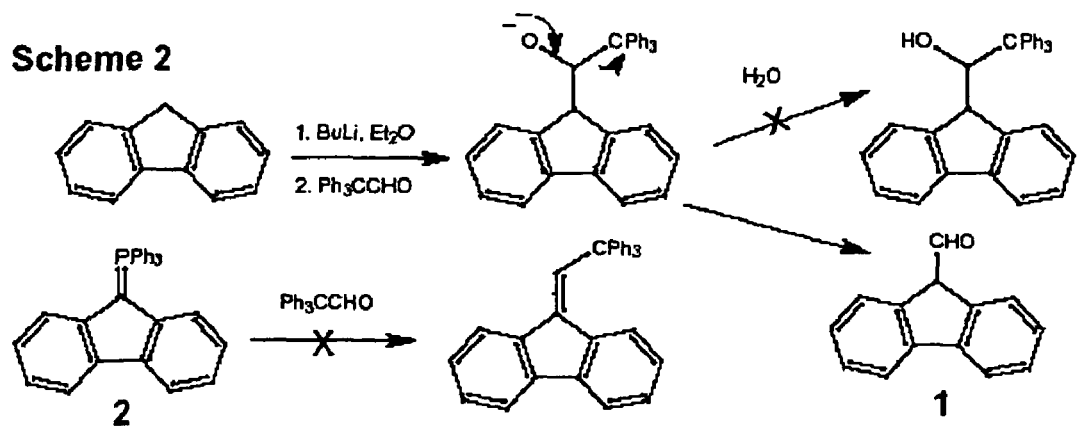
FIG. 3 depicts Scheme 2, the Wittig reaction synthesis of fluorene derivative.
Figure 4:
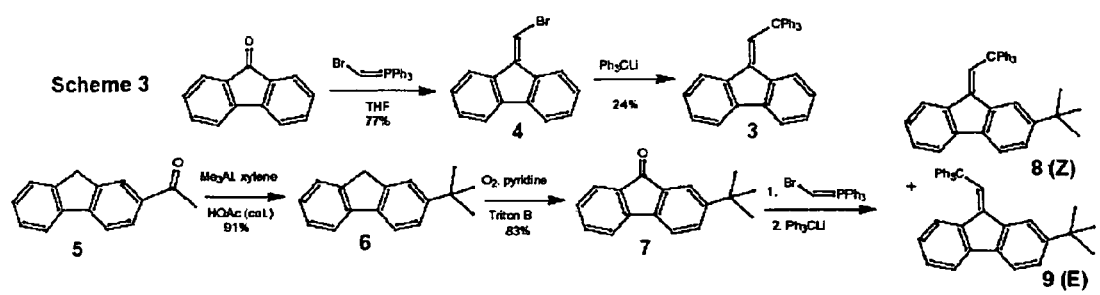
FIG. 4 depicts Scheme 3, the coupling of 9-(bromomethylene)fluorine to carbanions.

Both approaches shown in FIG. 2: Scheme 1 require a practical method for coupling the rotor to the base or flexible base precursor. We have shown in our attempts to produce model compound 3 [9-(2,2,2-tri-phenyl)ethylidenefluorene—FIG. 4: Scheme 3] by adapting the synthetic approach recently used to create 9-(2,2-diphenyl)ethylidene fluorene,[56,57] and by attempting the reaction of Wittig reagent, 2,[58,59] that the most straightforward synthetic approaches are unsuccessful. The former approach suffers from fragmentation of the fluorenyllithium/triphenylacetaldehyde adduct to tritylithium and aldehyde 1, while the Wittig attempt results in no reaction or decomposition under forcing conditions (FIG. 3: Scheme 2). However, 3 can be prepared by means of a recent approach for coupling 9-(bromomethylene)-fluorene to carbanions,[60] as shown in FIG. 4: Scheme 3. Reaction of fluorenone with bromomethylenetriphenylphosphorane gave 4, which was treated with trityllithium in THF at −78° C. The reaction mixture was warmed to 25° C. and quenched with water, then the crude product was purified by column chromatography and recrystallization. Analytically pure 3 is obtained in 24% yield from a relatively large scale (1-2 g), unoptimized reaction. The structure of model compound 3 has been confirmed by X-ray crystallography.

An example of how substituents can be introduced onto the fluorine rotor is shown in FIG. 4: Scheme 3. Here, a t-butyl group was added to desymmetrize the fluorene rotor of 3 in order to investigate photoisomerization. The 2- and 7-positions of fluorene are most reactive toward electrophilic aromatic substitution, and both 2-methylfluorene[62,63] and 2-t-butylfluorene[64] have been prepared. The latter was chosen in anticipation that the larger group would facilitate separation of Z and E isomers by chromatography or crystallization. Air oxidation of 2-t-butylfluorene 6 to 2-t-butylfluorenone 7 under basic conditions[57] is a general method that can be used to synthesize a variety of substituted rotors. Wittig reaction of 7 gives a mixture of Z and E 9-bromomethylene isomers, which is directly treated with trityllithium. The resulting mixture is separated by column chromatography and recrystallization. Pure samples of 8 and 9 are obtained.

Figure 5:
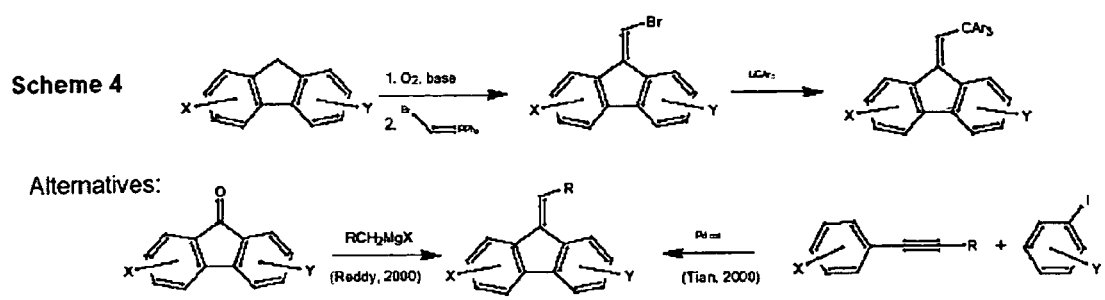
FIG. 5 depicts Scheme 4, a synthesis of fluorene rotors with various substituents.

The Wittig method shown in FIG. 4: Scheme 3 can be used for coupling the rotor with the base. This method can be applied to the synthesis of various motors with having rotors bearing X and Y substituents, as shown in FIG. 5: Scheme 4. Also shown in FIG. 5: Scheme 4 are two alternative methods that are useful for introducing substituted and unsubstituted rotors in certain cases.[65,66] Linkage of the three aryl groups to form the C3-symmetric base presents a significant synthetic challenge. The propyne linkage (Z=CH$_2$C≡C in Scheme 1) is preferred because: (1) modeling studies showed that this produces a relatively large steric barrier for rotor rotation; (2) the resulting 14-membered rings are relatively unstrained and contain three rigid groups, reducing the entropy barrier to cyclization; (3) of the two possible modes of cyclization, reaction of the groups attached to the same ring is very unlikely because it would produce a strained, 8-membered ring containing a triple bond; and, (4) the linkage can be attached via substitution reactions at the benzylic sites or via attack of an amine nucleophile at an aldehyde carbonyl group (reductive amination), all of which appear to be stereoelectronically feasible intramolecular (cyclization) reactions. Note that the conformational constraint imposed by the first 14-membered ring causes the remaining groups on the two aromatic rings to diverge, favoring reaction with the third aromatic ring and formation of the correct product.

Figure 6:
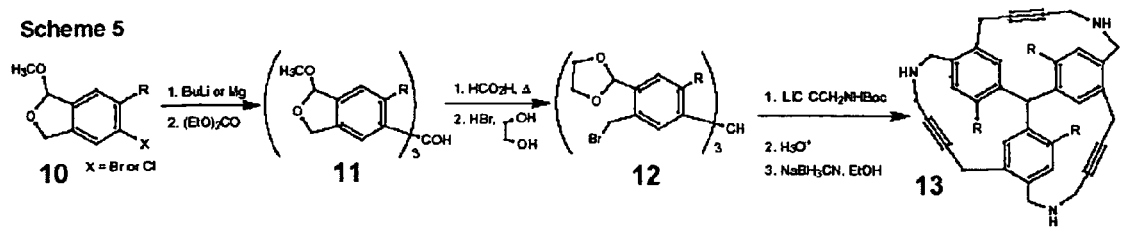
FIG. 6 depicts Scheme 5, a synthesis of triaryl base in an exemplary Motor I.
Figure 7:
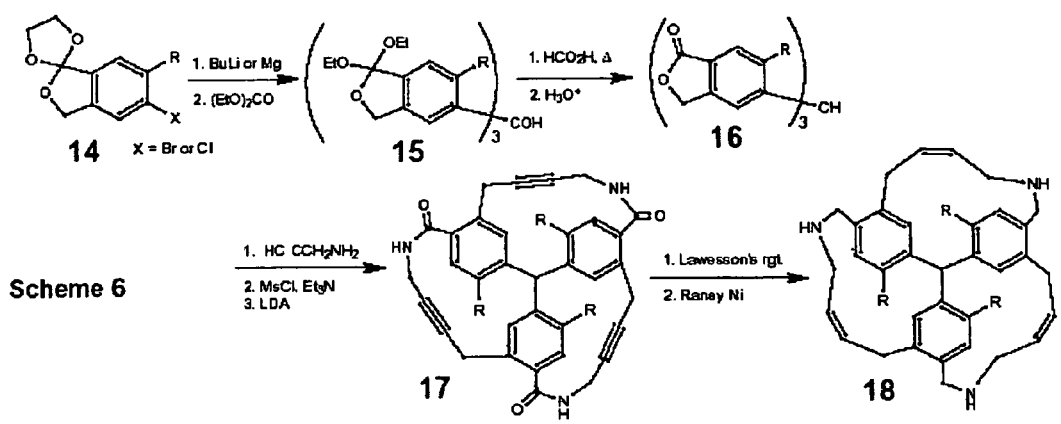
FIG. 7 depicts Scheme 6, an alternate synthesis of triaryl base in an exemplary Motor I.
Figure 8:
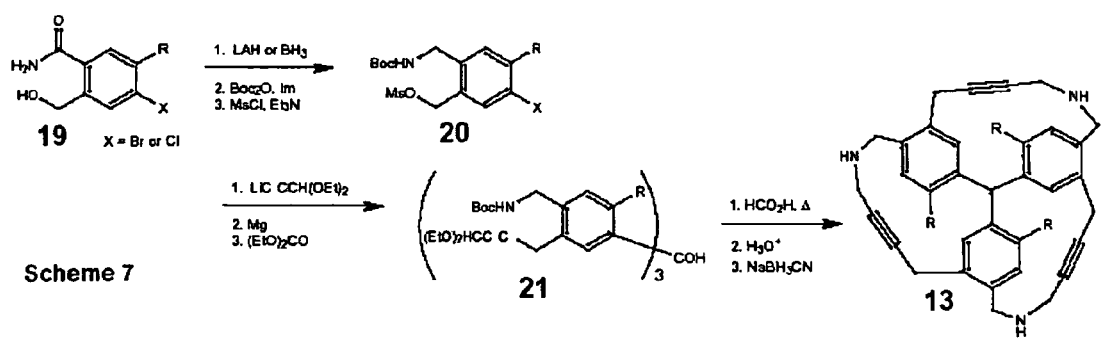
FIG. 8 depicts Scheme 7, an alternate synthesis of triaryl base in an exemplary Motor I.

There are three different synthetic approaches (FIGS. 6-8: Schemes 5-7), each involving the formation of a different bond in the cyclization step. All three employ 5-bromo-[67,68] or 5-chloro-1(3H)-isobenzofuranone[69] as a starting material. Although it requires an extra step for its preparation, the bromide route is preferred because of the relative ease of metal-halogen exchange with butyllithium. Moreover, the formation of hindered triarylmethanol derivatives has been established by reaction of aryllithium reagents with diethylcarbonate.[70] All three approaches allow for incorporation of an ortho substituent (R) and are illustrated in the parent case (R=H).

The base linkage approach shown in FIG. 6: Scheme 5 is preferred because it involves fewer steps than the complementary routes in FIGS. 7 and 8: Schemes 6 and 7. Acetal 10 is prepared by DIBAH reduction of 5-bromo-1(3H)-isobenzofuranone, followed by reaction of the resulting lactol with methanol under acidic conditions.[71] Triarylcarbinol 11 is reduced by means of formic acid,[72] and the resulting triarylmethane can be deprotonated and coupled to the rotor unit (e.g., 4) or converted to 12 with HBr and ethylene glycol. Reaction of 12 with the lithium derivative 73 of Boc-protected propargyl amine[74,75] and hydrolytic deprotection of the amine and aldehyde fucntionalities pave the way for cyclization by reductive amination. Both sodium cyanoborohydride[76] and NaBH$_3$CN/acetic acid[77] have been used to carry out cyclizations by intramolecular reductive amination.

Two alternative base linkage approaches (FIGS. 7 and 8: Schemes 6 and 7) have been devised in ease of difficulties with the shorter route (FIG. 6: Scheme 5). Diethylorthoester derivative 14 (FIG. 7: Scheme 6) is prepared by reaction of the lactone with triethyloxonium tetra°uoroborate, followed by sodium ethoxide,[78] and hydroxyamide 19 (FIG. 8: Scheme 7) is prepared by reaction of the lactone with ammonia. The amide link in 17 may be converted to the thiocarbonyl derivative with Lawesson's reagent.[79,80] Desulfurization and acetylene reduction 80 to 18 is possible, or amide 17 can be N-alkylated to attach tethers for DNA incorporation. One or two of the base nitrogens is alkylated or acylated to provide the asymmetric motor needed to prove motor function in solution. If atropisomers of this type cannot be separated, the base synthesis (FIGS. 6-8; Schemes 5-7) can be modified to add a substituent to one of the three aryl rings.

The fluorene rotor is coupled to the base via intermediate 4 in the first motor synthesis. Various substituted and more highly conjugated fluorenes can be incorporated to increase the steric barrier, to attach tethers or to increase absorption/emission wavelengths. Hindered rotors can be prepared from 1,8-dimethylfluorenone[81,82] or 1,8-dimethoxyfluorene.[83] The 4H-cyclopenta[d,e,f]phenanthrene rotor[84,85] increase wavelength, while the 13H-dibenzo-[a,i]fluoren-13-ylidene rotor[84,85] also increases steric interaction with the base. Tethers are attached to the rotor for DNA incorporation using 3,5-dimethoxyfluorenone[86] as a starting material. Demethylation (HBr or BBr$_3$) followed by alkylation with protected primary aminoalkyl groups gives the requisite diamino functionalization. This approach can also be used to incorporate short polyether (PEG) or polar peptide fragments, to improve water solubility during ligation to DNA or other polar molecules or surfaces.

Example 2

Synthesis of a Preferred Motor I and Fluorene Rotor Derivatives

Figure 9:
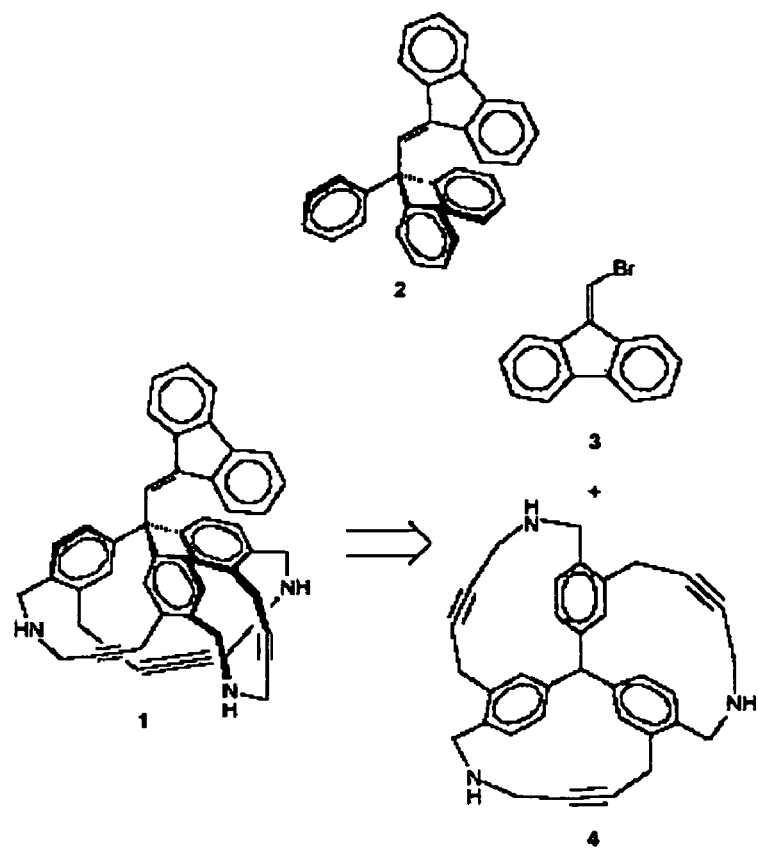
FIG. 9 depicts a retrosynthetic analysis of a molecular motor I in Example 2.
Figure 10:
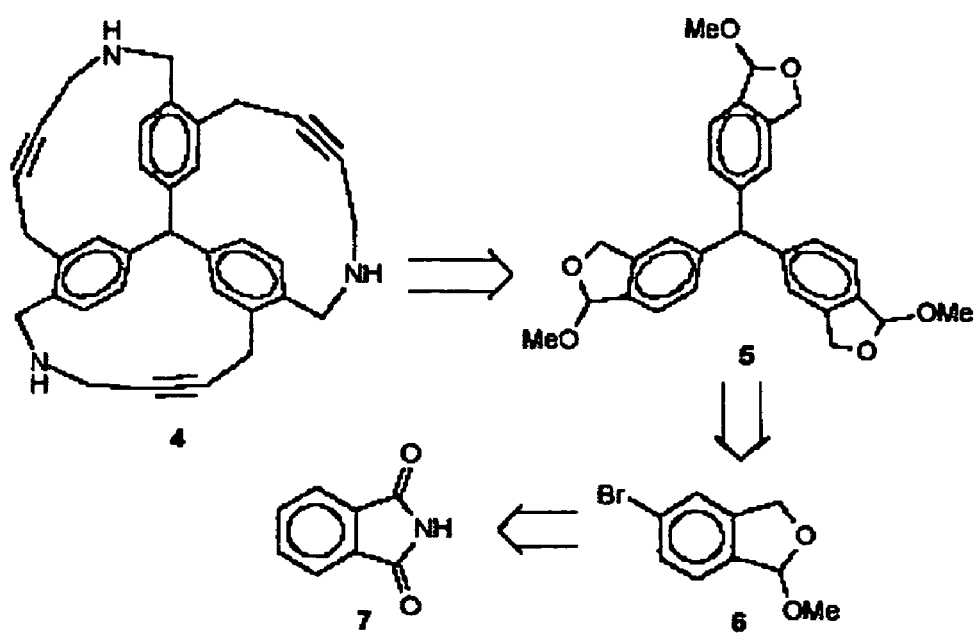
FIG. 10 depicts a retrosynthetic analysis of base unit 4 in Example 2.

A preferred compound having the structure of Motor I, (1) consists of an unsubstituted dibenzofulvene unit, and the base (stator) is a triphenylmethane in which the three-fold propeller shape is enforced by bridges containing a nitrogen atom and a C—C triple bond. FIG. 9 shows a retrosynthetic approach, which is based on the synthesis of 9-(2,2,2)-triphenylethylidenefluorene (2).[1] A key disconnection corresponds to substitution of bromide in 9-bromomethylene-fluorene (3) with a triarylmethane anion derived from triamine 4. The amino groups may need to be protected as amide or silane derivatives during this substitution reactions and during the synthesis of intermediate 4. These amino groups provide anchor points for immobilizing the final motor on surfaces and incorporating it into DNA. The fluorene rotor will also need to be substituted in order to attach oligonucleotide strands and to tune the photophysical properties of this drive unit.

The retrosynthetic analysis of intermediate 4 is shown in FIG. 14. According to this approach, the amino groups are selectively attached to the para position of each phenyl ring of the triphenylmethane unit by reductive amination of the masked aldehyde groups in intermediate 5. The final cyclization step involves three-fold SN2 substitution on the meta benzylic positions by acetylide nucleophiles. Intermediate 5 is derived from 6 by metalation (Li or Mg) and reaction with dimethyl carbonate. Bromoacetal 6 is, in turn, derived from phthalimide (7) in several steps by reactions that are either already known or are analogous to transformations reported in the literature.

Figure 11:
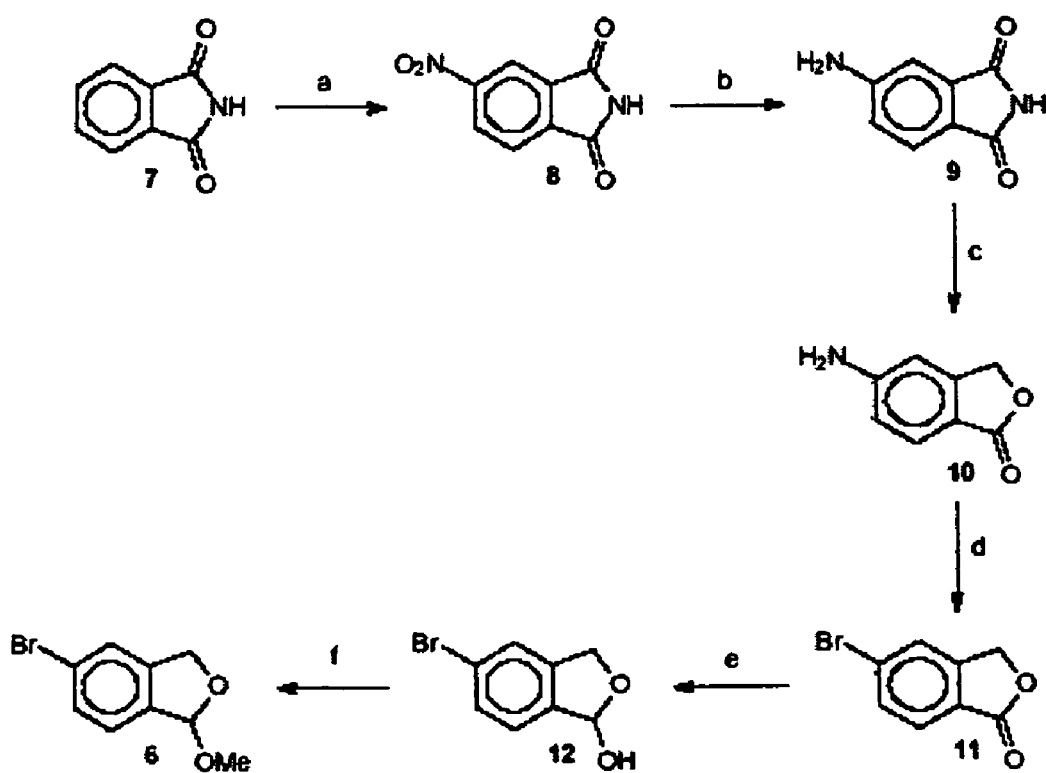
FIG. 11 depicts the synthesis of Intermediate 6 in Example 2.

The synthesis of bromoacetal 6 from phthalimide (7) is shown in FIG. 11. Based on reactions described in the literature, these transformations were carried out on large scale, and some steps were improved. Nitration of 200 g of phthalimide (7) gives 146 g of 5-nitrophthalimide (8). Reduction of 8 by catalytic hydrogenation, according to the literature procedure, is a bottleneck in the synthesis because of the large volume of solvent needed. With a 2 L Parr hydrogenator pressure vessel, 30 g of 8 is convened to 25 g of amine 9. The next step is also a reduction; aminophthalide 10 is obtained quantitatively from 9 by copper-catalyzed reaction with zinc in aqueous base. Steps b and c could be combined by treating 8 with zinc dust and copper(II) sulfate in 2 M aq. sodium hydroxide. This variation, which is not shown in FIG. 11, removes the bottleneck, potentially allowing 100 g of 10 to be prepared in one step from 146 g of 9. The reaction conditions for the steps shown in FIG. 11 are as follows: a) HNO3, H2SO4, 0° C., 56%; b) 5% Pd/C, H2, EtOAc, 97%; c) Zn, CuSO4, 6 M NaOH, 5° C. then heated at 70-80° C. 16 h, 100%; d) NaNO2, 4 M HBr, followed by CuBr at 0° C.; e) DIBAL, toluene, −42° C.; f) BF3·OEt2, MeOH, RT.

Aminophthalide 10 is converted to bromophthalide 11 in 76% yield by means of the Sandmeyer reaction. 36 g of 11 was prepared in one batch. Reduction of 11 with diisobutylaluminum hydride gives bromolactol 12, a novel compound in this series, in 77% yield. Bromoacetal 6 was then prepared in 96% yield by reaction of 12 with boron trifluoride etherate in methanol. 6 was also prepared on a 3 g scale. Overall, the synthesis of 6 shown in Scheme 3 is very effective, because the yields are generally high and only the last two steps (e and f) require chromatography for product purification.

Figure 12:
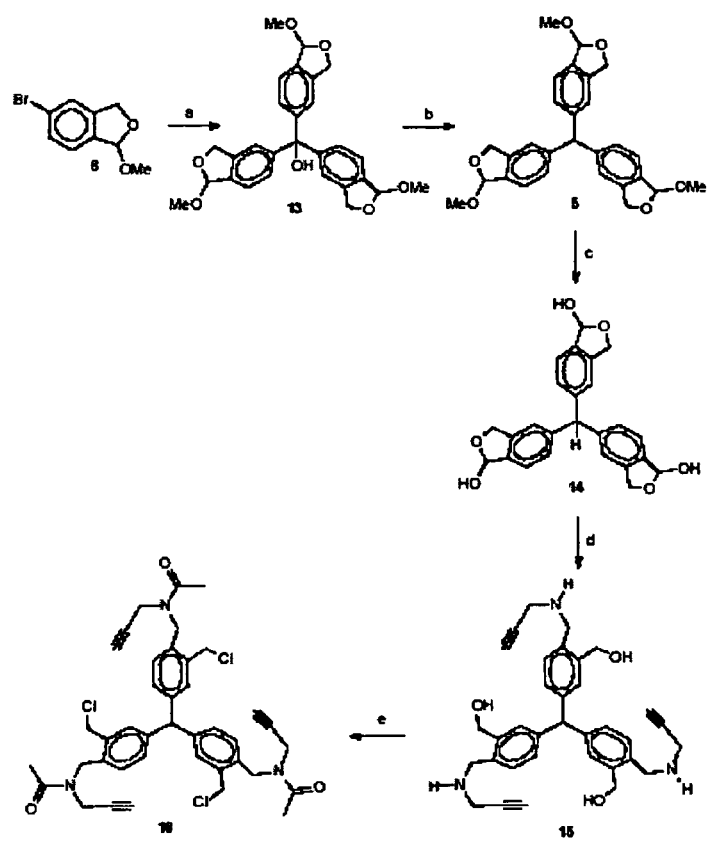
FIG. 12 depicts the synthesis of 16, an immediate precursor to intermediate 4 in Example 2.

The synthesis of trichloride 16, the immediate precursor to target intermediate 4, is shown in FIG. 12. Lithium-bromine exchange of bromoacetal 6 followed by reaction of the resulting aryllithium reagent with dimethyl carbonate gives triarylcarbinol 13 in high yield. Became racemic 6 is used, product 13 consists of a 3:1 ratio of RRS/SSR and RRR/SSS diastereomers, respectively. These isomers were not separated, so subsequent intermediates 5 and 6 also are mixtures of diastereomers, but the stereocenters are destroyed in step d. Reduction of 13 to triarylmethane 5 required careful adjustment of reaction conditions because the hydroxyl group must be converted to a good leaving group without cleavage of the acid-sensitive acetal moieties. This was accomplished in good yield by conversion to the triarylmethyl chloride, then reduction in situ. Hydrolysis of 5 gave tris(lactol) 14, which was converted without purification to tris(aminoalcohol) 15 by reductive amination with propargylamine. Intermediate 15 is very polar, and purification by flash chromatography was easier after complete acetylation with acetic anhydride. Partial hydrolysis gave the corresponding triacetamide triol, which was converted to triacetamide trichloride 16 by mesylation and concomitant displacement of mesylate by chloride. Approximately 300 mg of 16 is typically obtained from one reaction. The reaction conditions for the steps shown in FIG. 12 are as follows: a) t-BuLi, THF, −78° C., the (MeO)2CO −78° C. to RT, 93%; b) SOCl2, NEt3, THF 0° C., then LiAlH4 0° C. to RT, 71%; c) H2SO4, THF (aq); d) i) propargylamine, 4 Å sieves, THF; ii) NaBH4, 1:1 THF/MeOH; e) i) Ac2O, NEt3, CH2Cl2; ii) NH3 (aq), MeOH; iii) MsCl, NEt(l-Pr)2, CH2Cl2.

Figure 13:
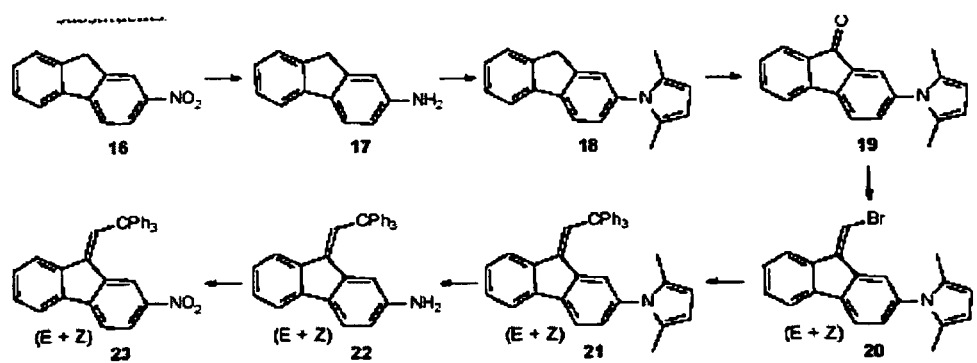
FIG. 13 depicts the synthesis of model compounds with various rotor substituents in Example 2.

To desymmetrize the fluorene rotor 2 in FIG. 9 several derivatives of the fluorine rotor are prepared. FIG. 13 shows the synthesis of compounds with various rotor substituents. Reduction of 2-nitrofluorene with Zn/CaCl2 in ethanol gave 2-aminofluorene (17) in 78% yield. In order to protect the amino group in a 2,5-dimethylpyrrole ring, 17 was condensed in 84% yield with 2,5-hexanedione to produce 18. Ketone 19 was prepared in 65 % yield by bubbling air through a solution of 18 in pyridine containing benzyltrimethylammonium hydroxide. Wittig reaction of 19 with bromomethylene-triphenylphosphorane gave 20 as an E/Z mixture in 72% yield. Reaction of 20 with trityllithium then gave model compound 21. The E and Z isomers of 21 were separated by crystallization and identified by means of their 1H NMR spectra, as well as the X-ray structure of (Z)-21. Deprotecion of the amino group was achieved by treating 21 with hydroxylamine hydrochloride in refluxing ethylene glycol, and a pure sample of the stereoisomer of 22 has been obtained.

Notes for Example 2.

1. "Bond Angle vs. Torsional Deformation in an Overcrowded Alkene: 9-(2,2,2)-Triphenylethylidenefluorene," T. W. Bell, V. J. Catalano, M. G. B. Drew, and D. J. Phillips, *Chem. Eur. J.* 2002, 8, 5001-5006.

Example 3

Synthesis of a Preferred Motor II

The molecular architecture of a preferred Motor II (FIG. 19) features a rigid C3-symmetric adamantane base. Three aryl (e.g., phenyl) or alkyl groups shown as R' in the figure act as the three steric barriers or ridges restricting the rotation of the rotor about the torque angle. The size of this R' group can be adjusted in order to tune the energy required for rotation of the rotor. The three R groups attached to the base can act as "feet" by anchoring it a surface or another molecule. For this purpose, they can be alkyl chains bearing terminal, reactive functional groups. Alternately, they can be used to adjust the polarity and solubility of the motor molecule. Motor II shares the same dibenzofulvene rotor structure with Motor I. In both cases, the rotor and various substituents can be varied, as described for Motor I.

Motor II is a desirable, complementary alternative to Motor I for the following reasons: (1) the C3-symmetric adamantane base of Motor II is a robust, polycyclic carbon skeleton that positions the steric barrier groups (R') more rigidly than the somewhat flexible benzene rings of Motor I; (2) π-electrons in the base of Motor I may cause some UV light absorption and deactivation/dissipation of rotor excitation energy; (3) the phenyl groups in the base of Motor I are allylic with respect to the dibenzofulvene rotor, possibly leading to photochemical di-¼-methane rearrangement that might decrease the long-term stability of the motor when operating under continuous illumination. As for Motor I, there are two different general strategies for Motor II, as shown in the simple retrosynthetic analysis presented in FIG. 20: Scheme 8. Of the two approaches in FIG. 20: Scheme 8, the upper pathway involves the fewest steps from a known intermediate: the trialdehyde analogue of Kemp's triacid.[87] The anionic tricyclization required for connecting the rotor to the base is not well precedented in the literature, so the lower approach constitutes an alternate synthetic route. Here the base/rotor condensation is well precedented, but the tricyclization involves a novel, 3-fold Wittig rearrangement of an orthoacid which is a reasonable extension of the acetal [1,2]-Wittig rearrangement.[88-92]

Figure 21:
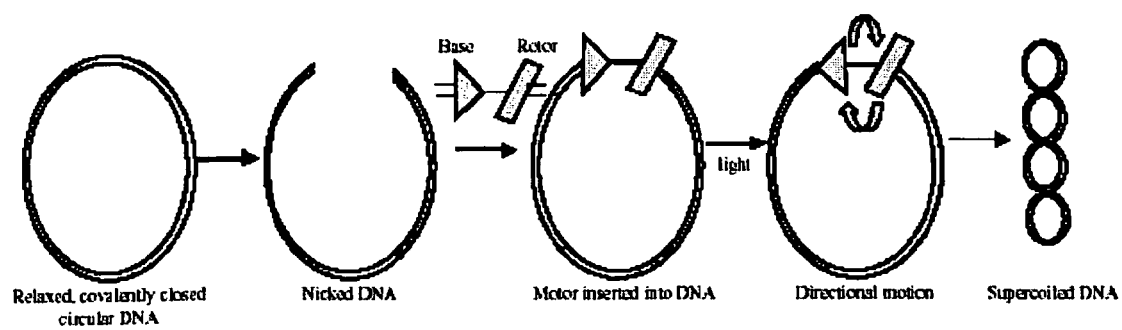
FIG. 21 depicts the insertion of a molecular motor into relaxed, covalently closed circular DNA and supercoiling of the DNA.

The shorter route to Motor II is shown in FIG. 21: Scheme 9, along with methods for synthesis of Kemp's triacid analogues. The trianion of cis,cis-1,3,5-cyclohexanetricarboxylic acid 22 has been treated with dimethyl sulfate or allyl bromide to give mainly the cis,cis trialkyl products (R=CH$_3$ or CH$_2$CH=CH$_2$).[93-95] For the purpose of identifying motor function by photochemical interconversion of atropisomers produced by a non-C3-symmetric base, the monoanion or dianion of 22 can be alkylated to differentiate one of the three R groups. For example, diallylation followed by monomethylation would give a final product in which the $^1$H NMR signal of the methyl group could be used to calculate the ratios of the three atropisomers. The two allyl groups of this product can also be functionalized as tethers for DNA incorporation. The C3-symmetric base in which all three alkyl groups are allyl (R=CH$_2$CH=CH$_2$) can be further functionalized to produce amine or thiol "feet" for surface immobilization, as described later. Trialkyl derivatives of 22 are reduced with lithium aluminum hydride[96] to give triol 23, which is oxidized to trialdehyde 24. This oxidation has been carried out in 53% yield for the trimethyl derivative (R=CH$_3$) by means of modified Swern conditions employing trifluoroacetic anhydride.[96,97]

Tricyclization of trialdehyde 24 by reaction with 9-ethylideneflourene 25 under basic conditions is an important step in FIG. 21: Scheme 9. Alkylation of the anion of 9-ethylidenefluorene occurs preferentially at the 9-position,[98] but condensation with aldehydes occurs at the desired terminal position, on the methyl group.[99,100] The difference is that alkylation is not reversible and the product of kinetic attack is isolated. Under the conditions of condensation with aldehydes (e.g., benzyltrimethylammonium hydroxide in pyridine, ethanolic KOH, or sodium ethoxide), reversible C—C bond formation yields the thermodynamically more stable product. The well-known stability of the adamantane ring system drives the reaction downhill to triol 26. Swern oxidation of 26 to the corresponding triketone, followed by reaction with alkyllithium reagents (e.g., t-butyllithium) gives triol 27, possibly stereoselectivity via coordination of ROLi to axial OLi groups. The OH groups of 27 are reduced by means of tributyltin hydride reaction with the corresponding methyl xanthate, as shown in FIG. 21: Scheme 9. The resulting Motor II having a C$_3$-symmetric base can be separated from the one other possible stereoisomer if the more stable Motor II is not produced with some selectivity in the radical-mediated reduction. Intermediate 27 need not be isolated, as the trialkoxide product from the alkyllithium reaction can be treated directly with carbon disulfide, eliminating two steps. Thus, the simplest motor (R=CH$_3$) can be prepared from known trialdehyde 24 in only five steps.

Figure 22:
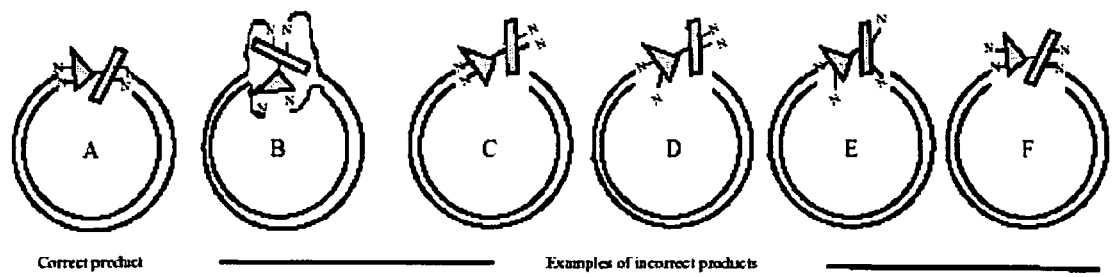
FIG. 22 depicts possible insertions of a molecular motor into relaxed, covalently closed circular DNA.

As an alternative to the one-step tricyclization of 24 to 26 (FIG. 21: Scheme 9), a stepwise approach is shown in FIG. 22: Scheme 10. The first C—C bond between the base and the rotor is formed irreversibly by reaction of the dianion 28 of 9-acetylfluorene[101] with trialdehyde 24. Kinetic reaction of 28 at the less basic, terminal position and trapping of the resulting dianion (e.g., with t-butyldimethylsilyl chloride) gives 29 (R"=TBS). Reaction of 29 with an excess of a weaker base (e.g., an alkoxide) completes the tricyclization. Alternatively, the remaining two C—C bond formations may be conducted with stoichiometric base in a stepwise fashion, as shown in FIG. 22: Scheme 10. Deprotection of 30 gives a trihydroxyketone, which is reduced to the tetra-alcohol with LAH or other reducing agents. 9-Fluorenyl carbinols undergo elimination to 9-alkylidene fluorenes under mild, acidic conditions,[99] so 26 is formed selectively because the three hydroxyls on the adamantane skeleton lack β-hydrogens. Triol 26 is then be converted to Motor II, as shown in FIG. 21: Scheme 9.

Figure 16:
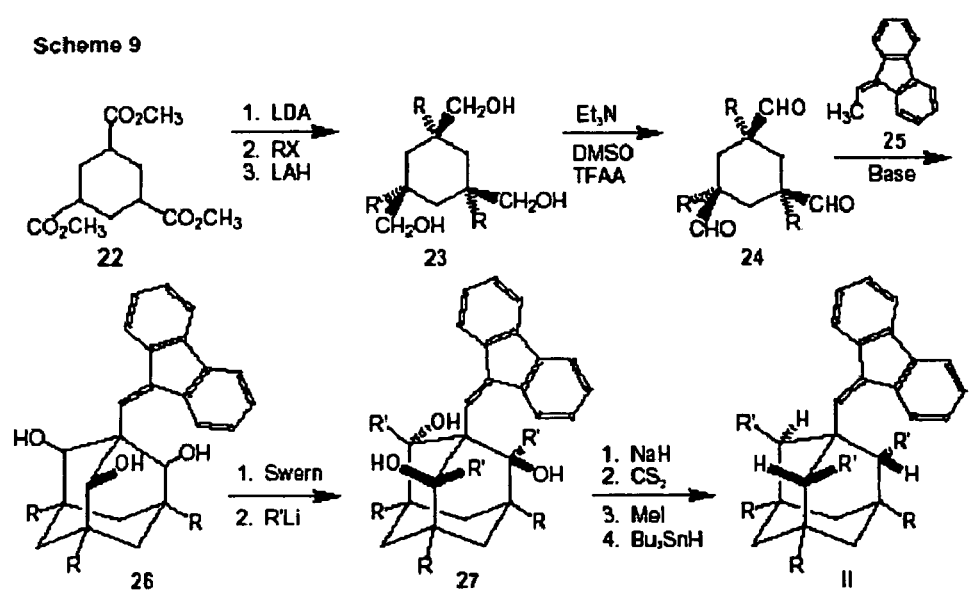
FIG. 16 depicts Scheme 9, a synthesis of an exemplary Motor II.
Figure 17:
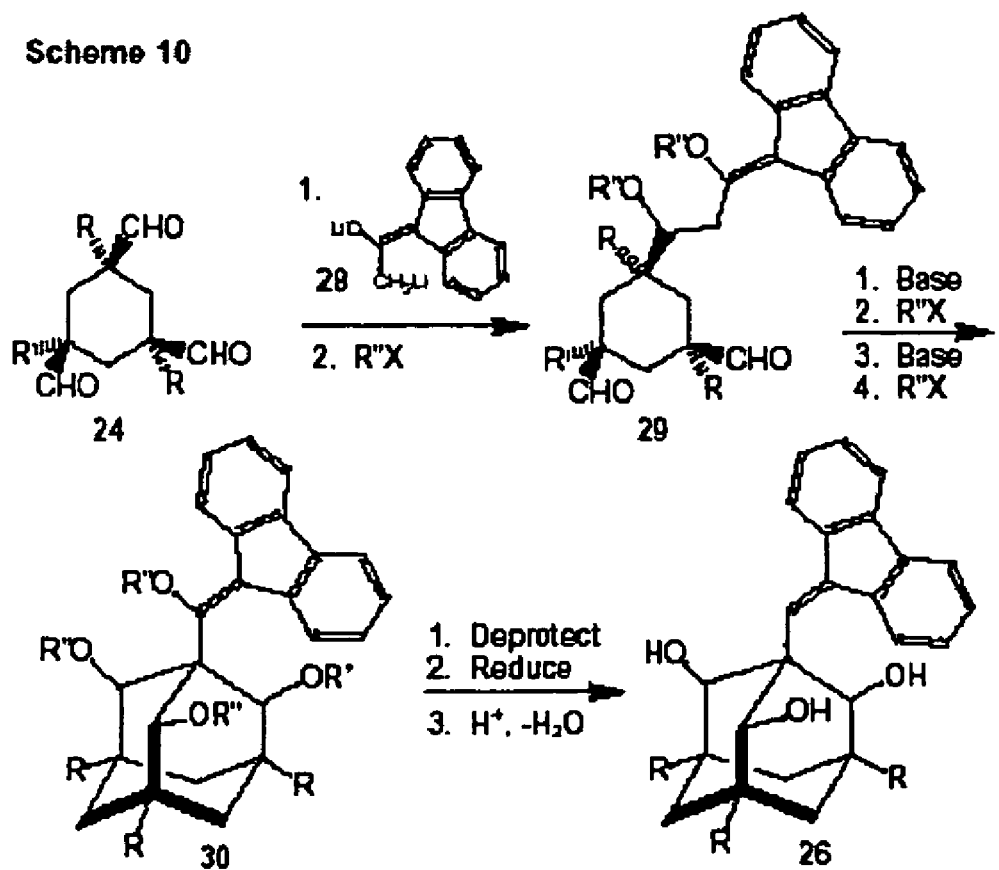
FIG. 17 depicts Scheme 10, an alternate synthesis of an exemplary Motor II.
Figure 18:
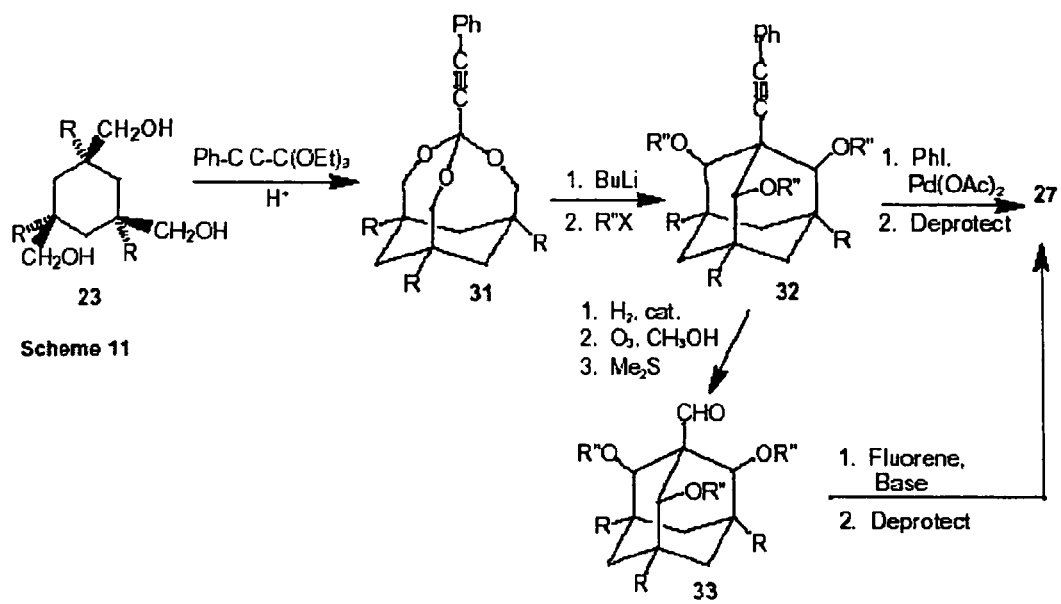
FIG. 18 depicts Scheme 11, a Wittig rearrangement synthesis of an exemplary Motor II.

In case the yields of both routes shown in FIGS. 16 and 17: Schemes 9 and 10 are too low, the Wittig rearrangement approach shown in FIG. 23: Scheme 11 has been devised. Triol 23, which is known for R=CH$_3$[96,97] reacts with the triethyl orthoester of phenylpropynoic acid[102,103] under acidic conditions to form tricyclic orthoester 31. The 3-fold [1,2]-Wittig rearrangement (31-32) is novel. The [1,2]-Wittig rearrangement of acetals and ketals has been used in recent years to convert Oglycosides to C-glycosides.[88-92] The [1,2]-Wittig rearrangement of carbanions proceeds via homolytic C—O bond cleavage to form acyl radical anion and alkyl radical intermediates, which recombine with C—C bond formation. Stabilization of the radicals formed from 31 by conjugation with the phenylacetylene group will facilitate the Wittig rearrangement. Accumulation of negative charge in the proposed 3-fold Wittig rearrangement may reduce the rate of each subsequent reaction, but this difficulty can be overcome by a stepwise variation in which each alkoxide intermediate is trapped with TBSCI. Allylic ethers preferentially give [2,3]-Wittig rearrangements, but acetylenic ketals undergo the [1,2]-Wittig rearrangement in high yield. [88,91,92] For this and stereoelectronic reasons, allenes should not be formed from [2,3]-Wittig rearrangement reactions of 31.

The phenylacetylene group of 32 can be convened directly to the desired 9-fluorenylidene rotor by the method of Larock,[65,66] and deprotection will give triol intermediate 27 (FIG. 21: Scheme 9). This route is be useful for motors with unsubstituted rotors, but substituents may be difficult to introduce regioselectively by the Larock method. Therefore, the triple bond of 32 can be reduced to a double bond by catalytic hydrogenation (e.g., with Lindlar's catalyst), then ozonolysis gives aldehyde 33. Condensation of 33 with various fluorenes,[101] followed by hydroxy deprotection, gives intermediate 27 with substituted rotors. Reaction of 33 with fluorenyl anion does not suffer from the fragmentation side reaction shown in Scheme 2, because the 1-adamantyl anion is not a good leaving group, unlike the trityl anion.

As stated previously, the three R groups on the adamantane base of Motor II are preferably all the same (e.g., CH$_3$, CH$_2$CH=CH$_2$, or CH$_2$CH$_2$CH$_3$) or one can be different from the other two. Motors for DNA incorporation or surface immobilization require two functional tethers or three "feet," respectively. These are be fashioned from allyl groups by the following reactions:

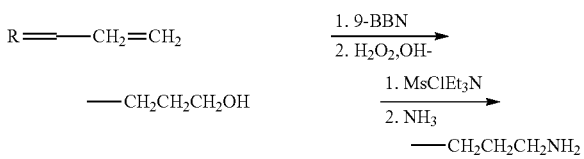

The resulting 3-aminopropyl groups can be acylated for DNA incorporation or protonated to function as feet for binding to anionic surfaces. Alternately, thiol groups can be introduced in the last step to produce molecular motors that could be immobilized on gold surfaces.

The chiral molecular motors are be resolved by fractional crystallization of salts with enantiomerically pure acids (e.g., N-acetyl-L-phenylalanine),[104] or by preparative chromatography on silica-supported polysaccharide derivatives.[105-107]

Example 4

Motor I Photochemistry Study

The energy in a photon absorbed by the motor can be expended mechanically by delivery to a load, it can be lost due to nonradiative processes and intramolecular vibrational energy redistribution (IVR), or the rotor chromophore can fluoresce. We have carried out preliminary studies of model compound 3 (FIG. 4: Scheme 3) to evaluate the feasibility motor operation and spectroscopic detection of the rotor position. Absorption spectra of 3 in n-hexane show a series of peaks at 291, 306, and 318 nm which are assigned to vibrational structure in the $(\pi, \pi)$ transition of the dibenzofulvene chromophore. Strong absorptions at shorter wavelengths around 250 nm are due to the phenyl rings of the base[122] and to a higher energy excited state of the rotor.[123] The $(\pi, \pi)$ absorption is structured, with a maximum at 318 nm and absorption disappears at wavelengths longer than 330 nm. The emission spectrum is di.use and extends from 380-600 nm with a maximum at 456 nm. The fluorescence quantum yield was measured (in ethanol at room temperature, using an anthracene standard) to be $\Phi_F$=0.007 at the 306 and 318 nm absorption peaks. This quantum yield is qualitatively similar to that measured for the $(\pi, \pi)$ transition of the similar fluorenone and its derivatives.[124,125] To test for photoisomerization, a $CDCl_3$ solution of Z isomer 8 (depicted in FIG. 4: Scheme 3) was irradiated by a discharge lamp at 254 nm and pulsed lasers at 266 and 310 nm producing the photostationary state, containing both Z and E isomers (8 and 9), determined by NMR. Extended, high power, pulsed laser excitation at 266 nm results in some photochemical decomposition of the motor (detectable by NMR). The photodecomposition decreases dramatically at 310 nm, while the photoisomerization still occurs. These preliminary studies on model compounds 3 and 8 demonstrate that (1) the dibenzofulvene rotor chromophore can be selectively excited, (2) that absorption leads to isomerization about the ethylenic double bond (the "θ-rotation" of Motor I), and (3) that there is a small quantum yield for emission of the rotor chromophore. While this emission is a small source of energy inefficiency (if the motor emits, the photon energy is not delivered to the load), the rotor emission can be exploited in polarized fluorescence spectroscopy to provide information about the rotor orientation (see Example 5 below).

Example 5

Detection and Control of Rotor Position of Immobilized Motors

Two schemes may be used to detect directional motion: here for surface immobilized motors, and in Example 6 below, for mobile motors. The motor molecule is immobilized on a substrate and polarization spectroscopy is used to detect preferred senses of rotation upon optical irradiation of the rotor chromophore. Unambiguous optical detection of a preferred sense of rotor motion can be accomplished by immobilizing the motors on a substrate so that the Φ axis of rotation is oriented in one direction (see angle definitions in the diagram of a preferred Motor I above). The base of the molecular motors will be chemisorbed to a substrate with the Φ axis of rotation oriented normal to the surface and the rotor chromophore located in a plane approximately perpendicular to the surface. Light absorption will rotate the rotor by 120 about the Φ axis. The location of the rotor plane will be both controlled and detected by polarized spectroscopy.

The ideal substrate is relatively flat, optically transparent, and interacts strongly with the motor to provide spatial orientation, e.g., optical quality amorphous fused silica[170] and crystalline quartz surfaces. These substrates are routinely used in fluorescence studies of immobilized chromophores. To bind the molecular motors the chemically cleaned $SiO_2$ substrate is silanized the chemically cleaned $SiO_2$ substrate with 3-chloropropyltrimethoxysilane $[Cl(CH_2)_3Si(OCH_3)_3]$ using the method of Goss, et al.[171,172] Reaction of this silanized surface with the secondary amine groups of the motor base will produce a self-assembled monolayer,[172] or a sub-monolayer if desired, of molecular motors oriented with the motor base directed towards the surface as shown in the left diagram of FIG. 19.

Operation of the chemisorbed motors is detected in a polarized laser-induced fluorescence scheme. A frequency-doubled, polarized light pulse from a tunable nanosecond dye laser is directed along the surface animal (the z-axis at left). The narrow bandwidth (0.2 $cm^{-1}$) light can be tuned to features in the 291-318 nm range of the $(\pi, \pi)$ transition. A single laser pulse induces some fraction frot of the adsorbed motors to rotate and some fraction ffl to fluoresce—polarized fluorescence from the ffl fraction is used to detect the distribution of rotor positions.

For highly fluorescent molecules, such as laser dyes, it is possible to use traditional light collection techniques to detect the fluorescence of a sub-monolayer of adsorbed molecules.[170,173,174] As discussed in Example 4, preliminary studies of model compound 3 (depicted in FIG. 4: Scheme 3) show a low fluorescence quantum yield in solution (0.007). A similar quantum yield is expected when adsorbed to a non-conductive glass surface.[173] Many approaches for extremely sensitive detection of surface adsorbate fluorescence have been demonstrated in single-molecule detection experiments.[175-177] Among these methods the least expensive and easiest to implement are widefield[178] and farfield confocal fluorescence microscopies,[179,180] techniques with only modest spatial resolution (high resolution is not required here), allow high incident power to be delivered to the sample, and offer high collection efficiency of light emitted by the sample. Note it is not necessary to probe individual motor molecules: to do so would require a high fluorescence quantum yield that is incompatible with efficient motor operation. Instead, the relatively weak fluorescence from the very large number of molecules in many square micrometers of surface is collected using sensitive techniques adapted from known single molecule fluorescence techniques.

Figure 19:
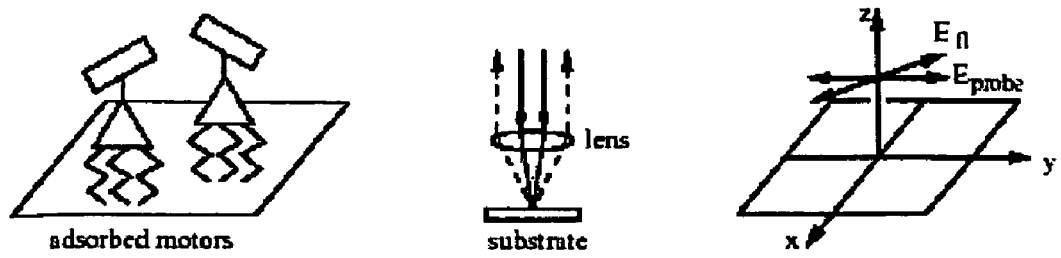
FIG. 19 depicts compounds of the invention attached to a surface.

A confocal geometry is shown schematically in the center diagram of FIG. 19. Both the incident laser light (solid lines) and the collected sample emission (dotted lines) can pass through a single microscope objective lens. The widefield and confocal geometries may be used for substrates such as quartz or mica, which are birefringent or potentially have undesirable optical properties. For other materials, such as fused silica glass or LiF, the excitation pulse can pass through the substrate to backlight the chemisorbed motors.

The background studies of compound 3 in Example 4 indicates that fluorescence will appear in the 380-600 nm range, and dichroic optics will be used to separate the UV excitation and fluorescence wavelengths and notch filters are used to remove any remaining excitation light from the fluorescence. Such procedures are routine in single-molecule detection experiments. The right side of FIG. 19 shows selected polarization angles for the excitation laser light Epump and for the optics that collect sample fluorescence Efl. The optics required for polarization control are commonly used in single molecule detection experiments.[175-177,181-183]

Fluorescence polarization can be related to an anisotropic distribution of chromophore orientations. For excitation/detection on an electric-dipole transition, the probability of photon absorption/emission is proportional to $\cos^2\theta = |E \cdot \mu|^2$, where $\grave{E}$ is the angle between the electric polarization vector of the absorbed/emitted light, Epump/Efl, and the transition dipole moment vector, $\mu$, of the chromophore.[184] The transition dipole $\mu$ for the ($\pi, \pi$) transition of the rotor chromophore is expected to be polarized perpendicular to its molecular plane, and therefore nearly parallel to the surface. Motors having transition dipoles aligned with the pump laser polarization preferentially absorb the pump light.

There are many scenarios which may be used to detect preferred senses of rotation using the apparatus described above. A relatively simple scenario create an anisotropy in the population of the immobilized molecular motors using a series of linearly polarized laser pulses (see right diagram of FIG. 19). The laser polarization is then changed so that the anisotropy evolves as subsequent laser pulses are delivered. A Monte Carlo simulation of $10^5$ motors with random base orientations on the surface. Initially the rotor of a motor can be in any of the three-fold sites of the base. In the simulation, the surface is irradiated with either vertically (V) or horizontally (H) polarized pump light and the polarized fluorescence normal to the surface is detected. The pump laser pulse irradiates the immobilized molecular motors, with a 5% overall probability for successful rotation by 120. The results of the simulation are shown in the FIG. 20. (The cw or ccw sense of the rotor motion depends upon which enantiomer of the motor is chosen for adsorption to the surface—both are shown here (labelled cw and ccw), but only one would be used in practice.

Figure 20:
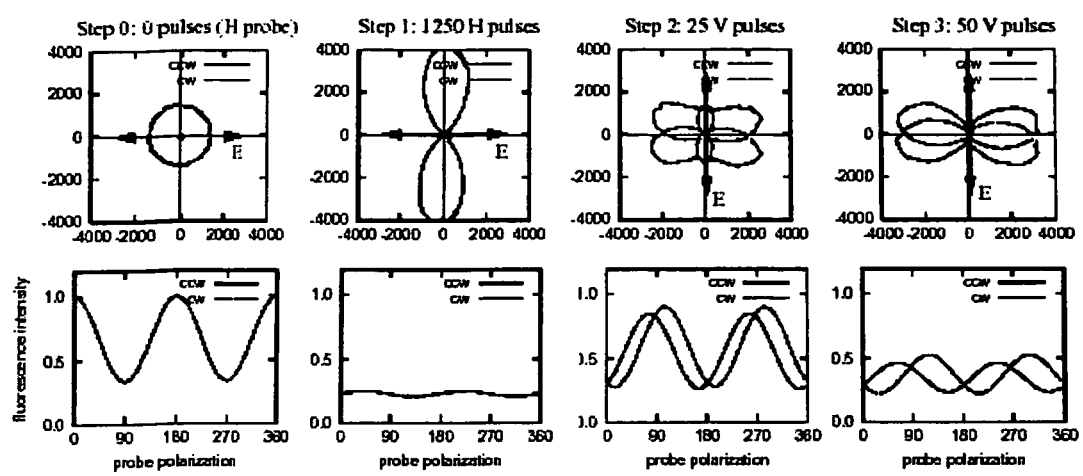
FIG. 20 depicts diagrams (top row) showing the angular probability of rotor orientations in the surface xy-plane as a radial polar plot. The bottom row shows the fluorescence intensity as a function of polarization for either V or H excitation.

The top row of diagrams in FIG. 20 shows the angular probability of rotor orientations in the surface xy-plane as a radial polar plot. The bottom row shows the fluorescence intensity as a function of polarization for either V or H excitation. The fluorescence polarizer detection angle, θfl, is measured ccw from the horizontal x-axis. A convenient technique is to use a polarizing prism to separate the sample fluorescence into orthogonal (s and p) polarization states, which are then independently and simultaneously detected. The following analysis specifically considers detection at θfl=45° and 135°, though the intensity at all angles is shown in FIG. 20.

FIG. 20 shows the following steps: Step 0: initial state—Initially (top left), the rotors are randomly aligned and a H laser pulse is used to excite the motors. The observed fluorescence polarization in the bottom left diagram arises from the polarization of the incident laser pulse. Note that the fluorescence intensities at θfl=45°, 135° are identical.

Step 1: creation of spatial anisotropy—Next, 1250 H polarized pump laser pulses align the transition dipole moments of the rotor chromophores to be preferentially perpendicular to the pump polarization (where they become "stuck" due to the perpendicular orientation of Epump and $\mu$.) The angular distribution of chromophore transition dipoles approximately has a $\sin^2\theta$ dependence. This is a steady-state angular population that would not evolve if additional horizontally polarized pump pulses were delivered. The fluorescence intensity and polarization are small because Epump and $\mu$ are mostly perpendicular. Fluorescence intensity at θfl=45 and 135 is identical.

Steps 2 and 3: measurement of preferred sense of rotation—Now the pump polarization is set to vertical and pump pulses are applied to disturb the alignment created in Step 1. A ccw rotating ensemble of molecular motors will evolve to accentuate the angular probability for transition dipoles to lie in the range 0<θ<90°. After 25 V pulses, for ccw motors, the fluorescence intensity at θfl=45° is 1.6 times that at 135°. (If we used cw motors instead, the reciprocal polarization ratio would be observed.) Subsequent laser pulses will tend to destroy the polarization differences as a distribution is created similar to that in Step 1, but rotated by 90°.

Such large and easily measurable fluorescence polarization differences, as in Step 2 above, will immediately qualitatively identify the preferred sense of motor rotation. The efficiency of motor rotation per laser pulse (per photon absorbed) is quantified by how rapidly the ensemble of rotor orientations responds to a change in pump laser polarization. The efficiency will extracted by fitting parameters in Monte Carlo and other simulations of the experimental florescence polarization measurements. Monte Carlo simulations show that rotating the laser polarization during a sequence of pulses will create an angular distribution of rotors that tracks the polarization. Using more strongly orienting crystalline substrates (e.g. LiF) capable of aligning the base, forces the allowed rotor positions into specific directions along the crystal surface. Muscovite mica is one such substrate because of its atomic scale flatness over macroscopic dimensions and its strongly orienting 3-fold symmetry axis.[185-188] This offers the potential for very precise optical positioning of an ensemble of rotators by extending the polarization methods described above. It has been shown that alkylammonium ions form self-assembled monolayers on the negatively charged mica surface with the alkyl chains oriented roughly perpendicular to the surface.[187] Motors containing bases 13 or 18 (structures depicted in FIG. 6: Scheme 5) will be triprotonated at neutral pH, so they will bind to mica via their base tripods, orienting the rotor double bond at an approximately 135° angle relative to the surface.

Example 6

Incorporation of a Compound of the Invention into Circular DNA and Supercoiling

The overall process from motor insertion through supercoiling is shown in FIG. 21.

Synthetic Approach: Relaxed, covalently-closed, circular DNA is nicked using methods known to provide an opening to insert a compound of the invention into the DNA. The compound or motor inserts into the DNA by attaching to both DNA strands on each side of the nick (see construct A in FIG. 22). The 4 DNA-motor covalent bonds must be made for rotor motion to cause supercoiling. There are two general ways to accomplish this. The most direct approach is to synthesize the motor with four identical linkers containing primary amines, as shown in FIG. 22. These linkers contain charged groups to increase water solubility, as all DNA reactions must be done in aqueous buffers. After nicking the DNA, the 5' end retains a phosphate group, whereas the 3' end is unphosphorylated. After enzymatic phosphorylation of the 3' end, both the 3' and 5' ends[201,202] will be converted to a phosphorimidazolide by facile reaction with carbonyldiimidazole in imidazole buffer.[202] This intermediate will react in good yield with the primary amines of the motor linkers (in excess) to give the stable phosphoramidate products. These reactions have been used previously in syntheses of nucleotide derivatives.[203] FIG. 22 also depicts incorrect constructs (B) and incomplete constructs (C, D, E and F) which may be generated.

Figure 23:
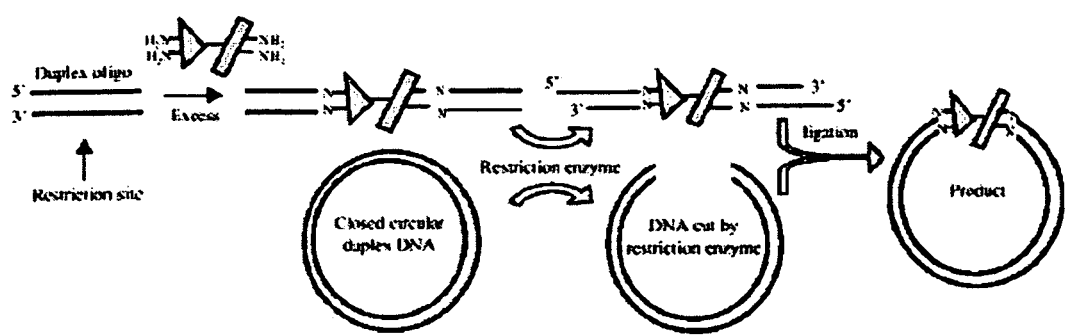
FIG. 23 depicts one approach to insert a molecular motor of the invention into relaxed, covalently closed circular DNA.
Figure 24:
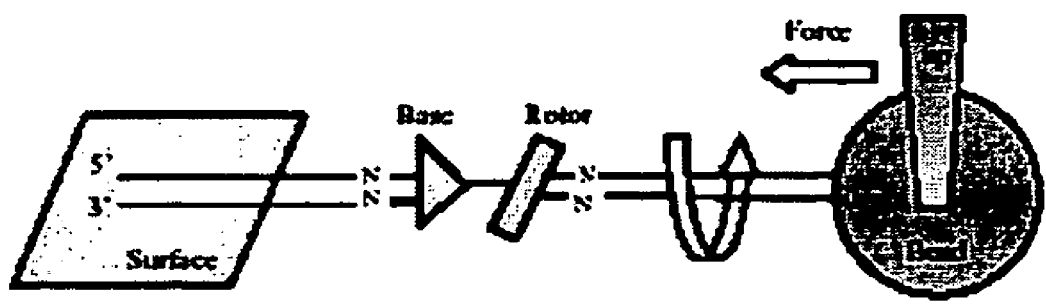
FIG. 24 depicts a technique to measure the forces generated by a molecular motor-DNA construct.
Figure 25:
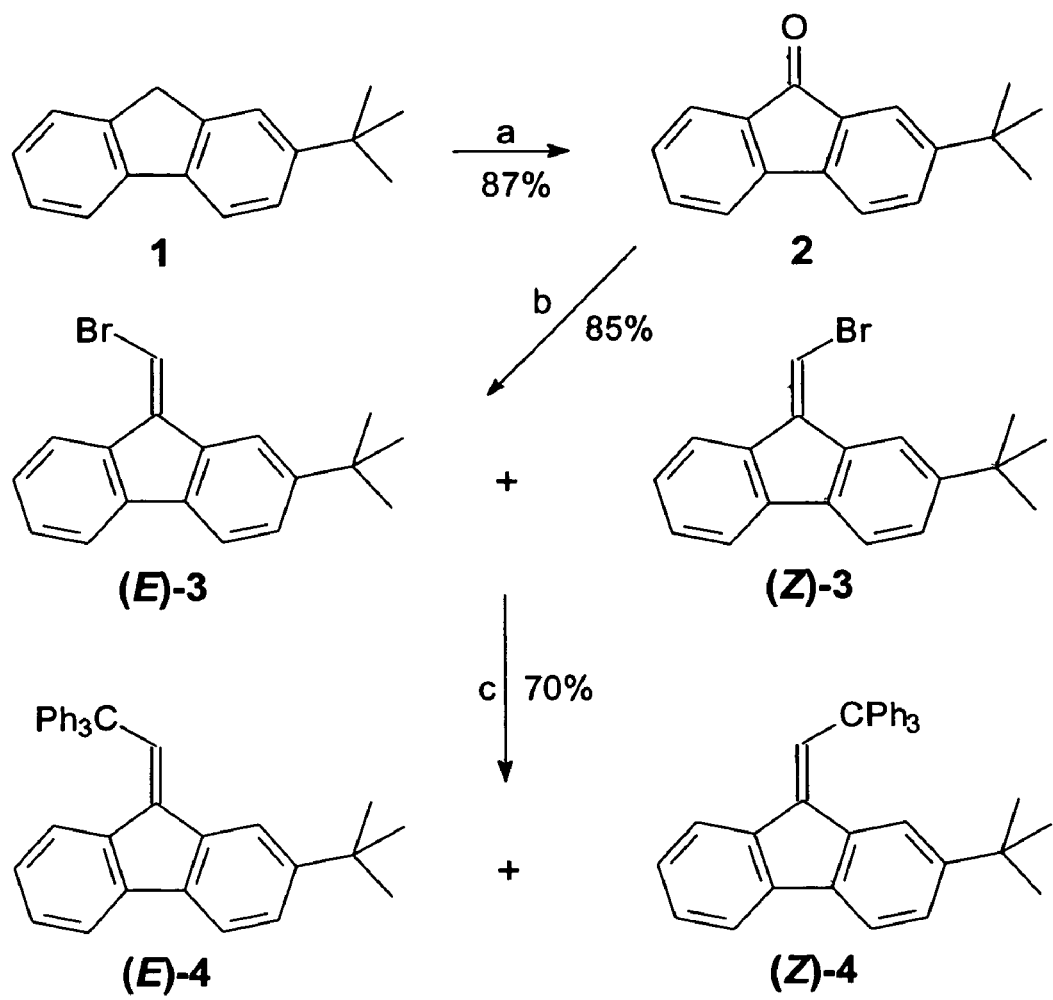
FIG. 25 depicts the synthesis of (E)- and (Z)-2-tert-butyl-9-(2,2,2)-triphenylethylidenefluorene.
Figure 26:
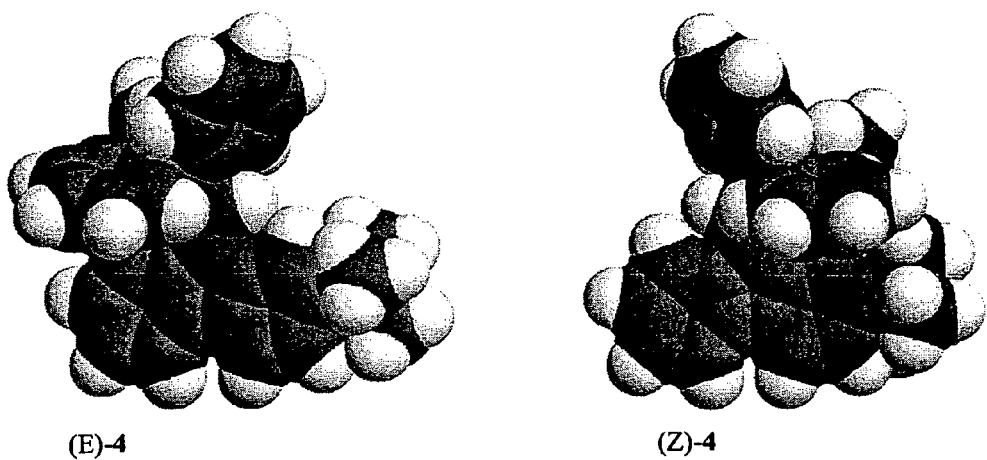
FIG. 26 depicts space-filled diagrams of crystallographically determined confirmations of (E)- and (Z)-2-tert-butyl-9-(2,2,2)-triphenylethylidenefluorene.

An alternative approach to preparation of constructs A and B in FIG. 22 is shown in FIG. 23. Complementary double-stranded oligonucleotides (containing a cleavage site for a restriction enzyme) is attached to the motor through a phosphoramidate linkage as described above. The oligo-motor-oligo complex and closed circular DNA is cut with the same restriction enzyme and the two are joined using standard molecular biological techniques.[204] The product can be isolated by gel electrophoresis. An advantage of this approach is that the process of DNA hybridization (complementary base pairing) correctly insertz the motor to form a closed circular DNA product. The disadvantages are common to conventional cutting and joining or DNA molecules, mainly low yield of insertion. Several variations can be employed to minimize these problems. For example, two nonidentical linkers could be used which avoids the problems of the plasmid DNA reannealing to generate the "empty" plasmid. However, this would require asymmetrical attachment of different sequence oligos onto the motor prior to insertion into the plasmid. This can be accomplished by selective blocking of the motor amines only on one end of the molecule. After reaction with the first oligonucleotide, the amines would be unblocked and the second (different) oligonucleotide would be attached.

Another alternative is to attach thiol linkers to the oligos using phosphoramidite chemistry performed in the DNA synthesizer.[205,206] These oligos could be purified by standard methods and reacted with a motor modified with maleimides. One advantage of using DNA to assess motor function is that the techniques described here require very little material. DNA reactions are usually performed in less than 10 μL. Gel electrophoresis is extremely sensitive because fluorescent dyes are used to visualize and quantitate constructs.

Purifying constructs with properly attached motors: Constructs that are not fully coupled to the motor molecule are degraded by reaction with enzymes that degrade DNA through reaction from the ends. Since products A and B have two closed DNA loops, they can be separated preparatively from products C, D, E and F by gel electrophoresis in the presence of ethidium bromide (DNA intercalator). Only the correct product, A, and its constitutional isomer, B, will have a closed circular structure before and after melting of the DNA duplex (removing the interactions between the strands). Gel electrophoresis can then isolate the correct constructs. To distinguish between A and B, ethidium bromide intercalation will differ significantly between the two isomers, allowing isolation. The productive rotor motion in B is unlikely due to free energy considerations of complementary strand dissociation. However in A, motor motion should result in supercoiling. Therefore, motor motion could still be detected in the mixture of A and B, as long as the yield for A is sufficient (50 pg per band). The presence of the motor in a construct can be verified by UV-VIS spectroscopy as the motor will absorb significantly above 260 nm (unmodified DNA maximum). In addition, The purified products with an electron microscope using the method of rotary shadowing.[207] Constructs A and B should also be readily distinguished from structures C-F with this method. In addition, supercoiling can be detected with this method although it may be difficult to verify the extent of supercoiling.

Light-activated directional motor function, and estimate forces generated, through an analysis of the supercoiling reaction: DNA supercoiling is readily determined by using the well-established 1- and 2-dimensional agarose gel electrophoresis methods.[208-210] These methods are readily available in any molecular biology laboratory, are rapid, and require little equipment. If the motor is properly inserted into a relaxed covalently closed circular DNA, this species should migrate electrophoretically at a defined location in the gel. When the motor is irradiated with light and induced to twist the DNA, supercoils will be generated and an increase in electrophoretic mobility should be observed. Moreover, the number of supercoils generated can be counted with this method. Depending upon the irradiation energies relative to the motor activation energies, a distribution of molecules with different degrees of supercoiling should be observed. Molecules are visualized on the gel with ethidium bromide or Cybr green dyes that intercalate into the DNA and strongly fluoresce. The detection limit with these dyes is about 50 pg of DNA.

Measuring forces generated by the motor-DNA construct with an atomic force microscope: Having obtained supercoiling of the DNA gyrase, measurements of force in the time domain can be made using atomic force microscopy (see FIG. 19). The rotor is inserted between two double-stranded oligonucleotides of sufficient length to attach one end to a surface and the other end to a bead. The tip of the microscope is attached to the bead and the entire molecule is extended. Upon light activation, exact forces generated by the motor are recorded as forces on the microscope tip. The advantage of this approach is that the measurements are made upon a single motor molecule in real time.

Example 7

Syntheses, Structures and Photoisomerization of (E)- and (Z)-2-tert-Butyl-9-(2,2,2-triphenyethylidene) fluorene (E)- and (Z)-2-tert-butyl-9-(2,2,2)-triphenylethylidene-fluorene (4) were prepared by the method developed previously for the synthesis of 9-(2,2,2)-triphenylethylidenefluorene (5).[6] As shown in FIG. 20, 2-tert-butylfluorene (1) was converted by air oxidation to 2-tert-butylfluorenone (2).[7] As reported for fluorenone,[8] Wittig reaction of 2 with bromomethylenetriphenylphosphorane gave the bromomethylene derivative 3, in this case as a ca, 1:1 mixture of E and Z stereoisomers. Reaction of (E/Z)-3 with triphenylmethyllithium then afforded a 1:1 mixture of (E)-4 and (Z)-4, in significantly higher yield than reported for the unsubstituted analogue (5).[6] These target stereoisomers were separated by sequential column chromatography on alumina and crystallization from hexane. The reaction conditions in FIG. 20 were as fellows: a) $O_2$, Triton B, pyridine, 25° C., 36 h. b) $BrCH_2PPh_3Br$, NaHMDS, THF, 31 60° C.; 2, 25° C., 18 h. c) $Ph_3CH$, nBuLi, THF, 0° C.; 3, −78-25° C., 25 h. Triton B=benzyltrimethylammonium hydroxide; NaHMDS=sodium bis(trimethylsilyl)amide. Analytically pure samples of both (E)-4 and (Z)-4 were obtained for photoisomerization studies.

The structures of both (E)-4 and (Z)-4 were determined by single-crystal X-ray diffraction. In both structures, there are two molecules in the asymmetric unit, and the tert-butyl group is rotationally diordered in every case. Crystallographically-determined, space-filling diagrams of a representative conformation of both stereoisomers are shown in FIG. 21. It is clear from the diagram of (Z)-4 that there is no steric interference between the triphenylmethyl (trityl) and tert-butyl groups; the closest C—C distance between phenyl and methyl carbons is 3.860 Å. The parent molecule lacking a tert-butyl group (5) shows an unusual distribution of bond strain. Most of the distortion around the exocyclic double bond in this overcrowded trisubstituted alkene occurs as bond angle deformation, rather than torsional strain. Table 1 compares the bond angles for the exocyclic double bonds of (E)- and (Z)-4 with 5. It is clear from this comparison that the geometries of this key, photoactive double bond are essentially the same in all three compounds.

TABLE 1

Crystallographically determined bond angles [°] for the exocyclic double bond of (E)-4, (Z)-4 and 5[6].

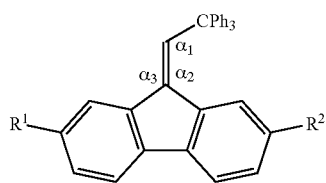

(E)-4: $R^1$ = tBu, $R^2$ = H
(Z)-4: $R^1$ = H, $R^2$ = tBu
5: $R^1$ = $R^2$ = H

| Alkene | $\alpha_1$ | $\alpha_2$ | $\alpha_3$ |
| --- | --- | --- | --- |
| (E)-4 (mol 1) | 133.2(5) | 133.7(5) | 121.8(5) |
| (E)-4 (mol 2) | 133.6(5) | 134.8(5) | 120.8(5) |
| (Z)-4 (mol 1) | 134.1(4) | 133.7(4) | 121.7(4) |
| (Z)-4 (mol 2) | 130.8(3) | 132.6(3) | 122.5(3) |
| 5 (mol 1) | 134.7(3) | 134.5(3) | 120.8(3) |
| 5 (mol 2) | 133.5(3) | 134.3(3) | 121.1(3) |

Figure 27:
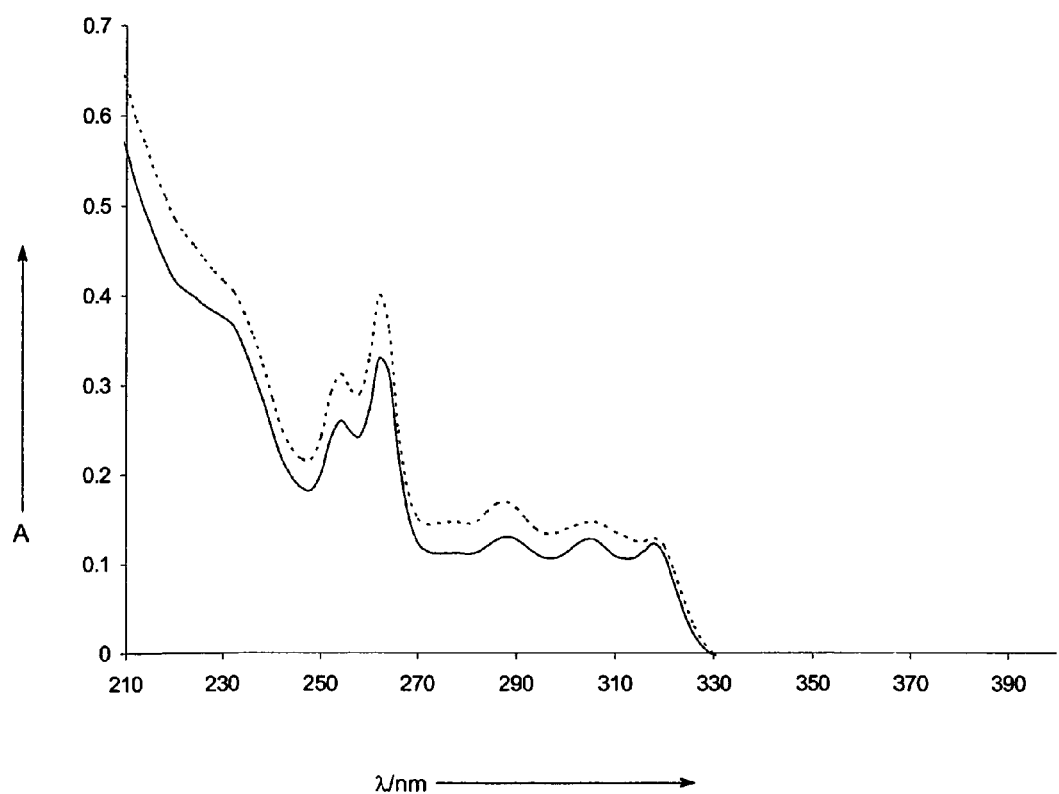
FIG. 27 depicts the UV absorption spectra of both stereoisomers of 2-tert-butyl-9-(2,2,2)-triphenylethylidenefluorene: (E)-4, dashed line; (Z)-4, solid line.

FIG. 27 shows the UV absorption spectra of (E)-4 and (Z)-4, which do not absorb visible light. These spectra are nearly identical, confirming that interaction between the tert-butyl and trityl groups only has a minor influence on the structure of 4. Pulsed laser light of wavelengths 266, 280, and 320 nm, corresponding approximately to the locations of absorption maxima shown in FIG. 20, was used to carry out the following photoisomerization studies.

The photoisomerization of 4 was studied at room temperature in anhydrous perdeuteroacetonitrile solution saturated with $N_2$. Sample solutions initially contained only (E)- or (Z)-4 at 0.5 μM concentration and were studied by alternately irradiating the sample with UV light and then measuring the $^1$H NMR spectrum. The relative amounts of the Z and E isomers were measured by the peak heights of the tert-butyl protons, located at 0.091 and 1.39 ppm for the Z and E isomers, respectively.

Using the laser pulse energy, repetition rate, and concentration of the solution, the average number of photons absorbed per unit irradiation time was calculated. For example, irradiation of a 0.5 μM solution for 15 sec using 2.0 mJ pulses of 266 nm light at 10 Hz results in an average absorption rate of 0.028 photons/s.

The mole fraction ([E] and [Z]) for each isomer was obtained from NMR spectra by dividing its tert-butyl proton NMR peak height by the sum of the tert-butyl $^1$H NMR peak 2heights for the two isomers. Under the experimental conditions described above, negligible photodecomposition of (E)- or (Z)-4 was observed in the NMR spectra for total irradiations of at least 80 photons/molecule. In the absence of solution agitation during irradiation, photodecomposition during irradiation was demonstrated by the growth of new features in the NMR spectra and by a yellow discoloration of the solution. High laser pulse energies and no solution agitation during irradiation resulted in a black precipitate.

Figure 28:
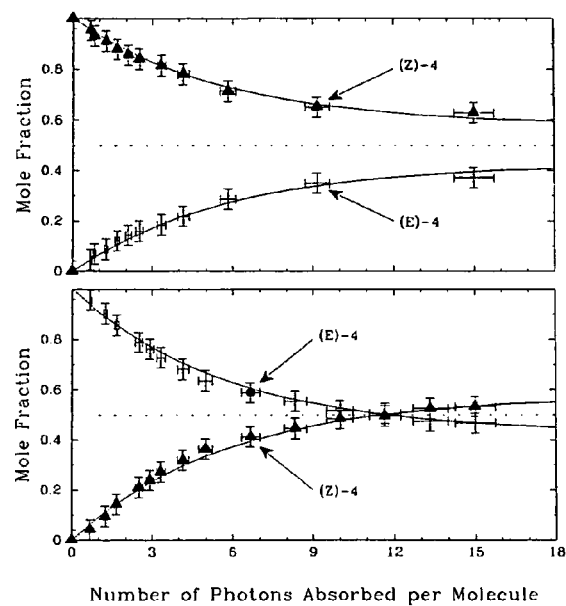
FIG. 28 depicts the photoisomerization data of both stereoisomers of 2-tert-butyl-9-(2,2,2)-triphenylethylidenefluorene at 266 nm showing mole fractions of (Z)-4 (● symbols) and (E)-4 (▲ symbols) as a function of the average number of photons absorbed.

At each wavelength the photoisomerization kinetics was studied from initial solutions of either the pure E or the pure Z isomer of 4. Data from a typical photoisomerization measurement at 266 nm is shown in FIG. 28. In FIG. 3 the photostationary state shows a Z:E ratio of 1.4. The kinetic data for the photoisomerization were fit to a kinetic model accounting for the photoisomerization rates of each isomer and an overall photodecomposition rate:

$$Z + h\nu \xrightarrow{k_{ZE}} E \qquad (1)$$

$$E + h\nu \xrightarrow{k_{EZ}} Z \qquad (2)$$

$$Z + h\nu \xrightarrow{k_D} D \qquad (3)$$

$$E + h\nu \xrightarrow{k_D} D \qquad (4)$$

In Eqs. 1 and 2, $k_{ZE}$ and $k_{EZ}$ are the rates for photoisomerization. In Eqs. 3 and 4, $k_D$ is the photodecomposition rate, which is assumed to be zero under the above conditions for the photoisomerization measurements.

The values of $k_{ZE}$ and $k_{EZ}$ were obtained by non-linear least squares optimization to the solutions for the kinetic scheme in Eqs. 1-4. Assuming no photodecomposition ($k_D$=0), and an initial solution of the pure Z isomer, ([Z](0)=1, [E](0)=0), the time-dependent concentrations are:

$$[Z](t) = \frac{k_{EZ}}{k_{ZE} + k_{EZ}} e^{-k_{ED}t}\left[1 + \frac{k_{ZE}}{k_{EZ}}e^{-(k_{ZE}+k_{EZ})t}\right] \qquad (5)$$

$$[E](t) = 1 - [Z](t) \qquad (6)$$

The time-dependent concentrations for an initial solution of the pure E isomer can be obtained by exchanging the E and Z symbols in Eqs. 5 and 6. If t in Eqs. 5 and 6 is expressed in terms of the average number of absorbed photons, the rates $k_{ZE}$ and $k_{EZ}$ become probabilities per absorbed photon (quantum yields). FIG. 28 shows best fits of Eqs. 5 and 6 to experimental data in which $k_{ZE}$ and $k_{EZ}$ are optimized. The photoisomerization quantum yields at all three photoisomerization wavelengths are shown in Table 2.

TABLE 2

Quantum yields measured at the three wavelengths in the photoisomerization experiments.

| λ | $k_{ZE}$ | $k_{EZ}$ |
| --- | --- | --- |
| 266 nm | 0.074 | 0.100 |
| 281 nm | 0.044 | 0.050 |
| 320 nm | 0.067 | 0.092 |

Synthesis of Compounds and Experimental Details (E/Z)-2-tert-Butyl-9-bromomethylenefluorene (3): A suspension of bromomethyltriphenyl-phosphonium bromide (4.06 g, 9.31 mmol) in anhydrous THF (40 mL) was cooled to −60° C. under $N_2$, and a solution of 2 M sodium bis(trimethylsilyl)amide in anhydrous THF (4.6 mL, 9.2 mmol) was added dropwise. The resulting yellow suspension was stirred for 40 min, and a solution of 2-tert-butyl-9H-fluorene[7] in anhydrous THF (2.01 g, 8.53 mmol) was added. The reaction mixture was then allowed to warm gradually to room temperature and stirred for 18 h. Water was added (50 mL), and the resulting mixture extracted with diethyl ether (3×25 mL). The combined ether solutions were dried over anhydrous $Na_2SO_4$, then concentrated to dryness by rotary evaporation.

The residue was dried under vacuum, giving 4.50 g of a deep red/brown oil. Column chromatography on silica gel (32-60 μm), eluting with hexane, gave 2.27 g of a 1:1 mixture of (E)- and (Z)-3 (85%) as an orange gum-like solid. $^1$H NMR (300 MHz, CDCl$_3$): δ8.56 (d, J=1.5 Hz, 1 H), 8.52 (d, J=7.7 Hz, 1 H), 7.2-7.28 (m, 14 H), 1.42 (s, 9 H, tBu), 1.38 (s, 9 H, tBu).

(E)- and (Z)-2-tert-Butyl-9-(2,2,2-triphenylethylidene) fluorene (4). A solution of triphenyl-methane (3.09 g, 12.6 mmol) in anhydrous THF (15 mL) was cooled to −78° C. under N$_2$ and a solution of n-butyllithium in hexane (1.58 M, 6.5 mL) was added, producing a pink solution. The solution was stirred at 0° C. for 40 min, then the resulting blood-red solution of the trityl anion was recooled to −78° C. and a solution of (E/Z)-2-tert-butyl-9-bromomethylenefluorene (2.47 g, 7.90 mmol) in 10 mL of anhydrous THF was added. The reaction mixture was allowed to warm gradually to room temperature and stirred for 25 h. Water (75 mL) was added, and the resulting mixture was extracted with diethyl ether (4×25 mL). The combined ether solutions were dried over anhydrous Na$_2$SO$_4$, then concentrated to dryness by rotary evaporation. The residue was dried under vacuum, giving 5.03 g of a yellow oil, consisting primarily of (Z)4 (R$_f$0.16 alumina, hexane), (E)-4 (R$_f$0.19, alumina, hexane), and triphenylmethane (R$_f$0.34, alumina, hexane). Sequential column chromatography (50 g of 80-200 mesh alumina, hexane) and fractional crystallization from hexane gave a total of 2.63 g (70%) of the products (0.59 g of pure (Z)-4, 0.35 g of pure (E)-4, and the reminder as mixed fractions).

(Z)-4: m.p 221-223° C.; $^1$H NMR (300 MHz, CD$_2$Cl$_2$): δ=7.84 (s, 1 H), 7.77 (d, J=7.33 Hz, 1 H), 7.7 (d, J=7.32 Hz, 1 H), 7.56 (d, J=8.06 Hz, 1 H), 7.24-7.33 (m, 18 H), 6.84 (s, 1 H), 0.93 (s, 9 H; tBu); $^{13}$C NMR (75 MHz, CD$_2$Cl$_2$): δ=150.0, 141.5, 140.0, 139.2, 138.8, 135.8, 130.8, 128.8, 126.9, 126.2, 120.4, 119.6, 118.8, 62.1, 35.5, 31.9; IR (KBr): ν=3052 (m), 2963 (m), 1594 (m), 1488 (s), 1444 (s), 1420 (w), 1262 (m), 1035 (w), 823 (s), 765 (w), 748 (m), 730 (s), 701 (s) cm$^{-1}$; MS (EI) m/z (%) 477 (5.2) [M$^+$+1], 476 (12.7) [M$^+$], 419 (9.4), 341 (36.3), 265 (11.4), 252 (8.7), 165 (59.1), 139 (13.9), 57 (100); UV/Vis (0.0092 mM, CH$_3$CN): λ$_{max}$ (ε)= 236 (34076), 254 (28261), 262 (35870), 288 (14130), 305 (13772), 318 (13261) nm; elemental analysis calcd (%) for C$_{37}$H$_{32}$: C 93.36; H 6.78; found: C 93.12, H 6.70.

(E)-4: m.p. 215-217° C.; $^1$H NMR (300 MHz, CD$_2$Cl$_2$): δ=7.81 (s, 1 H), 7.76 (s, 1 H), 7.60 (t, J=7.58 Hz, 1 H), 7.41 (dd, J=8.06 Hz, 1 H), 7.22-7.30 (m, 16 H), 7.13 (t, J=7.32 Hz, 1 H), 6.63 (t, J=7.59 Hz, 1 H), 6.45 (d, J=8.05 Hz, 1 H), 1.38 (s, 9 H, tBu); $^{13}$C NMR (75 MHz, CD$_2$Cl$_2$): δ=50.4, 146.8, 138.4, 138.0, 136.4, 135.2, 130.0, 127.6, 126.4, 125.0, 118.4, 116.4, 62.1, 35.5, 31.9; IR (KBr): ν=3056 (m), 2955 (m), 1596 (m), 1488 (s), 1445 (s), 1421 (w), 1262 (m), 1034 (w), 835 (s), 769 (w), 752 (m), 730 (s), 700 (s) cm$^{-1}$; MS (EI) m/z (%) 476 (6.9) [M$^+$], 419 (5.3), 341 (20.0), 265 (7.0), 252 (5.7), 165 (39.0), 139 (9.8), 57 (100); UV/Vis (0.0092 mM, CH$_3$CN): λ$_{max}$(ε)=235 (38456), 255 (33913), 263 (43478), 287 (18152), 305 (15978), 317 (14022) nm; elemental analysis calcd (%) for C$_{37}$H$_{32}$: C 93.36; H 6.78; found: C 93.09, H 6.73.

Crystallographic data for (E)-4 and (Z)-4: a=12.221(1), b=17.921(2), c=13.524(3) Å, α=90°, β=107.82(1)°, γ=90°, V=2820 Å$^3$, M$_r$476.66, P2(1), Z=2, ρ$_{calcd}$ 1.123 gcm$^{-3}$, 6296 independent reflections. Crystal data for (Z)-4: a=11.272(3), b=14.504(3), 17.102(3) Å, α=84.54(2)°, β=86.25(2)°, γ=81.33(2)°, V=2748 Å$^3$, M$_r$=476.66, P−1, ρ$_{calcd}$ 1.152 gcm$^{-3}$, 8506 independent reflections. Suitable crystals were coated in epoxy cement and mounted on a Siemens P4 diffractometer. Data were collected at room temperature, and both structures were solved by direct methods. The non-hydrogen atoms were refined using a riding model in calculated positions with anisotropic thermal parameters. Hydrogen atom positions were calculated using a riding model with a C—H distance fixed at 0.96 Å and a thermal parameter 1.2 times the host carbon atom. The structures were refined on F$^2$ by a full-matrix least-squares program using SHELXTL97.[9] Final R values were for (E)-4, R1=0.0599, wR2=0.1463 for 5478 data, and for (Z)-4, R1=0.0608, wR2=0.1065 for 7188 data, both with 1>2σ(1).

Photoisomerization measurements. The light source for the photoismerization experiments was either a doubled dye laser pumped with the second harmonic of a 10 Hz Nd:YAG laser (for 280 and 320 nm photoisomerization), or the direct fourth harmonic of the Nd:YAG laser (266 nm). Laser pulses were of approximately 5 ns duration. The average laser pulse energy was measured during each irradiation cycle and was typically 2.0 mJ pulse. The photoisomerization measurements were conducted in a flat-bottomed, 1 cm diameter, fused silica nmr tube. The UV laser light was directed through the bottom of the tube. For a concentration of 4 of 5.0×10$^{-4}$ M, the optical density of the solution is 4.0×10$^4$, ensuring that the entire laser beam was absorbed in the sample. During laser irradiation, a stream of N$_2$ pre-saturated with perdeuteroacetonitrile was bubbled through the solution, near the bottom of the tube using a stainless steel syringe needle inserted through a septum at the top of the tube. The flow of N$_2$ served to both displace dissolved O$_2$ and to vigorously agitate the solution during irradiation. Vigorous agitation is necessary to ensure that all molecules have an equal opportunity to absorb a photon over the course of an irradiation cycle (typically 15-60 s).

Notes for Example 7:

[1] a) T. Arai, T. Karatsu, H. Misawa, Y. Kuriyama, H. Okamoto, T. Hiresaki, H. Furuuchi, H. Zeng, H. Sakuragi and K. Tokumaru, *Pure & Appl. Chem.* 1988, 60, 989-998. b) D. H. Waldeck, *Chem. Rev.* 1991, 91, 415-436; c) T Arai, K. Tokumaru, *Chem. Rev.* 1993, 93, 23-39; d) H. Görner, H. J. Kuhn in *Advances in Photochemistry, Vol.* 19 (Eds.: D. C. Neckers, D. H. Volman, G. von Bünau), Wiley, New York, 1995, pp. 1-117; e) J. Saltiel, D. F. Sears, Jr., D.-H. Ko, K.-M. Park in *CRC Handbook of Organic Photochemistry and Photobiology* (Eds.: W. M. Horspool, P.-S. Song), CRC Press, Boca Raton, 1995, pp. 3-15; f) T. Arai in *Organic Molecular Photochemistry* (Eds: V. Ramamurthy, K. S. Schanze), Marcel Dekker, New York 1999, pp. 131-167; g) V. J. Rao in *Organic Molecular Photochemistry* (Eds: V. Ramamurthy, K. S. Schanze), Marcel Dekker, New York, 1999, pp. 169-209.

[2] M. J. S. Dewar, M. C. Kohn, *J. Am. Chem. Soc.* 1972, 94, 2699-2704.

[3] a) A. P. Downing, W. D. Ollis, I. O. Sutherland, *J. Chem. Soc. B* 1969, 111-119; b) T. Olsson, J. Sandström, *Acta Chem. Scand.* 1982, B36, 23-30.

[4] a) J. Dreyer, M. Klessinger, *J. Chem. Phys.* 1994, 101, 10655-10665; b) M. J. Bearpark, F. Bernardi, M. Olivucci, M. A. Robb, B. R. Smith, *J. Am. Chem. Soc.* 1996, 118, 5254-5260.

[5] a) E. D. Bergmann, E. Fischer, *Bull. Soc. Chim. Fr.* 1950, 1084-1091; b) E. D. Bergmann, E. Fischer, Y. Hirshberg, *Bull. Soc. Chim. Fr.* 1950, 1103-1104.

[6] T. W. Bell, V. J. Catalano, M. G. B. Drew, D. J. Phillips, *Chem. Eur. J.* 2002, 8, 5001-5006.

[7] B. S. Ong, B. Keoshkerian, T. I. Martin, G. K. Hamer, *Can. J. Chem.* 1985, 63, 147-152. A solution of 40% Triton B in methanol was used, rather than 40% Triton B in pyridine, as reported in the original procedure (94% yield).

[8] G. C. Paul, J. J. Gajewski, *Synthesis* 1997, 524-526.
[9] G. M. Sheldrick SHELXTL97: *Program for Structure Refinement*: University of Goettingen: Goettingen, Germany, 1997.

REFERENCES

Not consecutively numbered

1. P. M. Ajayan, J.-C. Charlier, and A. G. Rinzler, "Carbon nanotubes. From macromolecules to nanotechnology", Proc. Natl. Acad. Sci. U.S.A. 96, 14199 (1999).
2. P. J. F. Harris, "Carbon nanotubes and related structures: New materials for the 21st Century" (Cambridge Univ Press, Cambridge, UK, 1999).
3. R. Saito, Physical Properties of Carbon Nanotubes (Imperial College Press, London, UK, 1998).
4. D. S. Bethune, R. D. Johnson, J. R. Salem, M. S. de Vries, and C. S. Yannoni, "Atoms in carbon cages: the structure and properties of endohedral fullerenes", Nature 366 (1993).
5. S. Nagase, K. Kobayashi, and T. Akasaka, 'Endohedral metallofullerenes: new spherical cage molecules with interesting properties", Bull. Chem. Soc. Jpn. 69, 2131 (1996).
6. H. Shinohara, "Endohedral metallofullerenes", Rep. Prog. Phys. 63, 843 (2000).
7. P. Zanello, "Electrochemical and structural aspects of metallofullerenes", in Chem. Beginning Third Millennium, Proc. Ger.-Ital. Meet., edited by L. Fabbrizzi and A. Poggi (Springer-Verlag, Berlin, Germany, 2000) pp. 247-278.
8. A. L. Balch, \Structural inorganic chemistry of fullerenes and fullerene-like compounds", in Fullerenes: Chem., Phys. Technol., edited by K. M. Kadish and R. S. Ruoff (John Wiley and Sons. Inc., New York, N.Y., 2000), pp. 177-223.
9. O. A. Matthews, A. N. Shipway, and J. F. Stoddart, "Dendrimers—branching out from curiosities into new technologies", Prog. Polym. Sci. 23, 1 (1998).
10. A. W. Bosman, H. M. Janssen, and E. W. Meijer, "About Dendrimers: Structure, Physical Properties, and Applications", Chem. Rev. 99, 1665 (1999).
11. M. Fischer and F. Vogtle, "Dendrimers: From design to application—a progress report", Angew. Chem., Int. Ed. 38,885 (1999).
12. D. K. Smith, F. Diederich, and A. Zingg, "Supramolecular dendrimer chemistry: Molecular recognition within the dendritic environment", NATO ASI Ser., Ser. C (Supramolecular Science: Where It Is and Where It Is Going) 527 (1999).
13. C. J. Hawker, "Dendritic and hyperbranched macromolecules—precisely controlled macromolecular architectures", Adv. Polym. Sci. (Macromolecular Architectures) 147, 113 (1999).
14. F. Vogtle, ed., Dendrimers II: Architecture, Nanostructure and Supramolecular Chemistry (Topics of Current Chemistry, Vol. 210) (Springer, Berlin, Germany, 2000).
15. J.-M. Lehn, "Perspectives in supramolecular chemistry: From molecular recognition towards self-organization", Pure Appl. Chem. 66, 1961 (1994).
16. J.-M. Lehn, "Supramolecular chemistry and chemical synthesis. From molecular interactions to self-assembly", NATO ASI Ser., Ser. E (Chemical Synthesis) 320 (1996).
17. S. G. Bott and A. P. Marchand, eds., Special Issue: Structural Aspects of Molecular Recognition Supermolecular Assemblies. (Struct. Chem., Vol. 10, No. 3) (Kluwer, New York, N.Y., 1999).
18. G. Tsoucaris, ed., Current Challenges on Large Supramolecular Assemblies (NATO Sci. Ser., Ser. C, Vol. 519) (Kluwer, Dordrecht, Netherlands, 1999).
19. P. A. Gale, "Supramolecular chemistry: From complexes to complexity", Philos. Trans. R. Soc. London, Ser. A 358, 431 (2000).
20. E. Drexler, Engines of Creation (Anchor Press, New York, N.Y., 1987).
21. K. E. Drexler, Nanosystems: Molecular Machinery, Manufacturing, and Computation (John Wiley and Sons, New York, N.Y., 1992).
22. M. Gomez-Lopez, J. A. Preece, and J. F. Stoddart, "The art and science of self-assembling molecular machines", Nanotechnology 7 (1996).
23. V. Balzani, M. Gomez-Lopez, and J. F. Stoddart, "Molecular Machines", Acc. Chem. Res. 31, 405 (1998).
24. M. Gomez-Lopez and J. F. Stoddart, "Molecular and supramolecular nanomachines", in Handb. Nanostruct. Mater. Nanotechnol., Vol. 5, edited by H. S. Nalwa (Academic Press, 2000), pp. 225-275.
25. V. Balzani, A. Credi, F. Raymo, and J. F. Stoddart, "Artificial molecular machines", Agnew. Chem. Int. Ed. 39, 3348 (2000).
26. J.-P. Sauvage, ed., Molecular Motors and Machines, Vol. 99 of Structure and Bonding (Springer, Berlin, 2001).
27. N. J. Cordova, B. Ermentrout, and G. F. Oster, "Dynamics of single-motor molecules: The thermal ratchet model". Proc. Natl. Acad. Sci. U. S. A. 89, 339 (1992).
28. R. Cooke, "The structure of a molecular motor", Curr. Biol. 3, 590 (1993).
29. R. Cooke, "The actomyosin engine", FASEB J. 9, 636 (1995).
30. Y. Ishii, Y. Kimura, K. Kitamura, H. Tanaka, T. Wazawa, and T. Yanagida, "Imaging and nano-manipulation of single actomyosin motors at work", Clin. Exp. Pharmacol. Physiol 27, 229 (2000).
31. T. Yanagida, S. Esaki, A. H. Iwane, Y. Inoue, A. Ishijima, K. Kitamura, H. Tanaka, and M. Tokunaga, "Single-motor mechanics and models of the myosin motor", Philos. Trans. R. Soc. London, Ser. B 355, 441 (2000).
32. C. S. Peskin and G. Oster, "Coordinated hydrolysis explains the mechanical behavior of kinesin", Biophys. J. 68, 202s (1995).
33. S. Rice, A. W. Lin, D. Safer, C. L. Hart, N. Naber, B. O. Carragher, S. M. Cain, E. Pechatnikova, E. M. Wilson-Kubalek, M. Whittaker, E. Pate, R. Cooke, et al., "A structural change in the kinesin motor protein that drives motility", Nature 402, 778 (1999).
34. J. R. Dennis, J. Howard, and V. Vogel, "Molecular shuttles: directed motion of microtubules along nanoscale kinesin tracks", Nanotechnology 10, 232 (1999).
35. R. Stracke, K. J. Bohm, J. Burgold, H.-J. Schacht, and E. Unger, "Physical and technical parameters determining the functioning of a kinesin-based cell-free motor system", Nanotechnology 11, 52 (2000).
36. G. D. Bachand and C. D. Montemagno, "Constructing biomolecular motor-powered hybrid NEMS devices", Proc. SPIE-Int. Soc. Opt. Eng. 3892, 170 (1999).
37. C. Montemagno and G. Bachand, "Constructing nanomechanical devices powered by biomolecular motors", Nanotechnology 10, 225 (1999).
38. G. D. Bachand and C. D. Montemagno, "Constructing organic/inorganic NEMS devices powered by bimolecular motors", Biomed. Microdevices 2, 179 (2000).
39. R. K. Soong, G. D. Bachand, Bachand, H. P. Neves, A. G. Olkhovets, H. G. Craighead, and C. D. Montemagno, "Powering an Inorganic Nanodevice with a Biomolecular Motor", Science 290, 1555 (2000).
40. S. A. Nepogodiev and J. F. Stoddart, "Cyclodextrin-Based Catenanes and Rotaxanes", Chem. Rev. 98 (1998).
41. J. R. Dennis, J. Howard, and V. Vogel, "Directing the motion of molecular shuffles by shear deposited polymer $^-1$ ms", Polym. Mater. Sci. Eng. 80, 631 (1999).
42. F. M. Raymo and J. F. Stoddart, "Interlocked macromolecules", Chem. Rev. 99 (1999).
43. P. R, Ashton, R. Ballardini, V. Balzani, A. Credi, K. R. Dress, E. Ishow, C. J. Kleverlaan, O. Kocian, J. A. Preece, N. Spencer, J. F. Stoddart, M. Venturi, et al., "A photochemically driven molecular-level abacus", Chem.-Eur. J. 6 (2000).
44. A. M. Brouwer, C. Frochot, F. G. Gatti, D. A. Leigh, L. Mottier, F. Paolucci, S. Ro±a, and G. W. H. Wurpel, "Photoinduction of Fast, Reversible Translational Motion in a Hydrogen-Bonded Molecular Shuttle", Science 291, 2124 (2001).
45. T. R. Kelly, M. C. Bowyer, K. V. Bhaskar, D. Bebbington, A. Garcia, F. Lang, M. H. Kim, and M. P. Jette, "A molecular brake", J. Am. Chem. Soc. 116, 3657 (1994).
46. T. R. Kelly, I, Tellitu, and J. P. Sestelo, "In search of molecular ratchets", Angew. Chem., Int. Ed. Engl. 36, 1866 (1997).
47. T. R. Kelly, H. De Silva, and R. A. Silva, "Unidirectional rotary motion in a molecular system", Nature 401, 150 (1999).
48. T. R. Kelly, R. A. Silva, H. De Silva, S. Jasmin, and Y. Zhao, "A rationally designed prototype of a molecular motor", J. Am. Chem. Soc. 122, 6935 (2000).
49. A. M. Schoevaars and B. L. Feringa, "Towards a switchable molecular rotor. Unexpected dynamic behavior of functionalized overcrowded ethylenes", Book of Abstracts, 212th ACS National Meeting ORGN-134 (1996).
50. N. Koumura, R. W. J. Zijistra, R. A. Van Delden, N. Harada, and B. L. Feringa, "Light-driven monodirectional molecule rotor", Nature 401, 152 (1999).
51. N. Harada, N. Komura, and B. L. Feringa, "Chemistry of unique chiral olefins—A light-powered chiral molecular motor with monodirectional rotation", Nippon Kagaku Kaishi 9, 591 (2000).
52. R. A. van Delden, N. Koumura, N. Harada, and B. L. Feringa, "Unidirectional rotary motion in a liquid crystalline environment: Color tuning by a molecular motor", Proc. Nat. Acad. Sci. 99, 4945 (2002).
53. J. Vacek and J. Michl, "A molecular "Tinkertoy" construction kit: computer simulation of molecular propellers", New J. Chem. 21, 1259 (1997).
54. J. Vacek, A. Prokop, and J. Michl, "Simulation of chiral molecular mobiles", Book of Abstracts, 219th ACS National Meeting PHYS-130 (2000).
55. A. P. Davis, "Tilting at Windmills? The Second Law survives", Angew. Chem. Int. Ed. 37, 909 (1998).
56. R. Kuhn, H. Fischer, F. Neugebauer, and H. Fischer, "ÄUber Hochacide Kohlenwasserstoffe", Liebigs Ann. Chem. 654, 64 (1962).
57. I. Antipin, A. Vedernikov, and A. Konovalov, "Cryptate Acidity Scales. IV, Spectrophotometric and Conductometric Study of [2.1.1]cryptates of Lithium Salts of CH Acids", J. Org. Chem., USSR 25, 1 (1989).
58. L. A. Pinck and G. E. Hilbert, "Derivatives of Fluorene", J. Am. Chem. Soc. 69, 723 (1947).
59. G. Mehta, K. V. Rao, and K. Ravikumar, "Synthesis and X-ray crystal structure of 1,3,5-tris(fluoren-9-ylidenemethyl)benzene: Towards a C48-fragment of [60]-fullerene", J. Chem. Soc. Perkin Trans. 1 pp. 1787 {1788 (1995).
60. G. C. Paul and J. J. Gajewski, "Unexpected coupling reaction of 9-lithiobromomethylene-9H-fluorene with 6,6-dicyclopropylfulvene", Synthesis pp. 524 {526 (1997).
62. M. A. Schmid, H. G. Alt, and W. Milius, "Unbridged cyclopentaldienyl-fluorenyl complexes of zirconium as catalysts for homogeneous olefin polymerization", J. Organomet. Chem. 501, 101 (1995).
63. H. G. Alt and R. Zenk, "Syndiospezifische polymerisation von propylen: 2- und 2,7-substituierte metallocenkomplex des typs $(C_{13}H_{8-n}R_nCR_2C_5H_4) MC_{12}$ (n=1; 2; R=alkoxy, alkyl, aryl, Hal; R=Me, Ph; M=Zr, Hf)", J. Organomet. Chem. 522, 39 (1996).
64. B. S. Ong, B. Keoshkerian, T. I. Martin, and G. K. Hamer, "Synthesis, molecular and electron transport properties of 2-alkyltrinitrofluoren-9-ones", Can. J. Chem. 63, 147 (1985).
65. Q. Tian and R. C. Larock, "Synthesis of 9-alkylidene-9H-fluorenes by a novel palladium-catalyzed rearrangement", Org. Lett. 2, 3329 (2000).
66. R. C. Larock and Q. Tian, "Synthesis of 9-alkylidene-9H-fluorenes by a novel palladium-catalyzed cascade reaction of aryl halides and 1-aryl-1-alkynes", J. Org. Chem. 66, 7372 (2001).
67. L. F. Levy and H. Stephen, "CXXIII. 40 Aminophthalide and Some Derivatives", J. Chem. Soc. pp. 867-871 (1931).
68. J. Tirouflet, "Synthesis of substituted phthalides and substituted phthalic anhydrides and a study of the reactivity of the carbonyl group I. Preparation of ring-substituted phthalides. 2.5-Substituted phthalides", Bull. Soc. Sci. Bretagne 20, 35 (1951).
69. C. Donati, R. H. Prager, and B. A. Weber, "Potential GABAB receptor antagonists. III Folded baclofen Analogues Based on Phthalide", J. Chem. 42, 787 (1989).
70. J. Martin and R. G. Smith, "Factors in°uencing the basicities of triarylcarbinols. The synthesis of Sesquixanthydrol", J. Am. Chem. Soc. 86, 2252 (1964).
71. J. G. Smith and P. W. Dibble, "2-(Dimethoxymethyl) benzyl alcohol: A convenient isobenzofuran precursor", J. Org. Chem. 48, 5362 (1983).
72. H. W. Gibson, S.-H. Lee, P. T. Engen, P. Lecavalier, J. Sze, Y. X. Shen, and M. Bheda, "New Triarylmethyl Derivatives: "Blocking Groups" for Rutaxanes and Polyrotaxanes", J. Org. Chem. 58, 3748 (1993).
73. T. Masquelin and D. Obrecht, "A new approach to the synthesis of N-protected 2- and 5-substituted 3-halopyrroles", Synthesis pp. 276{284 (1995).
74. T. Lindel and M. HochgÄurtel, "Synthesis of the marine natural product oroidin and its Z-isomer", J. Org. Chem. 65, 2806 (2000).
75. P. Casara, C. Danzin, B. Metcalf, and M. Jung, "Stereospecific synthesis of (2R,5R)-hept-6-yne-2,5-diamine, a potent and selective enzyme-activated irreversible inhibitor of ornithine decarboxylase (ODC)", J. Chem. Soc. Perkin Trans. 1 1985, 2201 (1985).
76. R. C. Bernotas, G. Papandreou, J. Urbach, and B. Ganem, "A new family of Five-carbon iminoalditols which are potent glycosidase inhibitors", Tetrahedron Lett. 31, 3393 (1990).
77. K. Pal, M. L. Behnke, and L. Tong, "A general stereocontrolled synthesis of cis-2,3 disubstituted pyrrolidines and piperidines", Tetrahedron Lett. 34, 6205 (1993).

78. L. Contreras and D. B. MacLean, "Reactions of phthalans with dienophiles. I. Synthesis of naphthalenes flow phthalans and activated acetylenes", Can. J. Chem 58, 2573 (1980).
79. R. Cherkasov, G. Kutyrev, and A. Pudovik, "Organothiophosphorus reagents in organic synthesis", Tetrahedron 41, 2567 (1985).
80. M. P. Cava and M. I. Levinson, "Thionation reactions of Lawesson's reagents", Tetrahedron 41, 5061 (1985).
81. R. Knorr, A. Schnegg, E. Lattke, and E. Rpple, "1H-Kernresonanzverschiebungen in der GerÄustebene anisotroper. CO—, CN— and CC— Doppelbindungen", Chem. Ber, 112, 3490 (1979).
82. A. Tsuge, T. Yamasaki, T. Moriguchi, T. Matsuda, Y. Nagano, H. Nago, S. Mataka, S. Kajigaeshi, and M. Tashiro, "A facile synthesis of 1,8- and 1,7-bis(chloromethyl)°uorenes", Synthesis pp. 205{206 (1993).
83. V Sharma, B. Bachand, M. Simard, and J. D. Wuest, "Synthesis and structure of 2; 20-dihydroxybenzophenones and 1,8-dihydroxyfluorenones", J. Org. Chem. 59, 7785 (1994).
84. M. Yoshida, M. Minabe, and K. Suzuki, "Synthesis of 4H-cyclopenta[d,e,f]phenanthrene from fluorene skeleton", Bull. Chem. Soc. Jpn. 56, 2179 (1983).
85. M. Minabe, M. Yoshida, and T. Takayanagi, "A facile synthesis of 4H-cyclopenta[d,e,f]phenanthrene", Bull. Chem. Soc. Jpn. 61, 995 (1988).
86. W. Chew, R. C. Hynes, and D. N. Harpp, "Synthesis of substituted fluorenones and substituted 30,30-dichlorospiro[fluorene-9,20-thiiranes] and their reactivities", J. Org. Chem. 58, 4398 (1993).
87. D. S. Kemp and K. S. Petrakis, "Synthesis and Conformational Analysis of cis,cis-1,3,5-Trimethylcyclohexane-1,3,5-tricarboxylic Acid", J. Org. Chem. 46, 5140 (1981).
88. K. Tomooka, H. Yamamoto, and T. Nakai, "[1,2]-Wittig Rearrangement of Acetal Systems:A Highly Stereocontrolled Conversion of O-Glycosides to C-Glycosides", J. Am. Chem. Soc. 118, 3317 (1996).
89. P. GÄartner, M. F. Letschnig, M. KnollmÄuller, and H. VÄollenkle, "[1,2]-Wittig rearrangement of acetals. Part 1: Investigation about structural requirements", Tetrahedron: Asymmetry 10, 4811 (1999).
90. P. GÄartner, M. F. Letschnig, M. KnollmÄuller, and K. Mereiter, "[1,2]-Wittig rearrangement of acetals. Part 2: The influence of reaction conditions", Tetrahedron: Asymmetry 11, 1003 (2000).
91. K. Tomooka, H. Yamamoto, and T. Nakai, "Stereoselective Synthesis of Highly Functionalized C-Glycosides based on Acetal [1,2] and [1,4] Wittig Rearrangements", Angew. Chem. Int. Ed. 39, 4500 (2000).
92. K. Tomooka, M. Kikuchi, K. Igawa, M. Suzuki, P.-H. Keong, and T. Nakai, "Stereoselective Total Synthesis of Zaragozic Acid A based on an Acetal [1,2] Wittig Rearrangement", Angew. Chem. Int. Ed. 39, 4502 (2000).
93. J. Rebek, Jr, B. Askew, M. Kiloran, D. Nemeth, and F.-T. Lin, "Convergent Functional Groups. 3. A Molecular Cleft Recognizes Substrates of Complementary Size, Shape, and Functionality", J. Am. Chem. Soc. 109, 2426 (1987).
94. K. S. Jeong, A. V. Muehldorf, and J. Rebek, Jr, "Molecular Recognition. Asymmetric Complexation of Diketopiperazines", J. Am. Chem. Soc. 112, 6144 (1990).
95. K. S. Jeong, T. Tjivikua, A. Muehldorf, G. Deslongchamps, M. Famulok, and J. Rebek, Jr., "Convergent Functional Groups, 10. Molecular Recognition of Neutral Substrates", J. Am. Chem. Soc. 113, 201 (1991).
96. H. Izumi, O. Setokuchi, and Y. Shimizu, "Synthesis and Cyclization Reaction of cis,cis-1,3,5-Triformyl-1,3,5-trimethylcyclohexane", J. Org. Chem. 62, 1173 (1997).
97. H. Izumi and S. Futamura, "Intermolecular Interaction of Adjacent Hydroxymethyl, Formyl, and Carboxyl Groups: Proximity Effect in the Swern Oxidation of cis,cis-1,3,5-Tris(hydroxymethyl)-1,3,5-trimethylcyclohexane", J. Org. Chem. 64, 4502 (1999).
98. R. Boyce, B. A. Hayes, W. S. Murphy, and E. A. O'Riordan, "1,1-Diphenylalkenes. Part V. C-1 vs. C-3 Alkylation of Allylic Carbanions; Applicability of the Principle of Least Motion", J. Chem. Soc., Perkin Trans. I pp. 531-534 (1975).
99. E. Ghera and Y. Sprinzak, "Reactions of Active Methylene Compounds in Pyridine Solution. II. Aldol-type Reactions of Indene and Fluorene", J. Am. Chem. Soc. 82, 4945 (1960).
100. M. Minabe and K. Suzuki, "Bildung von 1,4-Bis(2,20)-biphenylylen-1,3-butadien", Bulletin of the Chemical Society of Japan 46, 1573 (1973).
101. I. Von and E. C. Wagner, "Some 9-Acyl°uorenes and Derived Vinylamines", J. Org. Chem. 9, 155 (1944).
102. B. W. Howk and J. C. Sauer, "Synthesis of Acetylenic Acetals, Ketals and Orthoesters", J. Am. Chem. Soc. 80, 4607 (1958).
103. W. Kandeliner, T. Maier, and J. Kapassakalidis, "Ein neues ergiebiges Verfahren zur Herstellung von Trialkylorthobenzoaten und Trialkyl-orthophenylpropynoaten", Synthesis (1981).
104. B. Morgan, A. Zaks, D. R. Dodds, J. Liu, R. Jain, S. Megati, F. G. Njoroge, and V. M. Girijavallabhan, "Enzymatic kinetic resolution or piperidine atropisomers: Synthesis of a key intermediate of the farnesyl protein transferase inhibitor, SCH66336", J. Org. Chem. 65, 5451 (2000).
105. V Okamoto, M. Kawashima, and K. Hatada, "XI. Controlled chiral recognition of cellulose triphenylcarbamate derivatives supported on silica gel", J. Chromatogr. 363, 173 (1986).
106. Y. Okamoto and E. Yashima, "Polysaccharide Derivatives for Chromatographic Separation of Enantiomers", Angew. Chem. Int. Ed. 37, 1020 (1998).
107. E. Yashima, C. Yamamoto, and Y. Okamoto, "Polysaccharide-based chiral LC columns", Synlett pp. 344{360 (1998).
108. B. Space, H. Rabitz, A. LÄorincz, and P. Moore, "Feasiblity of using photophoresis to create a concentration gradient of solvated molecules", J. Chem. Phys. 105, 9515 (1996).
109. J. Vacek and J. Michl, "Molecular dynamics of a grid-mounted molecular dipolar rotor in a rotating electric field", Proc. Natl. Acad. Sci. U.S.A. 98, 5481 (2001).
122. H.-H. Perkampus, I. Sandeman, and C. Timmons, eds., *UV Atlas of Organic Compounds*, vol. V (Plenum, New York, 1971).
123. M. Neuenschwander, R. Vogeli, H.-P. Fahrni, H. Lehman, and J.-P. Ruder, "Synthese von benzofulvenen und dibenzofulvene uber 1-chloroalkyl-acetate", *Helv. Chim. Acta* 60, 1073 (1977).
124. R. S. Murphy, C. P. Moorlag, W. H. Green, and C. Bohne, "Photophysical characterization of fluorenone derivatives", *J. Photochem. Photobiol. A: Chemistry* 110, 123 (1997).
125. T. Vatsuhashi, Y. Nakajima, T. Shimada, and H. Inoue, "Photophysical properties of intramolecular charge-transfer excited singlet state of aminofluorenone derivatives", *J. Phys. Chem. A* 102, 3018 (1998).

170. A. L. Huston and C. T. Reimann, "Photochemical bleaching of adsorbed rhodamine 6 g as a probe of binding geometries on a fused-silica surface", *Chem. Phys.* 149, 401 (1991).

171. C. A. Goss, d. D. H. Charych, and M. Majda, "Application of (3-mercaptopropyl)trimethoxysilane as a molecular adhesive in the fabrication of vapordeposited gold electrodes on glass substrates", *Anal. Chem.* 63, 85 (1991).

172. D. L. Pilloud, F. Rabanal, B. R. Gibney, R. S. Farid, P. L. Dutton, and C. C. Moser, "Self-assembled monolayers of synthetic hemoproteins on silanized quartz", *J. Phys. Chem. B* 102, 1926 (1998).

173. M. Lieberherr, C. Fattinger, and W. Lukosz, "Optical-environment-dependent effects on the fluorescence of submonomolecular dye layers on interfaces", *Surf. Sci.* 189, 954 (1987).

174. H. Sano, d. G. Mizutani, and S. Ushioda, "Dipole radiation-pattern from surface adsorbed dye molecules—effects of surface-roughness", *Surf. Sci.* 223, 621 (1989).

175. X. S. Xie and J. K. Trautman, "Optical studies of single molecules at room temperature", *Annu. Rev. Phys. Chem.* 49, 441 (1998).

176. W. Moerner and M. Orritt, "Illuminating single molecules in condensed matter", *Science* 283, 1670(1999).

177. P. Tamarat, A. Maali, B. Lounis, and M. Orrit, "Ten years of single-molecule spectroscopy", *J. Phys. Chem. A* 104, 1 (2000).

178. D. C. Hanley and J. M. Harris, "Quantitative Dosing of Surfaces with Fluorescent Molecules: Characterization of Fractional Monolayer Coverage by Counting Single Molecules", *Anal. Chem.* 73, 5030 (2001).

179. S. Nie, D. T. Chiu, and R. N. Zare, "Probing individual molecules with confocal fluorescence microscopy", *Science* 266, 1018 (1994).

180. J. K. Trautman and d. J. J. Macklin, "Time-resolved spectroscopy of single molecules using near-field; far-field optics", *Chem. Phys.* 205, 221 (1996).

181. T. Ha, T. Enderle, D. S. Chemla, P. R. Selvin, and S. Weiss, "Single molecule dynamics studied by polarization modulation", *Phys. Rev. Lett.* 77, 3979 (1996).

182. R. Dickson, D. Norris, and W. Moerner, "Simultaneous imaging of individual molecules aligned both parallel; perpendicular to the optic axis", *Phys. Rev. Lett.* 81, 5322 (1998).

183. T. Ha, T. A. Laurence, D. S. Chemla, and S. Weiss, "Polarization spectroscopy of single fluorescent molecules", *J. Phys. Chem. B* 103, 6839 (1999).

184. P. Bernath, *Spectra of Atoms and Molecules* (Oxford University Press, New York, N.Y., 1995).

185. G. Hahner, A. Marti, N. D. Spencer, and W. R. Caseri, "Orientation and electronic structure of methylene blue on mica: A near X-ray absorption .ne structure spectroscopy study", *J. Chem. Phys.* 104, 7749 (1996).

186. T. Vallant, H. Brunner, U. Mayer, H. Ho.mann, T. Leitner, R. Resch, and G. Friedbacher, "Formation of self-assembled octadecylsiloxane monolayers on mica; silicon surfaces by atomic force microscopy and infrared spectroscopy", *J. Phys. Chem. B* 102, 7190(1998).

187. D. Brovelli, W. R. Caseri, and G. Hahner, "Self-assembled monolayers of alkylammonium ions on mica: Direct determination of the orientation of the alkyl chains", *J. Colloid Interface Sci.* 216, 418 (1999).

188. M. Li, A. Wang, G. Mao, and L. Daehne, "Surface-directed adsorption in the expitaxy growth of streptocyanine dye crystals", *J. Phys. Chem. B* 103, 11161 (1999).

201. Z. A. Shabarova, M. G. Ivanovskaya, and M. G. Isaguliants, "DNA-like duplexes with repetitions: efficient template-guided polycondensation of decadeoxyribonucleotide imidazolide", *FEBS Lett* 154, 288 (1983).

202. B. C. Chu, G. M. Wahl, and L. E. Orgel, "Derivatization of unprotected polynucleotides", *Nucleic Acids Res.* 11, 6513 (1983).

203. C. R. Cremo, J. M. Neuron, and R. G. Yount, "Interaction of myosin subfragment 1 with fluorescent ribose-modified nucleotides. A comparison of vanadate trapping and SH1-SH2 crosslinking", *Biochemistry* 29, 3309 (1990).

204. F. M. Ausubel, R. Brent, R, E. Kingston, and D. D. Moore, eds., *Short protocols in molecular biology: A compendium of methods from current protocols in molecular biology* (John Wiley and Sons, New York, N.Y., 1999), 4th ed.

205. T. Strother, R. J. Hamers, and L. M. Smith, "Chemical synthesis of oligonucleotides containing a free sulphydryl group and subsequent attachement of thiol specific probes", *Nucleic Acids Research* 28, 3535 (2000).

206. B. A. Connolly and P. Rider, "Chemical synthesis of oligonucleotides containing a free sulphydryl group and subsequent attachment of thiol specific probes", *Nucleic Acids Res* 13, 4485 (1985).

207. C. R. Cremo, J. R. Sellers, and K. C. Facemyer, "Two heads are required for phosphorylation-dependent regulation of smooth muscle myosin", *J. Biol. Chem.* 270, 2171 (1995).

208. D. B. Haniford and D. E. Pulleyblank, "Facile transition of poly[d(TG)×d(CA)] into a left-handed helix in physiological conditions", *Nature* 302, 632 (1983).

209. C. K. Singleton, M. W. Kilpatrick, and R. D. Wells, "S1 nuclease recognizes DNA conformational junctions between left-handed helical (dT-dG n. dC-dA)n and contiguous right-handed sequences", *J. Biol Chem* 259, 1963 (1984).

210. M. J. McLean, J. A. Blaho, M. W. Kilpatrick, and R. D. Wells, "Consecutive A X T pairs can adopt a left-handed DNA structure", *Proc Natl Acad Sci USA* 83, 5884 (1986).

The claimed invention is:

1. A compound of formula (2):

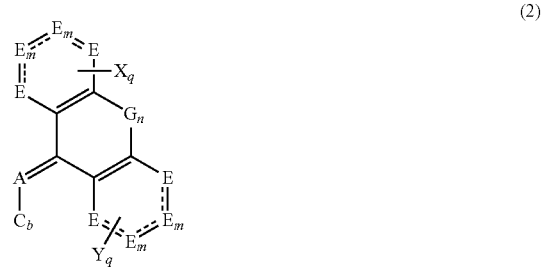

wherein:

$C_b$ is a carbocyclic or heterocyclic group wherein the atom within the cyclic structure is singly bound to A and is a bridgehead carbon atom;

A is CR, COR, CSR, CNR$_2$, CCN, CCONR$_2$, CNO$_2$, CNNAr, or CX', wherein Ar is aryl or heteroaryl and X' is a halide;

G is CR$_2$, >C═CR$_2$, C═O, C═S, C═NR, NR, O, or S;

n is 0, 1, or 2;

E is independently CH, CH$_2$, N, NH, O, or S;

m is independently 0, 1, 2, or 3;

X is independently R$^1$, SiR$^1{}_3$, ═NR$^1$, NR$^1{}_2$, ═O, OR$^1$, ═S, or SR$^1$;

Y is independently $R^1$, $SiR^1_3$, $=NR^1$, $NR^1_2$, $=O$, $OR^1$, $=S$, or $SR^1$;

q is independently 0, 1, 2, 3, or 4;

R is independently H;
 substituted or unsubstituted, branched or straight chain $C_1$-$C_{18}$ alkyl;
 substituted or unsubstituted, branched or straight chain $C_2$-$C_{18}$ alkenyl;
 substituted or unsubstituted, branched or straight chain $C_2$-$C_{18}$ alkynyl;
 —$(OCH_2CH_2)_{1-15}OH$; —$(OC_3H_6)_{1-15}OH$;
 substituted or unsubstituted, saturated or unsaturated, carbocycles or heterocycles; or
 substituted or unsubstituted aryl or heteroaryl; and $R^1$ is independently H;
 substituted or unsubstituted, branched or straight chain $C_1$-$C_{18}$ alkyl;
 substituted or unsubstituted, branched or straight chain $C_2$-$C_{18}$ alkenyl;
 substituted or unsubstituted, branched or straight chain $C_2$-$C_{18}$ alkynyl;
 —$(OCH_2CH_2)_{1-15}OH$; —$(OC_3H_6)_{1-15}OH$;
 substituted or unsubstituted, saturated or unsaturated, fused or unfused carbocycles or heterocycles; or
 substituted or unsubstituted, fused or unfused aryl or heteroaryl;

wherein when $R^1$ is a cyclic structure the heteroatoms Si, N, O, or S within the definitions of X and Y may form part of the cyclic structure.

2. A compound of claim 1, wherein $C_b$ is a bi-cyclic carbocycle or heterocycle.

3. A compound of claim 1, wherein $C_b$ is a tri-cyclic carbocycle or heterocycle.

4. A compound of claim 1, wherein

A is CR;

G is $CR_2$, NR, O, or S;

n is 0 or 1;

E is independently CH, $CH_2$, N, NH, O, or S;

m is independently 1 or 2;

X is independently $R^1$, $=NR^1$, $NR^1_2$, $=O$, $OR^1$, $=S$, or $SR^1$;

Y is independently $R^1$, $=NR^1$, $NR^1_2$, $=O$, $OR^1$, $=S$, or $SR^1$;

q is independently 0, 1, 2, 3, or 4;

R is independently H;
 substituted or unsubstituted, branched or straight chain $C_1$-$C_9$ alkyl;
 substituted or unsubstituted, branched or straight chain $C_2$-$C_9$ alkenyl;
 substituted or unsubstituted, branched or straight chain $C_2$-$C_9$ alkynyl;
 —$(OCH_2CH_2)_{1-7}OH$; —$(OC_3H_6)_{1-7}OH$;
 substituted or unsubstituted, saturated or unsaturated, carbocycles or heterocycles; or
 substituted or unsubstituted aryl or heteroaryl; and $R^1$ is independently H;
 substituted or unsubstituted, branched or straight chain $C_1$-$C_9$ alkyl;
 substituted or unsubstituted, branched or straight chain $C_2$-$C_9$ alkenyl;
 substituted or unsubstituted, branched or straight chain $C_2$-$C_9$ alkynyl;
 —$(OCH_2CH_2)_{1-7}OH$; —$(OC_3H_6)_{1-7}OH$;
 substituted or unsubstituted, saturated or unsaturated, fused or unfused carbocycles or heterocycles; or
 substituted or unsubstituted, fused or unfused aryl or heteroaryl;

wherein when $R^1$ is a cyclic structure the heteroatoms Si, N, O, or S within the definitions of X and Y may form part of the cyclic structure.

5. A compound of claim 4, wherein

A is CR;

G is $CR_2$, or NR;

n is 0 or 1;

E is independently CH, $CH_2$, N, or NH;

each m is 1;

X is independently $R^1$, $NR^1_2$, $OR^1$, or $SR^1$;

Y is independently $R^1$, $NR^1_2$, or $OR^1$;

q is independently 0, 1, or 2;

R is independently H;
 substituted or unsubstituted, branched or straight chain $C_1$-$C_5$ alkyl;
 substituted or unsubstituted, branched or straight chain $C_2$-$C_5$ alkenyl;
 substituted or unsubstituted, branched or straight chain $C_2$-$C_5$ alkynyl;
 substituted or unsubstituted, saturated or unsaturated, carbocycle or heterocycle selected from the group consisting of cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and their corresponding iso-forms; or substituted or unsubstituted fused or unfused aryl or heteroaryl selected from the group consisting of phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenathtryl, and their corresponding iso-forms; and $R^1$ is independently H;
 substituted or unsubstituted, branched or straight chain $C_1$-$C_4$ alkyl;
 substituted or unsubstituted, branched or straight chain $C_2$-$C_4$ alkenyl;
 substituted or unsubstituted, branched or straight chain $C_2$-$C_4$ alkynyl;
 substituted or unsubstituted, saturated or unsaturated, fused or unfused carbocycles or heterocycles selected from the group consisting of cyclopropyl, cyclobutyl, cyclopentyl, cyclohexyl, pyrrolidinyl, piperidyl, imidazolidinyl, pyrazolidinyl, pyrazolinyl, piperazinyl, morpholinyl, chromanyl, indolinyl, and their corresponding iso-forms; or substituted or unsubstituted fused or unfused aryl or heteroaryl selected from the group consisting of phenyl, benzyl, naphthyl, furyl, benzofuranyl, pyranyl, pyrazinyl, thienyl, pyrrolyl, imidazolyl, pyridyl, pyrimidinyl, pyridazinyl, indolyl, indolizinyl, indoazolyl, purinyl, quinolyl, thiazolyl, phthalazinyl, quinoxalinyl, quinazolinyl, benzothienyl, anthryl, phenathtryl, and their corresponding iso-forms.

6. A compound of claim 5, wherein

A is CR;

G is $CR_2$, or NR;

n is 0 or 1;

E is independently CH, $CH_2$, N, or NH;

each m is 1;

X is independently $R^1$, $NR^1{}_2$, or $OR^1$;

Y is independently $R^1$, $NR^1{}_2$, or $OR^1$;

q is independently 0, 1, or 2;

R is independently H, methyl, ethyl, propyl, isopropyl, butyl, isobutyl, tert-butyl, cyclopentyl, cyclohexyl, phenyl, or pyridinyl; and $R^1$ is independently H, methyl, ethyl, propyl, isopropyl, butyl, isobutyl, tert-butyl, cyclopentyl, cyclohexyl, phenyl, or pyridinyl.

7. A compound of claim 1, wherein the moiety of formula (2) defined by

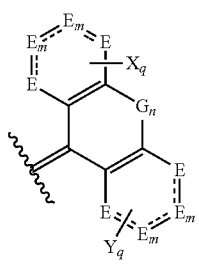

is selected from the group consisting of 4H-cyclopenta-[def]phenanthrene, 7H-dibenzo[c,g]fluorene, 13H-dibenzo[a,i]fluorene, 13H-dibenzo[a,g]fluorene, 11H-benzo[a]fluorene, 7H-benzo[c]fluorene, and derivatives of hexafulvenes and heptafulvenes.

8. A compound of formula (2) as recited in claim 1 having the structure:

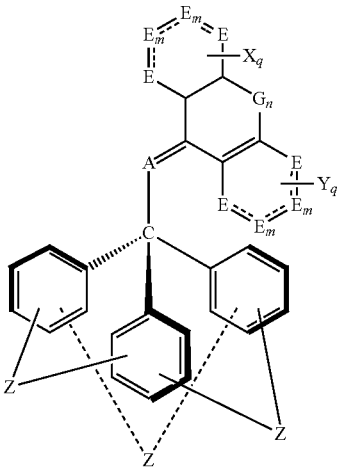

wherein Z is substituted or unsubstituted, branched or straight chain $C_3$-$C_9$ alkylene; substituted or unsubstituted, branched or straight chain $C_3$-$C_9$ alkenylene; substituted or unsubstituted, branched or straight chain $C_3$-$C_9$ alkynylene; —$(OCH_2CH_2)_{1-3}O$—; —$(OC_3H_6)_{1-3}O$—; substituted or unsubstituted, saturated or unsaturated, divalent carbocycles or heterocycles; or substituted or unsubstituted arylene or heteroarylene.

9. A compound of formula (2) as recited in claim 1 having the structure:

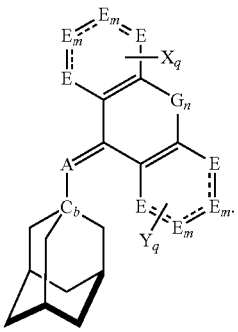

* * * * *